United States Patent
Ip et al.

(10) Patent No.: US 8,722,714 B2
(45) Date of Patent: May 13, 2014

(54) OXAZOLIDINE DERIVATIVES AS NMDA ANTAGONISTS

(75) Inventors: Nancy Yuk-Yu Ip, Hong Kong (CN); Hua-Jie Zhu, Kunming (CN); Fanny Chui-Fun Ip, Hong Kong (CN)

(73) Assignee: The Honk Kong University of Science and Technology, Kowloon, Hong Kong (CN)

( * ) Notice: Subject to any disclaimer, the term of this patent is extended or adjusted under 35 U.S.C. 154(b) by 507 days.

(21) Appl. No.: 12/812,940

(22) PCT Filed: Jan. 16, 2009

(86) PCT No.: PCT/CN2009/070178
§ 371 (c)(1),
(2), (4) Date: Feb. 17, 2011

(87) PCT Pub. No.: WO2009/092324
PCT Pub. Date: Jul. 30, 2009

(65) Prior Publication Data
US 2011/0144168 A1 Jun. 16, 2011

Related U.S. Application Data

(60) Provisional application No. 61/021,608, filed on Jan. 16, 2008.

(51) Int. Cl.
*C07D 263/04* (2006.01)
*C07D 413/06* (2006.01)

(52) U.S. Cl.
USPC ......................................... 514/374; 548/215

(58) Field of Classification Search
None
See application file for complete search history.

(56) References Cited

U.S. PATENT DOCUMENTS

2008/0108828 A1 5/2008 Onoda et al.

FOREIGN PATENT DOCUMENTS

| CN | 1539837 A | 10/2004 |
| WO | WO 98/15542 A1 | 4/1998 |
| WO | WO 2006/046595 A1 | 5/2006 |

OTHER PUBLICATIONS

Bergmann et al, Journal of American Chemical Society (1953), 75, 358-61.*
Dai, W.-M. et al., "Chiral Ligands Derived from Abrine. 2. Oxazolidines as Promoters for Enantioselective Addition of Diethylzinc toward Aromatic Aldehydes," *Tetrahedron: Asymmetry*, 1996, vol. 7, No. 5, pp. 1245-1248.
International Search Report mailed on Apr. 16, 2009, for International Application No. PCT/CN2009/070178 filed on Jan. 16, 2009, 6 pages.
Bergmann et al., Journal of the American Chemical Society, 1951, vol. 73, pp. 5662-4 (see CAS abstract acc. No. 1953:3316).
Juhasz et al., Journal of Heterocyclic Chemistry, 2007, vol. 44(6), pp. 1465-1473 (see CAS abstract acc. No. 2007:1328640).
Pihlaja et al., Rapid Communications in Mass Spectrometry, 2008, vol. 22(10), pp. 1510-1518 (see CAS abstract acc. No. 2008:632905).
Sini et al., Chemistry—A European Journal, 2008, vol. 14(11), pp. 3363-3370 (see CAS abstract acc. No. 2008:518921).
Sriramurthy et al., Journal of the American Chemical Society, 2007, vol. 129(43), pp. 12928-12929 (see CAS abstract acc. No. 2007:1131343).
Wenzel et al., Chirality, 2008, vol. 21(1), pp. 6-10, (see CAS abstract acc. No. 2009:14325).
WO2007/148135, Angeletti P IST Richerche Bio, (see CAS abstract acc. No. 2007:1470279).

* cited by examiner

*Primary Examiner* — Kamal Saeed
(74) *Attorney, Agent, or Firm* — Kilpatrick Townsend & Stockton LLP

(57) ABSTRACT

The present invention provides therapeutically active oxazolidine derivatives and compositions as NMDA antagonists, which are useful in preventing and treating central nervous system disorders by inhibiting over-activation of NMDA receptors. In one aspect, the present invention provides methods of treating and/or preventing neurodegenerative diseases and neuropathological disorders, methods of providing neuroprotection under stress conditions such as a stroke, and methods of enhancing the brain's cognitive functions in mammals and humans. For example, the compounds can prevent glutamate-induced neuro-toxicity by inhibiting the activities of the NMDA receptor in the presence of toxic doses of NMDA. In addition, the compounds can potentiate the calcium current in the presence of low dose of NMDA.

46 Claims, 20 Drawing Sheets b.

c.

d.

OXAZOLIDINE DERIVATIVES AS NMDA ANTAGONISTS

This application claims priority to U.S. Provisional Patent Application No. 61/021,608 filed Jan. 16, 2008, which application is incorporated herein by reference in its entirety and for all purposes.

BACKGROUND OF THE INVENTION

N-methyl-D-aspartate (NMDA) receptors are ligand-gated ion channels located primarily within the central nervous system (CNS). They belong to the family of ionotropic glutamate receptors and exist as multiple subtypes due to the different combinations of subunits—NR1, NR2 (NR2A, NR2B, NR2C, NR2D) and NR3—that can be expressed. In addition to the agonist binding site, NMDA receptors have multiple distinct binding sites for various compounds that enhance, modulate and inhibit the activation of the receptors.

It is known that NMDA receptors are involved in neuronal communication and play important roles in synaptic plasticity and mechanisms that underlie learning and memory. Under normal conditions, NMDA receptors engage in synaptic transmission via the neurotransmitter glutamate, which regulates and refines synaptic growth and plasticity. However, when there are abnormally high levels of glutamate (i.e. under pathological conditions), NMDA receptors become over-activated, resulting in an excess of $Ca^{2+}$ influx into neuronal cells, which in turn leads to excitotoxicity and the activation of several signaling pathways that trigger neuronal apoptosis. Glutamate-induced apoptosis in brain tissue also accompanies oxidative stress resulting in loss of ATP, loss of mitochondrial membrane potential, and the release of reactive oxygen species and reactive nitrogen species (e.g. $H_2O_2$, NO, OONO$^-$, $O_2^-$) causing associated cell damage and death. Decreased nerve cell function and neuronal cell death eventually occur. Excitotoxicity also occurs if the cell's energy metabolism is compromised.

Over-activation of the NMDA receptors is implicated in neurodegenerative diseases and other neuro-related conditions as it causes neuronal loss and cognitive impairment, and also plays a part in the final common pathway leading to neuronal injury in a variety of neurodegenerative disorders such as amyotrophic lateral sclerosis, Parkinson's disease, Alzheimer's disease and Huntington's disease, as well as conditions such as stroke. Recent findings have implicated NMDA receptors in many other neurological disorders, such as multiple sclerosis, cerebral palsy (periventricular leukomalacia), and spinal cord injury, as well as in chronic and severe mood disorders (Mathew S J et al., Rev Bras Psiquiatr, 27:243-248 (2005)).

NMDA receptors play crucial roles in both regulating and promoting normal nervous system functions as well as in causing cell-death, which leads to lethal conditions. There has been increasing evidence that the type of signal given to a cell depends on the location of the activated NMDA receptor. Growth and survival-promoting signals result from the activated synaptic NMDA receptors, while cell death causing signals result from the extrasynaptic NMDA receptors. Recent studies also indicate that the activated synaptic NMDA receptors lead to robust phosphorylation of the transcription factor CREB on the transcriptional regulatory residue Ser133 and promote CREB-dependent gene expression and neuronal survival. However, the activated extrasynaptic NMDA receptors transiently phosphorylate CREB and do not activate CREB-dependent gene expression, resulting in neuronal cell death (Hardingham G E et al., Nat Neurosci, 5: 405-414 (2002)).

Yet, there are few effective therapeutic agents for excitotoxicity to alleviate symptoms of its associated neuronal disorders. One complication for the development of effective NMDA antagonists as neurotherapeutic drugs is that many NMDA antagonists also exhibit psychotogenic and neurotoxic properties. For example, MK-801 (dizocilpine maleate) is capable of providing certain degree of neuroprotection in ischemic stroke, but is associated with pyschotropic and adverse motor effects. Thus, it is desirable to identify and/or to develop compounds that can potentiate NMDA synaptic activity resulting in neuroprotection.

Therefore, there is a need to develop effective NMDA antagonists that are capable of (i) preventing and/or treating CNS disorders, such as excitotoxicity, neurodegenerative diseases and neuropathological conditions; (ii) providing neuroprotection under stress conditions, such as a stroke; and (iii) enhancing the brain's cognitive functions. The present invention satisfies this and other needs.

BRIEF SUMMARY OF THE INVENTION

In one aspect, the present invention provides a compound of formula (I):

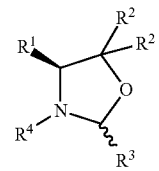

or a pharmaceutically acceptable salt, N-oxide, prodrug, hydrate and isomers thereof; wherein $R^1$ is selected from the group consisting of $(C_1-C_8)$alkyl, $(C_1-C_8)$heteroalkyl, arylalkyl, $(C_3-C_8)$cycloalkyl, $(C_3-C_8)$cycloalkyl-alkyl, heterocycloalkyl, heterocycloalkyl-$(C_1-C_6)$alkyl, heteroaryl-$(C_1-C_6)$alkyl, heterocyclyl-alkyl and aryl;

$R^2$ and $R^3$ are each independently selected from the group consisting of —H, $(C_1-C_8)$alkyl, $(C_1-C_8)$heteroalkyl, heteroaryl-alkyl and aryl;

$R^4$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, —X$^1$S(O)R$^a$, —X$^1$S(O)$_2$R$^a$, —X$^1$SO$_2$NH$_2$, —X$^1$S(O)$_2$NHR$^a$, —X$^1$S(O)$_2$N(R$^a$)$_2$, —X$^1$C(O)NH$_2$, —X$^1$C(O)NHR$^a$, —X$^1$C(O)N(R$^a$)$_2$, —X$^1$C(O)R$^a$, —X$^1$C(O)H, —X$^1$C(=S)R$^a$, —X$^1$CO$_2$H, —X$^1$CO$_2$R$^a$, —X$^1$P(O)(OR$^a$)$_2$ and an amino protecting group; wherein R$^a$ is $(C_1-C_8)$alkyl or aryl and each X$^1$ is independently a bond or an $(C_1-C_4)$ alkylene;

the wavy line denoted by ⌇ indicates the carbon to which the wavy line is attached has a stereoconfiguration of R, S or a mixture (racemic) thereof;

optionally, $R^1$ and $R^4$ together with the atoms to which they are attached form a 5-membered heterocyclic ring containing 0-1 additional ring heteroatom selected from O or N; and wherein each of $R^1$-$R^4$ groups is optionally substituted with from 1-3 R$^b$ substituents independently selected from the group consisting of halogen, —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —SR$^c$, —S(O)R$^c$, —S(O)$_2$R$^c$, —SO$_2$NH$_2$, —S(O)$_2$NHR$^c$, —S(O)$_2$N(R$^c$)$_2$, —NHS(O)$_2$R$^c$, —NR$^c$S(O)$_2$R$^c$, —C(O)NH$_2$, —C(O)NHR$^c$, —C(O)N(R$^c$)$_2$, —C(O)R$^c$, —C(O)H, —C(=S)R$^c$, —NHC(O)R$^c$, —NR$^c$C(O)R$^c$, —NHC(O)NH$_2$, —NR$^c$C(O)NH$_2$, —NR$^c$C(O)NHR$^c$, —NHC(O)NHR$^c$, —NR$^c$C(O)N(R$^c$)$_2$, —NHC(O)N(R$^c$)$_2$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —NR$^c$S(O)NH$_2$, —NR$^c$S(O)$_2$NHR$^c$, —NH$_2$C(=NR$^c$)NH$_2$, —N=C(NH$_2$)NH$_2$, —C(=NR$^c$)NH$_2$, —N$_3$, —NH—OH, —NR$^c$—OH, —NR$^c$—OR$^c$, —N=C=O, —N=C=S, —Si(R$^c$)$_3$, —NH—NHR$^c$, —NHC(O)NHNH$_2$, —P(O)(OR$^c$)$_2$, —N=C=NR$^c$ and —S—CN, wherein each R$^c$ is independently an alkyl or aryl, wherein R$^c$ is optionally further substituted with from 1-3 substituents selected from the group consisting of halogen, —OH, —OR$^d$, —SH, —SR$^d$, —S(O)$_2$R$^d$, —SO$_2$NH$_2$, —C(O)NH$_2$, —C(O)NHR$^d$, —C(O)N(R$^d$)$_2$, —C(O)R$^d$, —C(O)H, —NHC(O)R$^d$, —NR$^d$C(O)R$^d$, —CO$_2$H, —CO$_2$R$^d$, —R$^d$, —CN, —NO$_2$, —NH$_2$, —NHR$^d$, —N(R$^d$)$_2$, —NH—OH, —NR$^d$—OH, —NR$^d$—OR$^d$, —N=C=O, —N=C=S, —NH—NHR$^d$ and —S—CN, wherein each R$^d$ is independently an (C$_1$-C$_6$)alkyl.

In another aspect, the present invention provides a method of inhibiting the activities of an NMDA receptor. The method includes contacting compounds of formula I or any of the compounds as described herein with the NMDA receptor.

In yet another aspect, the present invention provides methods of preventing and/or treating central nervous system disorders in a mammal. In one embodiment, the present invention provides methods for preventing and/or treating a neurodegenerative disease and neuropathological conditions in a mammal. In another embodiment, the present invention provides a method for enhancing the brain's cognitive function in a mammal. In yet another embodiment, the present invention provides a method of preventing neuronal damage under a stress condition, such as a stroke in a mammal. The methods for treating and/or preventing CNS disorders in the above embodiments include administering to the mammal a therapeutically effective amount of compounds of formula I or any of the compounds as described herein.

DETAILED DESCRIPTION OF THE INVENTION

I. Introduction

Figure 1:
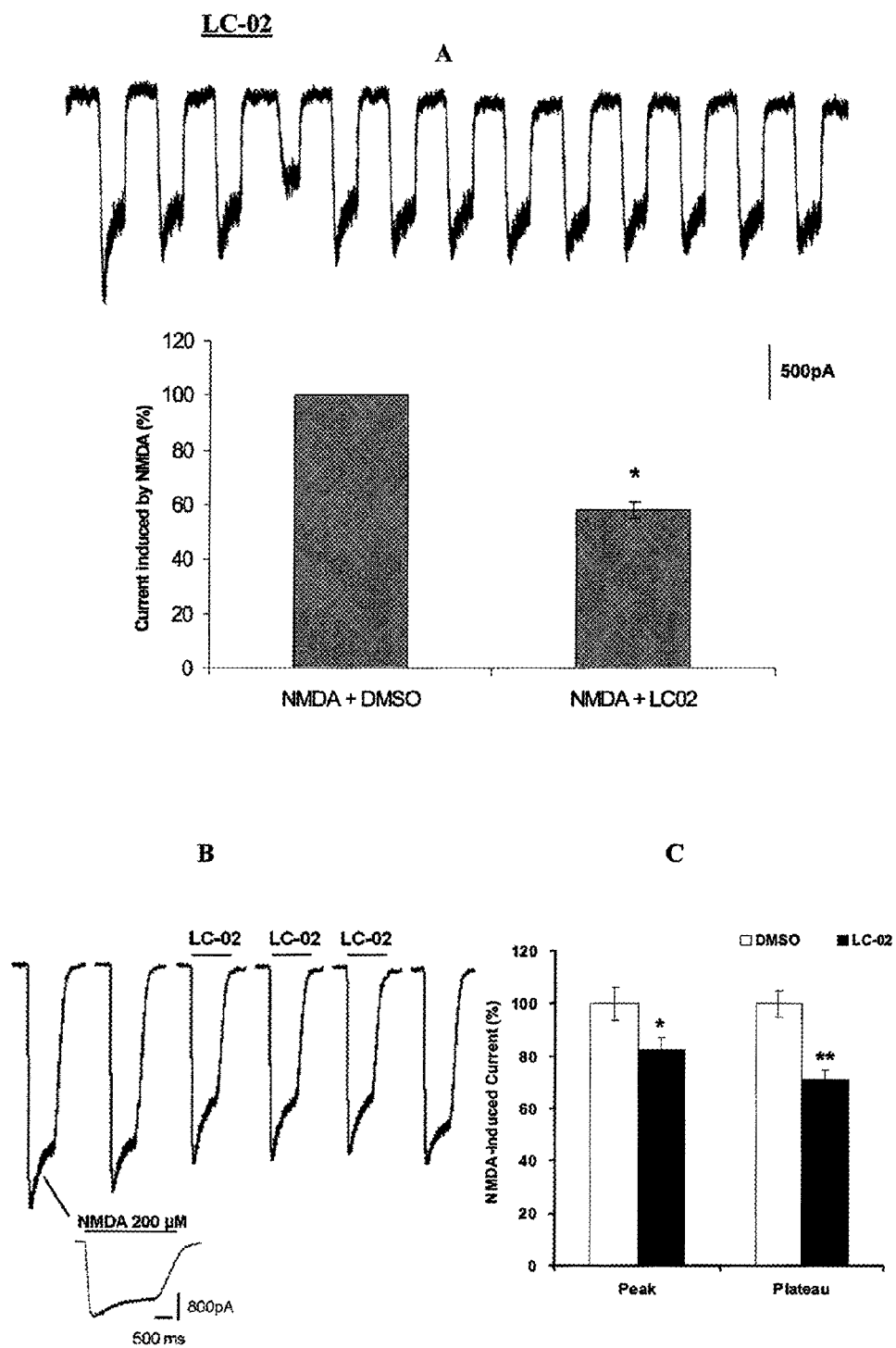
FIG. 1 illustrates that compound LC-02 decreases NMDA induced current in hippocampal neurons. (A) DIV10-14 rat hippocampal neurons were treated with NMDA (50 µM) in the absence or presence of the compound LC-02 (10 µg/mL). Data is presented as of NMDA-induced current. (B) NMDA antagonistic effect of LC-02 on current responses of a single hippocampal neuron. (C) Effects of LC-02 on pooled NMDA current responses.

The present invention is directed to therapeutically active compounds and pharmaceutical compositions as NMDA antagonists, methods of inhibiting over-activation of NMDA receptors, methods of treating and/or preventing neurodegenerative diseases and neuropathological disorders, methods of providing neuroprotection under stress conditions, such as a stroke, and methods of enhancing the brain's cognitive functions in mammals and humans. For example, the present invention provides therapeutic agents and methods for prevention and/or treatment of acute and chronic disorders of the CNS, ranging from neuropathological conditions, such as neuropathic pain, stroke, brain trauma, and epilepsy to neurodegenerative diseases such as amyotrophic lateral sclerosis (ALS), Alzheimer's disease, Parkinson's disease and Huntington's disease. In addition, the present invention provides NMDA antagonists that may be useful in the treatment of nonketotic hyperglycinemia, an autosomal recessive disorder associated with absent or diminished glycine cleavage enzyme activity. Furthermore, the present invention provides neuronal protection against glutamate-induced neurodegeneration and toxicity, and enhances the brain's cognitive functions, such as learning and memory. For instance, compounds (S)-4-(substituted)-5,5-(disubstituted or unsubstituted)-3-(substituted or unsubstituted)-2-(substituted) oxazolidine derivatives are capable of protecting nerve cells and tissues subjected to glutamate-induced stress from damage by blocking the toxic effects of over-activated NMDA receptors.

Advantageously, the present invention provides NMDA antagonists that exhibit reduced side effects. In particular, the present invention provides NMDA antagonists that have unique functionality, for example, the compounds can (i) inhibit NMDA receptor-mediated excitotoxicity; (ii) prevent and/or treat neurodegenerative diseases including amyotrophic lateral sclerosis, Alzheimer's disease, Parkinson's disease and Huntington's disease, and neuropathological conditions; (iii) improve learning and memory in mammals or humans by enhancing long-term potentiation; and (iv) confer neuroprotection under oxidative stress and in stroke-like conditions. As such, the compounds are therapeutically potent over a range of disorders including dementia, neurodegeneration, brain trauma and stroke.

II. Definitions

"A" or "an" entity as used herein refers to one or more of that entity; for example, a compound refers to one or more compounds or at least one compound. As such, the terms "a" (or "an"), "one or more", and "at least one" can be used interchangeably herein.

"About" as used herein refers to variation one might see in measurements taken among different instruments, samples, and sample preparations.

As used herein, the term "alkyl" refers to a straight or branched, saturated, aliphatic radical having the number of carbon atoms indicated (i.e. $C_{1-8}$ or $C_1$-$C_8$ means one to eight carbons. For example, $C_1$-$C_6$ alkyl includes, but is not limited to, methyl, ethyl, propyl, isopropyl, butyl, pentyl, hexyl, isopropyl, iso-butyl, sec-butyl, tert-butyl, etc. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms. For example, $C_{1-8}$alkyl refers to a hydrocarbon radical straight or branched having 1, 2, 3, 4, 5, 6, 7 or 8 carbon atoms and includes, but are not limited to, $C_{1-2}$alkyl, $C_{1-4}$ alkyl, $C_{2-6}$ alkyl, $C_{2-4}$ alkyl, $C_{1-6}$ alkyl, $C_{2-8}$alkyl, $C_{1-7}$alkyl, $C_{2-7}$alkyl and $C_{3-8}$ alkyl.

As used herein, the term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention.

As used herein, the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

As used herein, the term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl.

As used herein, the term "cycloalkyl-alkyl" refers to a radical —R'R", where R' is an alkylene group (having the indicated number of carbon atoms, or if unspecified having six or fewer main chain carbon atoms) and R" is a cycloalkyl group as defined herein. Examples of cycloalkylalkyl include cyclohexylmethyl, pentylethyl and the like.

As used herein, the term "aryl" refers to, unless otherwise stated, a polyunsaturated, typically aromatic, hydrocarbon group which can be a single ring or multiple rings (up to three rings, one or more of which is optionally a cycloalkyl or heterocycloalkyl) which are fused together or linked covalently. Non-limiting examples of aryl groups include phenyl, naphthyl and biphenyl.

As used herein the term "arylalkyl" refers to a radical —R'R", where R' is an alkylene group (having the indicated number of carbon atoms, or if unspecified having six or fewer main chain carbon atoms) and R" is an aryl group as defined herein. Examples of arylalkyl include benzyl, phenethyl and the like.

As used herein, the term "heteroalkyl," by itself or in combination with another term, refers to, unless otherwise stated, a stable straight or branched chain, or combinations thereof, consisting of the stated number of carbon atoms and from one to three heteroatoms selected from the group consisting of O, N, Si, for example, Si, S, —N, —N—, —N=, —O, —O—, O=, —S—, —SO— and —S(O)$_2$—, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

As used herein, the term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycylic ring system. The heterocycloalkyl can also be a heterocyclic alkyl ring fused with an aryl or a heteroaryl ring. Non-limiting examples of heterocycloalkyl groups include pyrrolidinyl, piperidinyl, imidazolidinyl, pyrazolidinyl, butyrolactam, valerolactam, imidazolidinone, hydantoin, dioxolane, phthalimide, piperidine, 1,4-dioxanyl, morpholinyl, thiomorpholinyl, thiomorpholinyl-5-oxide, piperazinyl, pyranyl, thiopyranyl, pyrone, tetrahydrofuranyl, tetrahydrothiophenyl, quinuclidinyl, and the like. A heterocycloalkyl group can be attached to the remainder of the molecule through a ring carbon or a heteroatom.

As used herein, the term "heterocycloalkylalkyl" refers to a radical —R'R", where R' is an alkylene group (having the indicated number of carbon atoms, or if unspecified having six or fewer main chain carbon atoms) and R" is a heterocycloalkyl group as defined herein. Examples of heterocycloalkylalkyl include piperidinylmethyl, tetrahydrofuranylethyl and the like.

As used herein the term "heterocyclic" or "heterocyclyl" refers to a saturated or unsaturated non-aromatic cyclic radical of 3 to 8 ring atoms in which one or two ring atoms are heteroatoms selected from O, NR (where R is independently hydrogen or alkyl) or S(O)$_n$ (where n is an integer from 0 to 2), the remaining ring atoms being C, where one or two C atoms may optionally be replaced by a carbonyl group. Examples of heterocyclyl include, but is not limited to, tetrahydropyranyl, piperidino, N-methylpiperidin-3-yl, piperazino, N-methylpyrrolidin-3-yl, 3-pyrrolidino, 3-pyrrolinyl, 2-pyrrolidon-1-yl, morpholino, thiomorpholino, thiomorpholino-1-oxide, thiomorpholino-1,1-dioxide, pyrrolidinyl, and the like.

As used herein the term "heterocyclylalkyl" refers to a radical —R'R", where R' is an alkylene group (having the indicated number of carbon atoms, or if unspecified having six or fewer main chain carbon atoms) and R" is a heterocyclyl group as defined herein. Examples of heterocyclylalkyl include piperidinylmethyl, tetrahydrofuranylethyl, pyronylmethyl, 3-pyrrolinylmethyl and the like.

As used herein, the term "heteroaryl" refers to aryl groups (or rings) that contain from one to five heteroatoms deleted from N, O, or S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

As used herein, the term "heteroarylalkyl" refers to a radical —R'R", where R' is an alkylene group (having the indicated number of carbon atoms, or if unspecified having six or fewer main chain carbon atoms) and R" is a heteroaryl group as defined herein. Examples of heteroarylalkyl include pyridylmethyl, pyrazolyethyl, benzoimidazolylmethyl and the like.

As used herein, the terms "halo" or "halogen," by themselves or as part of another substituent, mean, unless otherwise stated, a fluorine, chlorine, bromine, or iodine atom.

As used herein, the term "haloalkyl," refers to monohaloalkyl and polyhaloalkyl. For example, the term "C$_{1-4}$haloalkyl" is meant to include trifluoromethyl, 2,2,2-trifluoroethyl, 4-chlorobutyl, 3-bromopropyl, and the like.

As used herein, substituents for the aryl and heteroaryl groups are varied, unless indicated, and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, unsubstituted aryl and heteroaryl, (unsubstituted aryl)-C$_{1-4}$ alkyl, and unsubstituted aryloxy-C$_{1-4}$ alkyl.

As used herein, the term "protecting group" or "protected form thereof" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996), each of which is incorporated herein by reference. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also, Boyle, A. L. (Editor), CURRENT PROTOCOLS IN NUCLEIC ACID CHEMISTRY, John Wiley and Sons, New York, Volume 1, 2000).

The term "labile protecting group" refers to those protecting groups that are removeable under mild conditions that do not significantly impact the remainder of the molecule.

The term "composition" as used herein is intended to encompass a product comprising the specified ingredients in the specified amounts, as well as any product which results, directly or indirectly, from combination of the specified ingredients in the specified amounts.

The term "prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Other examples of prodrugs include compounds that comprise —NO, —NO$_2$, —ONO, or —ONO$_2$ moieties.

Disease states that can be treated using the compounds of the invention to inhibit NMDA receptor activity and protect against glutamate induced neurotoxicity include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, stroke, hydrocephalus, subarachnoid hemorrhage, vascular insufficiency, brain tumor, epilepsy, Parkinson's disease, cerebral microangiopathy, pain medication, chemotherapy, oxygen deprivation, e.g, caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, and fetal alcohol syndrome, for example.

As used herein, the term "neuropathic" pain refers to pain resulting from injury to or chronic changes in peripheral and/or central sensory pathways, where the pain often occurs or persists without an obvious noxious input.

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "hydrate" refers to a compound that is complexed to at least one water molecule. The compounds of the present invention can be complexed with from 1 to 10 water molecules.

As used herein, the term "inhibiting" refers to a compound that partially or fully prohibits or a method of partially or fully prohibiting a specific action or function.

As used herein, the term "patient in need" refers to a patient suffering from the central nervous disorders including neurodegenerative diseases and neuropathological conditions. Non-limiting examples include amyotrophic lateral sclerosis, Parkinson's disease, Alzheimer's disease, Huntington's disease, neuropathic pain, stroke, brain trauma, epilepsy stroke, and dementia. Patients suffering from other conditions treatable with the NMDA antagonists are also treatable with the methods of the present invention. Patients treatable using the methods of the present invention are animals such as mammals, including, but not limited to, primates (e.g., humans), cows, sheep, goats, horses, dogs, cats, rabbits, rats, mice and the like. In certain embodiments, the patient is a human.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington: The Science and Practice of Pharmacy, 21st ed., Lippincott Williams & Wilkins, Easton Pa., 2005, which is incorporated herein by reference. The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, pharmaceutically acceptable salts of the basic compounds of the present invention are salts formed with acids, such as of mineral acids, organic carboxylic and organic sulfonic acids, e.g., hydrochloric acid, methanesulfonic acid, maleic acid, are also possible provided a basic group, such as pyridyl, constitutes part of the structure.

As used herein, "pharmaceutically acceptable" is meant the carrier, diluent or excipient must be compatible with the other ingredients of the formulation and not deleterious to the recipient thereof.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

III. Compounds

In one aspect, the present invention provides a compound of formula (I):

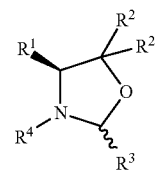

or a pharmaceutically acceptable salt, N-oxide, prodrug, hydrate and isomers thereof.

In formula I, $R^1$ is selected from the group consisting of $(C_1-C_8)$alkyl, $(C_1-C_8)$heteroalkyl, arylalkyl, $(C_3-C_8)$cycloalkyl, $(C_3-C_8)$cycloalkyl-alkyl, $(C_1-C_8)$haloalkyl, heterocycloalkyl, heterocycloalkyl-$(C_1-C_6)$alkyl, heteroaryl-$(C_1-C_6)$alkyl, heterocyclyl-alkyl and aryl.

In one group of embodiments of compounds having formula I, $R^1$ is selected from the group consisting of $(C_1-C_8)$alkyl, $(C_1-C_8)$heteroalkyl, aryl-$(C_1-C_6)$alkyl and heteroaryl-$C_{1-6}$alkyl, each of which is optionally substituted with from 1-3 $R^b$ substituents independently selected from the group consisting of halogen, —OH, —OR$^c$, —OSi(R$^c$)$_3$, —OC(O) O—R$^c$, —OC(O)R$^c$, —OC(O)NHR$^c$, —OC(O)N(R$^c$)$_2$, —SH, —SR$^c$, —S(O)R$^c$, —S(O)$_2$R$^c$, —SO$_2$NH$_2$, —S(O)$_2$NHR$^c$, —S(O)$_2$N(R$^c$)$_2$, —NHS(O)$_2$R$^c$, —NR$^c$S(O)$_2$R$^c$, —C(O)NH$_2$, —C(O)NHR$^c$, —C(O)N(R$^c$)$_2$, —C(O)R$^c$, —C(O)H, —C(=S)R$^c$, —NHC(O)R$^c$, —NR$^c$C(O)R$^c$, —NHC(O)NH$_2$, —NR$^c$C(O)NH$_2$, —NR$^c$C(O)NHR$^c$, —NHC(O)NHR$^c$, —NR$^c$C(O)N(R$^c$)$_2$, —NHC(O)N(R$^c$)$_2$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —NR$^c$S(O) NH$_2$, —NR$^c$S(O)$_2$NHR$^c$, —NH$_2$C(=NR$^c$)NH$_2$, —N=C (NH$_2$)NH$_2$, —C(=NR$^c$)NH$_2$, —N$_3$, —NH—OH, —NR$^c$— OH, —NR$^c$—OR$^c$, —N=C=O, —N=C=S. —Si(R$^c$)$_3$, —NH—NHR$^c$, —NHC(O)NHNH$_2$, —P(O)(OR$^c$)$_2$, —N═C═NR$^c$ and —S—CN, wherein each R$^c$ is independently an alkyl or aryl, wherein R$^c$ is optionally further substituted with from 1-3 substituents selected from the group consisting of halogen, —OH, —OR$^d$, —SH, —SR$^d$, —S(O)$_2$R$^d$, —SO$_2$NH$_2$, —C(O)NH$_2$, —C(O)NHR$^d$, —C(O)N(R$^d$)$_2$, —C(O)R$^d$, —C(O)H, —NHC(O)R$^d$, —NR$^d$C(O)R$^d$, —CO$_2$H, —CO$_2$R$^d$, —R$^d$, —CN, —NO$_2$, —NH$_2$, —NHR$^d$, —N(R$^d$)$_2$, —NH—OH, —NR$^d$—OH, —NR$^d$—OR$^d$, —N═C═O, —N═C═S, —NH—NHR$^d$ and —S—CN, wherein each R$^d$ is independently an (C$_1$-C$_6$)alkyl. In certain instances, R$^1$ is selected from (C$_1$-C$_8$)alkyl, phenyl-(C$_1$-C$_6$)alkyl and 5- or 6-membered heteroaryl-C$_{1-6}$alkyl, each of which is optionally substituted with from 1-3 R$^b$. In certain occurrences, R$^b$ is selected from the group consisting of halogen, —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —S(O)R$^c$, —S(O)$_2$R$^c$, —C(O)N(R$^c$)$_2$, —C(O)R$^c$, —C(O)H, —C(═S)R$^c$, —NHC(O)R$^c$, —NR$^c$C(O)R$^c$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —N$_3$, —NH—OH, —NR$^c$—OH and —NR$^c$—OR$^c$. In certain other instances, R$^1$ is selected from the group consisting of (C$_1$-C$_8$)alkyl, phenyl-(C$_1$-C$_6$)alkyl and 5-membered heteroaryl-C$_{1-6}$alkyl, wherein the heteroaryl is optionally fused with a 5- or 6-membered aromatic ring having from 0-2 additional heteroatoms selected from N, O or S. In some occurrences, R$^1$ is selected from (C$_1$-C$_8$) alkyl, phenyl-(C$_1$-C$_6$)alkyl, imidazoly-C$_1$-C$_6$alkyl, pyrazolyl-(C$_1$-C$_6$)alkyl, oxazoly-(C$_1$-C$_6$)alkyl, isoxazoyl-(C$_1$-C$_6$)alkyl, thiazolyl-(C$_1$-C$_6$)alkyl, isothiazoly-(C$_1$-C$_6$)alkyl, furanyl-(C$_1$-C$_6$)alkyl, indolyl-(C$_1$-C$_6$)alkyl and thiophenyl-(C$_1$-C$_6$)alkyl. In certain instances, the substitutions for R$^1$ to R$^4$ groups by R$^b$ are on the aromatic portion of the R$^1$-R$^4$ groups, wherein the aromatic portion of each of R$^1$-R$^4$ groups is optionally substituted with from 1-3 R$^b$ groups.

In another group of embodiments, R$^1$ is selected from the group consisting of -Me, —CH$_2$(Me)$_2$, —CH$_2$CH(Me)$_2$, —CHMe(Et), —CH$_2$CH$_2$CH$_3$, —CH$_2$Ph, —CH$_2$PhOH, —CH$_2$CH$_2$CH$_2$CH$_2$NH$_2$, —CH$_2$CH$_2$CONH$_2$, -Ph, -MePh, -PhNO$_2$, -PhOCH$_3$, -PhNH$_2$, -PhF, -PhBr, -PhI, PhCN, -Ph-COOR$^c$, -Ph-OCOR$^c$, -PhNHCOR$^c$, -Ph-COOH, —CH$_2$CO$_2$H, —CH$_2$CH$_2$COOH, —CH$_2$CONH$_2$, —CH$_2$OH, —CH(OH)CH$_3$, indolyl-CH$_2$—, indol-3-yl-methyl, —(CH$_2$)$_3$NHC(═NH)NH$_2$, —CH$_2$CH$_2$CHNHCH(NH$_2$)$_2$, imidazolyl-CH$_2$—, imidazol-4-yl-CH$_2$—, imidazol-5-yl-CH$_2$—, CH$_2$CH$_2$SMe and —CH$_2$SH. In certain instances, R$^1$ is a side chain of a naturally occurring amino acid. In certain other instances, R$^1$ is selected from the group consisting of —CH$_2$CH(Me)$_2$, CH$_3$CH$_2$(CH$_3$)CH—, benzyl, imidazoly-CH$_2$— or imidazol-5-yl-CH$_2$—. In some embodiments, R$^1$ is isobutyl, benzyl or 2-butyl.

In formula I, R$^2$ is selected from the group consisting of —H, (C$_1$-C$_8$)alkyl, (C$_1$-C$_8$)heteroalkyl, heteroaryl-alkyl and aryl, wherein the (C$_1$-C$_8$)alkyl, (C$_1$-C$_8$)heteroalkyl, heteroaryl-alkyl and aryl groups are each optionally substituted with from 1-3 R$^b$ substituents. In certain instances, the aromatic portion of R$^2$ is optionally substituted with from 1-3 R$^b$ substituents.

In a group of embodiments of compounds having formula I, R$^2$ is selected from the group consisting of —H, (C$_1$-C$_8$) alkyl and aryl, wherein the alkyl and aryl are optionally substituted with from 1-3 R$^b$. In certain instances, R$^2$ is selected from the group consisting of —H, (C$_1$-C$_8$)alkyl and phenyl, wherein the alkyl and/or phenyl are optionally substituted with from 1-3 R$^b$ substituents selected from the group consisting of —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —S(O)R$^c$, —S(O)$_2$R$^c$, —C(O)N(R$^c$)$_2$, —C(O)R$^c$, —C(O)H, —C(═S)R$^c$, —NHC(O)R$^c$, —NR$^c$C(O)R$^c$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —N$_3$, —NH—OH, —NR$^c$—OH and —NR$^c$—OR$^c$. In some occurrences, R$^b$ is selected from the group consisting of halogen, —OH, —OR$^c$, —R$^c$, —CN, —NO$_2$, —NH$_2$, —NHR$^c$ and —N(R$^c$)$_2$.

In certain other instances, R$^2$ is selected from the group consisting of —H, -Me, -Et, —Pr, -Bu, i-Pr, t-Bu, i-Bu, —CH$_2$CH$_2$CH$_2$CH$_2$CH$_3$, -Ph, -PhMe, 4-methylphenyl, 3-methylphenyl, 2-methylphenyl, -PhNO$_2$, -PhOMe, -PhNH$_2$, -Ph-F, -Ph-Br, -Ph-Cl, -Ph-I, -PhCN, -Ph-COOR$^c$, -Ph-OCOR$^c$, -PhNHCOR$^c$ and -Ph-COOH. In certain instances, R$^2$ is —H, ethyl, n-propyl or Bu. In some instances, R$^2$ is ethyl or n-propyl.

In formula I, R$^3$ is selected from the group consisting of —H, (C$_1$-C$_8$)alkyl, (C$_1$-C$_8$)heteroalkyl, heteroaryl-alkyl and aryl, where the (C$_1$-C$_8$)alkyl, (C$_1$-C$_8$)heteroalkyl, heteroaryl-alkyl and aryl groups are each optionally substituted with from 1-3 R$^b$ substituents. In certain instances, the aromatic portions of R$^3$ are optionally substituted with from 1-3 R$^b$ substituents.

In a group of embodiments of compounds having formula I, R$^3$ is selected from the group consisting of —H, (C$_1$-C$_8$) alkyl and aryl, wherein the alkyl and/or aryl are optionally substituted with from 1-3 R$^b$. In certain instances, R$^3$ is selected from the group consisting of —H, (C$_1$-C$_8$)alkyl and phenyl, wherein the alkyl and phenyl are optionally substituted with from 1-3 R$^b$ substituents selected from the group consisting of —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —SR$^c$, —S(O)R$^c$, —S(O)$_2$R$^c$, —C(O)N(R$^c$)$_2$, —C(O)R$^c$, —C(O)H, —C(═S)R$^c$, —NHC(O)R$^c$, —NR$^c$C(O)R$^c$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —N$_3$, —NH—OH, —NR$^c$—OH and —NR$^c$—OR$^c$. In some occurrences, R$^b$ is selected from the group consisting of halogen, —OH, —OR$^c$, —R$^c$, —CN, —NO$_2$, —NH$_2$, —NHR$^c$ and —N(R$^c$)$_2$.

In certain other instances, R$^3$ is selected from the group consisting of —H, -Me, -Et, —Pr, -Bu, -iPr, -tBu, -iBu, —CH$_2$CH$_2$CH$_2$CH$_2$CH$_3$, -Ph, -PhMe, 4-methylphenyl, 3-methylphenyl, 2-methylphenyl, -PhNO$_2$, -PhOMe, -PhNH$_2$, -Ph-F, -Ph-Br, -Ph-Cl, -Ph-I, -PhCN, -Ph-COOR$^c$, -Ph-OCOR$^c$, -PhNHCOR$^c$ and -Ph-COOH. In one occurrence, R$^3$ is ethyl, n-propyl, butyl or -phenyl. In some instances, R$^3$ is butyl, pentyl, 3-methylphenyl or 4-methylphenyl.

In another embodiment, R$^3$ is —H.

In formula I, R$^4$ is selected from the group consisting of —H, (C$_1$-C$_8$)alkyl, (C$_1$-C$_8$)heteroalkyl, arylalkyl, (C$_3$-C$_8$)cycloalkyl, (C$_3$-C$_8$)cycloalkyl-alkyl, —X$^1$S(O)R$^a$, —X$^1$S(O)$_2$R$^a$, —X$^1$SO$_2$NH$_2$, —X$^1$S(O)$_2$NHR$^a$, —X$^1$S(O)$_2$N(R$^a$)$_2$, —X$^1$C(O)NH$_2$, —X$^1$C(O)NHR$^a$, —X$^1$C(O)N(R$^a$)$_2$, —X$^1$C(O)R$^a$, —X$^1$C(O)H, —X$^1$C(═S)R$^a$, —X$^1$CO$_2$H, —X$^1$CO$_2$R$^a$, —X$^1$P(O)(OR$^a$)$_2$ and an amino protecting group; wherein R$^a$ is (C$_1$-C$_8$)alkyl or aryl and each X$^1$ is independently a bond or an (C$_1$-C$_4$)alkylene, where the aliphatic and/or aromatic portions of R$^4$ group is further substituted with from 1-3 R$^b$ substituents.

In a group of embodiments, R$^4$ is selected from the group consisting of —H, aryl-(C$_1$-C$_6$)alkyl, (C$_1$-C$_8$)alkyl, (C$_1$-C$_8$) heteroalkyl, —C(O)NH$_2$, —C(O)NHR$^a$, —C(O)N(R$^a$)$_2$, —C(O)R$^a$, —C(O)H, —C(═S)R$^a$, —CO$_2$H, —CO$_2$R$^a$, —P(O)(OR$^a$)$_2$ and an amino protecting group, wherein the aliphatic and/or aromatic portion of the R$^4$ group are optionally substituted with from 1-3 $R^b$ substituents. In certain instances, $R^4$ is selected from the group consisting of —H, phenyl-($C_1$-$C_6$)alkyl, ($C_1$-$C_8$)alkyl, —C(O)NH$_2$, —C(O)NHR$^a$, —C(O)N(R$^a$)$_2$, —C(O)R$^a$, —C(O)H, —C(=S)R$^a$, —CO$_2$H, —CO$_2$R$^a$ and an amino protecting group, wherein $R^a$ is alkyl or phenyl optionally substituted with from 1-3 $R^b$ groups. Suitable amino protecting group include, but are not limited to, those found in T. W. Greene and P. G. Wuts, PROTECTIVE GROUPS IN ORGANIC CHEMISTRY, (Wiley, 4th ed. 2006). In certain other instances, $R^4$ is selected from the group consisting of —H, —CHO, PhCO—, PhNHCO—, PhOCO—, CH$_3$NHCO—, CH$_3$OCO—, CH$_3$CO—, EtCO—, -Me, -Et, —Pr, -Bu, iPr, iBu, -tBu, —CH$_2$CH$_2$CH$_2$CH$_3$ and t-BuO—CO—. In some occurrences, $R^4$ is —H, ethyl, n-propyl, —C(O)Ph, —C(O)CH$_3$, —C(O)CH$_2$CH$_3$ or Boc. In one embodiment, $R^4$ is —H.

In another embodiment, $R^1$ and $R^4$ together with the atoms to which they are attached form a 5- or 6-membered heterocyclic ring having from 0-2 additional heteroatoms as ring members selected from O or N, optionally the heterocyclic ring is substituted with from 1-3 $C_{1-6}$alkyl substituents. In certain instances, $R^1$ and $R^4$ together with the atoms to which they are attached for a 5-membered heterocyclic ring having from 0-2 additional heteroatoms as ring members selected from O or N, optionally substituted with from 1-3 $C_{1-6}$alkyl substituents. In one occurrence, $R^1$ and $R^4$ together with the atoms to which they are attached for a 5-membered pyrrolidine ring containing 0-1 additional heteroatom selected from N or O, optionally substituted with from 1-3 $C_{1-6}$alkyl substituents.

In formula I, the wavy line denoted by ～ indicates the carbon to which the wavy line is attached has a stereoconfiguration of R, S or a mixture (racemic) thereof. In one embodiment, the carbon attached to the wavy line has a stereoconfiguration of R. In another embodiment, the carbon attached to the wavy line has a stereoconfiguration of S. In yet another embodiment, the carbon attached to the wavy line has a racemic stereoconfiguration, i.e. 50% R and 50% S.

Subformulae of Formula I

In one group of embodiments, compounds of formula I have subformula Ia:

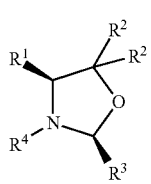

Ia wherein $R^3$ is selected from the group consisting of ($C_1$-$C_8$) alkyl, ($C_1$-$C_8$)heteroalkyl, heteroaryl-alkyl and aryl. $R^1$, $R^2$, $R^3$ and $R^4$ are as defined in any of the above formulas and embodiments. In one instance, $R^1$ is (CH$_3$)$_2$CHCH$_2$—. In another instance, $R^1$ is isobutyl. In yet another instance, $R^1$ is benzyl.

In some embodiments of the compounds having formula (Ia), $R^4$ is —H; $R^1$ is 2-butyl, isobutyl or benzyl; $R^2$ is ethyl or n-propyl; and $R^3$ is butyl, pentyl, 2-methylphenyl, 3-methylphenyl, 4-methylphenyl.

In another group of embodiments, compounds of formula I have subformula Ib:

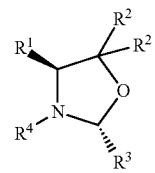

Ib wherein $R^3$ is selected from the group consisting of ($C_1$-$C_8$) alkyl, ($C_1$-$C_8$)heteroalkyl, heteroaryl-alkyl and aryl. $R^1$, $R^2$, $R^3$ and $R^4$ are as defined in any of the above formulas and embodiments. In one instance, $R^1$ is (CH$_3$)$_2$CHCH$_2$—. In another instance, $R^1$ is isobutyl. In yet another instance, $R^1$ is benzyl.

In yet another group of embodiments, compounds of formula I have subformula Ic:

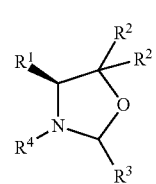

Ic wherein $R^3$ is selected from the group consisting of ($C_1$-$C_8$) alkyl, ($C_1$-$C_8$)heteroalkyl, heteroaryl-alkyl and aryl and the carbon center to which $R^3$ is attached has a racemic stereoconfiguration. $R^1$, $R^2$, $R^3$ and $R^4$ are as defined in any of the above formulas and embodiments. In one instance, $R^1$ is (CH$_3$)$_2$CHCH$_2$—. In another instance, $R^1$ is isobutyl. In yet another instance, $R^1$ is benzyl.

In one group of embodiments, compounds of formula I having a subformula selected from the group consisting of:

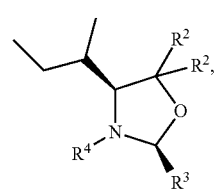

Ia-1

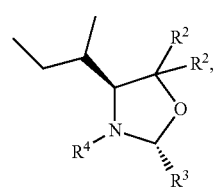

Ib-1

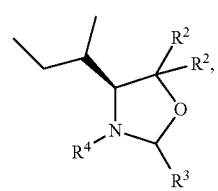

Ic-1

-continued

Ia-2 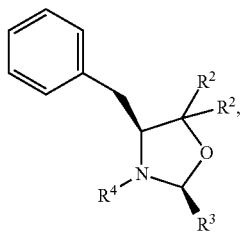

Ib-2 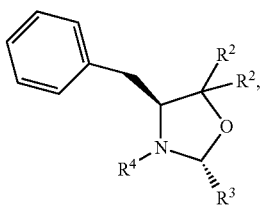

Ic-2 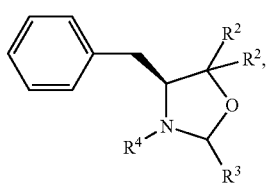

Ia-3 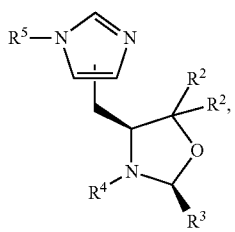

Ib-3 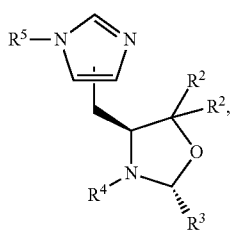

Ic-3 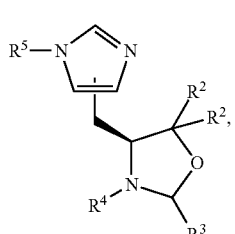

Ia-4 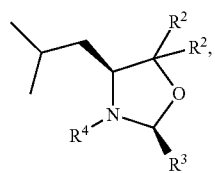

-continued

Ib-4 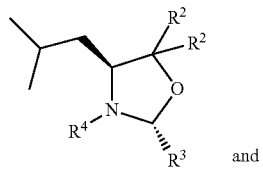

and

Ic-4 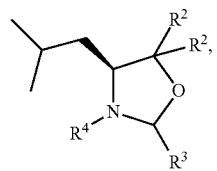

wherein $R^5$ is selected from the group consisting of —H, $(C_1$-$C_8)$alkyl, $(C_1$-$C_8)$heteroalkyl, arylalkyl, $(C_3$-$C_8)$cycloalkyl, $(C_3$-$C_8)$cycloalkyl-alkyl, —$X^1S(O)R^a$, —$X^1S(O)_2R^a$, —$X^1SO_2NH_2$, —$X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group. In certain instances, $R^4$ is —H, $C_{1-6}$alkyl, —C(O)$C_{1-6}$alkyl or —C(O)-aryl. In one occurrence, $R^4$ is —C(O)Ph, optionally substituted with from 1-3 $R^c$. In another occurrence, $R^2$ and $R^3$ are each independently a $C_{1-8}$alkyl. The substituents $R^1$, $R^2$, $R^3$, $R^4$, $X^1$, $R^a$ and $R^c$ are as defined in any of the above formulas and embodiments.

In another group of embodiments, compounds of formula I is selected from the group consisting of:

Ia-3' 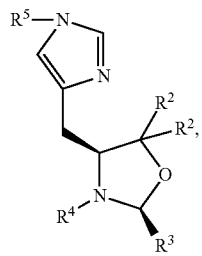

Ib-3' 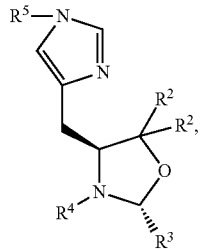

Ic-3' 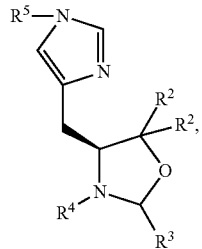

wherein $R^5$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, —$X^1S(O)R^a$, —$X^1S(O)_2R^a$, —$X^1SO_2NH_2$, —$X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group. In certain instances, $R^4$ is —H, $C_{1-6}$alkyl, —$C(O)C_{1-6}$alkyl or —$C(O)$-aryl. In one occurrence, $R^4$ is —$C(O)Ph$, optionally substituted with from 1-3 $R^c$. In another occurrence, $R^2$ and $R^3$ are each independently a $C_{1-8}$alkyl. The substituents $R^1$, $R^2$, $R^3$, $R^4$, $X^1$, $R^a$ and $R^c$ are as defined in any of the above formulas and embodiments.

In one group of embodiments of the compounds having formulae Ia-1, Ia-2, Ia-3, Ia-3', Ib-1, Ib-2, Ib-3, Ib-3', Ic-1, Ic-2, Ic-3 or Ic-3', $R^2$ is $(C_1-C_8)$alkyl, $R^3$ is $(C_1-C_8)$alkyl or optionally substituted aryl and $R^4$ is —H or —$COR^a$. In one instance, $R^3$ is $(C_1-C_8)$alkyl. In another instance, $R^3$ is optionally substituted aryl, such as optionally substituted phenyl. In yet another instance, $R^4$ is —H or —$COR^a$. For example, $R^a$ is optionally substituted phenyl, —$CH_3$, —$CH_2CH_3$ or Ph.

In another group of embodiments of the compounds having formulae Ia-1, Ia-2, Ia-3, Ia-3', Ib-1, Ib-2, Ib-3, Ib-3', Ic-1, Ic-2, Ic-3 or Ic-3', $R^4$ is $(C_1-C_8)$alkyl, $R^2$ is $(C_1-C_8)$alkyl or optionally substituted aryl and $R^3$ is $(C_1-C_8)$alkyl or optionally substituted aryl. In certain instances, $R^4$ is $(C_1-C_8)$alkyl, $R^2$ is $(C_1-C_8)$alkyl and $R^3$ is $(C_1-C_8)$alkyl or optionally substituted aryl, such as optionally substituted phenyl. In certain other instances, $R^4$ is $(C_1-C_8)$alkyl and $R^2$ and $R^3$ are each independently optionally substituted aryl, such as substituted phenyl.

In some embodiments of the compounds having formulas Ia-1, Ia-2, Ia-3, Ia-3', Ib-1, Ib-2, Ib-3, Ib-3', Ic-1, Ic-2, Ic-3 or Ic-3', $R^4$ is —H. In other embodiments of the compounds having formulas Ia-1, Ia-2, Ia-3, Ia-3', Ib-1, Ib-2, Ib-3, Ib-3', Ic-1, Ic-2, Ic-3 or Ic-3' and within the above embodiments, $R^2$ is ethyl or n-propyl. In yet other embodiments of compounds having formulas Ia-1, Ia-2, Ia-3, Ia-3', Ib-1, Ib-2, Ib-3, Ib-3', Ic-1, Ic-2, Ic-3 or Ic-3' and within the above embodiments, $R^3$ is $C_1-C_6$ alkyl, butyl, pentyl, 3-methylphenyl, 3-methylphenyl or 4-methylphenyl. In still other embodiments of compounds having formulas Ia-1, Ia-2, Ia-3, Ia-3', Ib-1, Ib-2, Ib-3, Ib-3', Ic-1, Ic-2, Ic-3 or Ic-3' and within the above embodiments, $R^1$ is $C_1-C_6$alkyl, 2-butyl, isobutyl or benzyl.

A family of specific compounds of particular interest having formula I includes compounds, pharmaceutically acceptable salts, prodrugs, hydrates, solvates and isomers thereof are set forth in Tables 1, 2 and 3.

TABLE 1

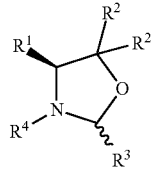

Selected chiral oxazolidine derivatives of formula I

| Compound No. | Structure | Molecular Formula | Molecular Weight | Solvent |
| --- | --- | --- | --- | --- |
| LC-1 | 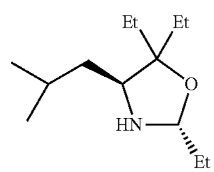 | $C_{13}H_{27}NO$ | 213 | $CHCl_3$ |
| LC-2 | 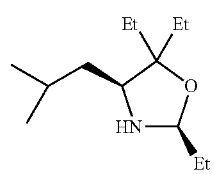 | $C_{13}H_{27}NO$ | 213 | $CHCl_3$ |
| LC-3 | 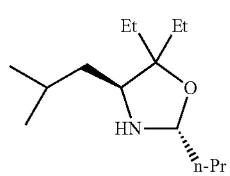 | $C_{14}H_{29}NO$ | 227 | $CHCl_3$ |
| LC-4 | 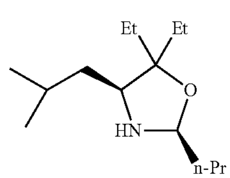 | $C_{14}H_{29}NO$ | 227 | $CHCl_3$ |

TABLE 1-continued

Selected chiral oxazolidine derivatives of formula I

| Compound No. | Structure | Molecular Formula | Molecular Weight | Solvent |
|---|---|---|---|---|
| LC-5 | 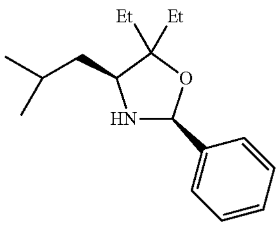 [SMILES: CCC1(CC)O[C@@H](c2ccccc2)N[C@H]1CC(C)C] | $C_{17}H_{27}NO$ | 261 | $CHCl_3$ |
| LC-6 | 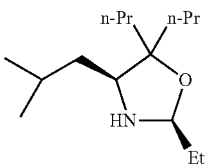 | $C_{15}H_{31}NO$ | 241 | $CHCl_3$ |
| LC-7 | 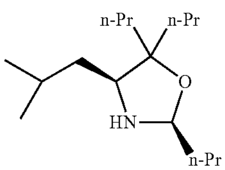 | $C_{16}H_{33}NO$ | 255 | $CHCl_3$ |
| LC-8 | 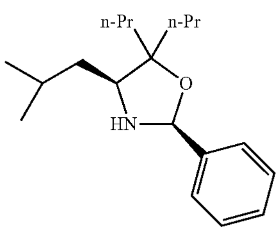 | $C_{19}H_{31}NO$ | 289 | $CHCl_3$ |
| LC-9 | 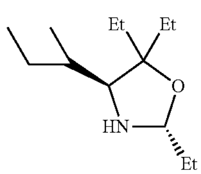 | $C_{13}H_{27}NO$ | 213 | $CHCl_3$ |
| LC-10 | 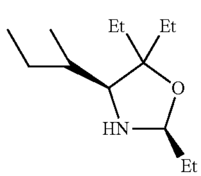 | $C_{13}H_{27}NO$ | 213 | $CHCl_3$ |
| LC-11 | 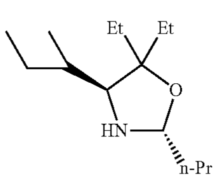 | $C_{14}H_{29}NO$ | 227 | $CHCl_3$ |

TABLE 1-continued
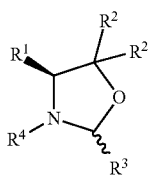
Selected chiral oxazolidine derivatives of formula I
| Compound No. | Structure | Molecular Formula | Molecular Weight | Solvent |
|---|---|---|---|---|
| LC-12 | 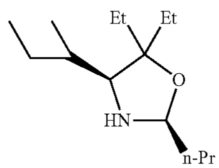 | $C_{14}H_{29}NO$ | 227 | $CHCl_3$ |
| LC-13 | 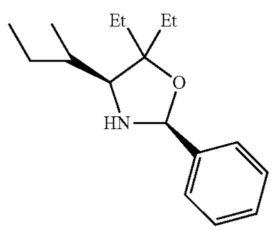 [SMILES: CCC(C)[C@@H]1N[C@H](c2ccccc2)OC1(CC)CC] | $C_{17}H_{27}NO$ | 261 | $CHCl_3$ |
| LC-14 | 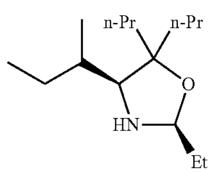 | $C_{15}H_{31}NO$ | 241 | $CHCl_3$ |
| LC-15 | 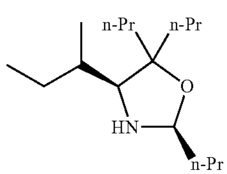 | $C_{16}H_{33}NO$ | 255 | $CHCl_3$ |
| LC-16 | 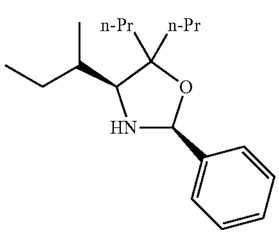 | $C_{19}H_{31}NO$ | 289 | $CHCl_3$ |
| LC-17 | 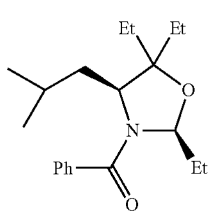 [SMILES: CC[C@@H]1OC(CC)(CC)[C@H](CC(C)C)N1C(=O)c1ccccc1] | $C_{20}H_{31}NO_2$ | 317 | $CHCl_3$ |

TABLE 1-continued

Selected chiral oxazolidine derivatives of formula I

| Compound No. | Structure | Molecular Formula | Molecular Weight | Solvent |
|---|---|---|---|---|
| LC-18 | 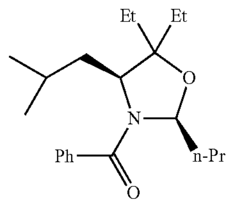 | $C_{21}H_{33}NO_2$ | 331 | $CHCl_3$ |
| LC-19 | 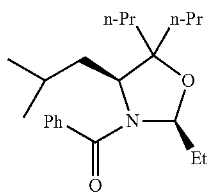 | $C_{22}H_{35}NO_2$ | 345 | $CHCl_3$ |
| LC-20 | 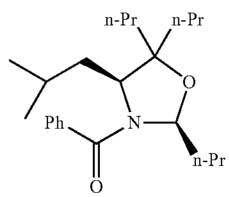 | $C_{23}H_{37}NO_2$ | 359 | $CHCl_3$ |
| LC-21 | 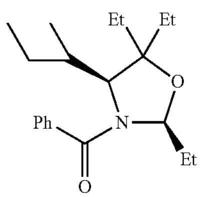 [SMILES: CCC(C)[C@@H]1N(C(=O)c2ccccc2)[C@H](CC)OC1(CC)CC] | $C_{20}H_{31}NO_2$ | 317 | $CHCl_3$ |
| LC-22 | 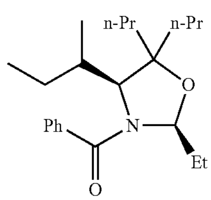 | $C_{22}H_{35}NO_2$ | 345 | $CHCl_3$ |
| LC-23 | 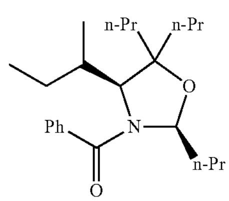 | $C_{23}H_{37}NO_2$ | 359 | $CHCl_3$ |
| LC-24 | 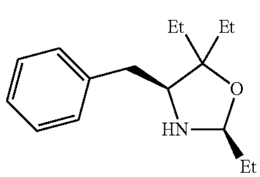 [SMILES: CC[C@H]1N[C@@H](Cc2ccccc2)C(CC)(CC)O1] | $C_{16}H_{25}NO$ | 247 | $CHCl_3$ |

TABLE 1-continued
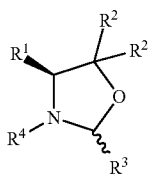
Selected chiral oxazolidine derivatives of formula I
| Compound No. | Structure | Molecular Formula | Molecular Weight | Solvent |
|---|---|---|---|---|
| LC-25 | 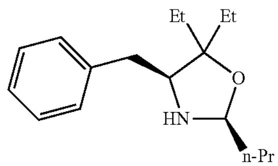 | $C_{17}H_{27}NO$ | 261 | $CHCl_3$ |
| LC-26 | 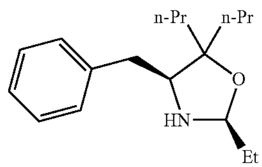 | $C_{18}H_{29}NO$ | 275 | $CHCl_3$ |
| LC-27 | 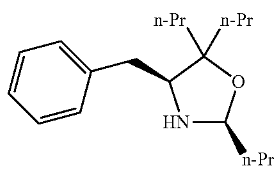 | $C_{19}H_{31}NO$ | 289 | $CHCl_3$ |
| LC-28 | 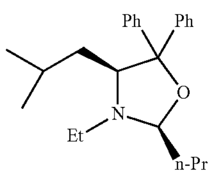 | $C_{24}H_{33}NO$ | 351 | $CHCl_3$ |
| LC-29 | 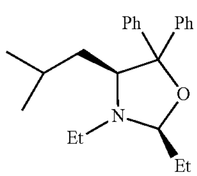 [SMILES: CC[C@@H]1OC(c2ccccc2)(c2ccccc2)[C@H](CC(C)C)N1CC] | $C_{23}H_{31}NO$ | 337 | $CHCl_3$ |
| LC-30 | 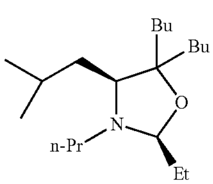 | $C_{20}H_{41}NO$ | 311 | $CHCl_3$ |
| LC-31 | 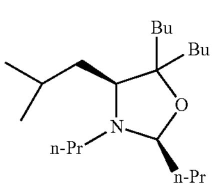 | $C_{21}H_{43}NO$ | 325 | $CHCl_3$ |

TABLE 1-continued
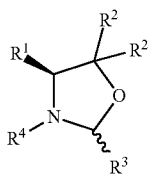
Selected chiral oxazolidine derivatives of formula I
| Compound No. | Structure | Molecular Formula | Molecular Weight | Solvent |
| --- | --- | --- | --- | --- |
| LC-32 | 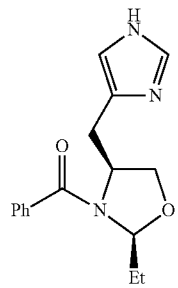 [SMILES: CC[C@@H]1OC[C@H](Cc2c[nH]cn2)N1C(=O)c1ccccc1] | $C_{16}H_{19}N_3O_2$ | 285 | DMSO |
| LC-33 | 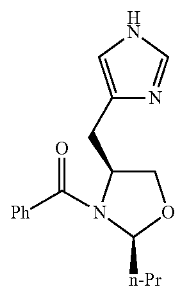 | $C_{17}H_{21}N_3O_2$ | 299 | DMSO |
| LC-34 | 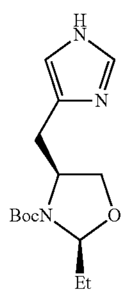 [SMILES: CC[C@@H]1OC[C@H](Cc2c[nH]cn2)N1C(=O)OC(C)(C)C] | $C_{14}H_{23}N_3O_3$ | 281 | DMSO |
| LC-35 | 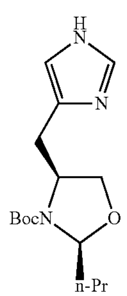 | $C_{15}H_{25}N_3O_3$ | 295 | DMSO |

TABLE 1-continued

Selected chiral oxazolidine derivatives of formula I

| Compound No. | Structure | Molecular Formula | Molecular Weight | Solvent |
| --- | --- | --- | --- | --- |
| LC-36 | 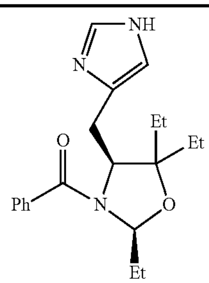 | $C_{20}H_{27}N_3O_2$ | 341 | DMSO |
| LC-37 | 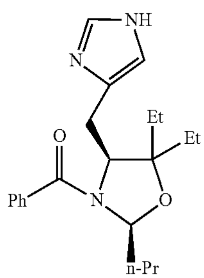 | $C_{21}H_{29}N_3O_2$ | 355 | DMSO |
| LC-38 | 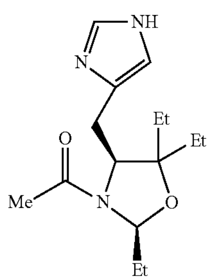 [SMILES: CC[C@@H]1OC(CC)(CC)[C@H](Cc2c[nH]cn2)N1C(C)=O] | $C_{15}H_{25}N_3O_2$ | 279 | DMSO |
| LC-39 | 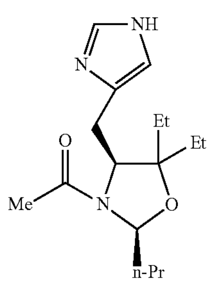 | $C_{16}H_{27}N_3O_2$ | 293 | DMSO |
| LC-40 | 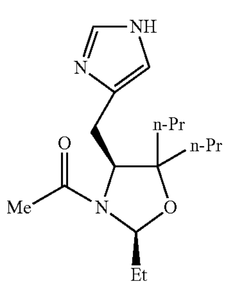 | $C_{17}H_{29}N_3O_2$ | 307 | DMSO |

TABLE 1-continued

Selected chiral oxazolidine derivatives of formula I

| Compound No. | Structure | Molecular Formula | Molecular Weight | Solvent |
|---|---|---|---|---|
| LC-41 | 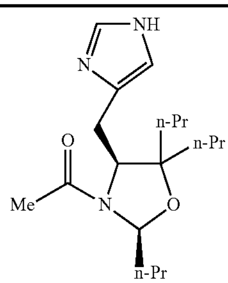 | $C_{18}H_{31}N_3O_2$ | 321 | DMSO |
| LC-42 | 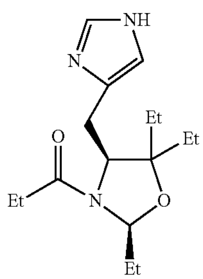 [SMILES: CCC(=O)N1[C@H](CC)OC(CC)(CC)[C@@H]1Cc1c[nH]cn1] | $C_{16}H_{27}N_3O_2$ | 293 | DMSO |
| LC-43 | 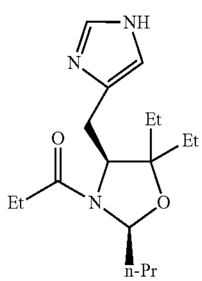 | $C_{17}H_{29}N_3O_2$ | 307 | DMSO |
| LC-44 | 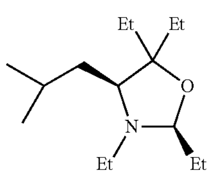 [SMILES: CC[C@@H]1OC(CC)(CC)[C@H](CC(C)C)N1CC] | $C_{15}H_{31}NO$ | 241 | DMSO |
| LC-45 | 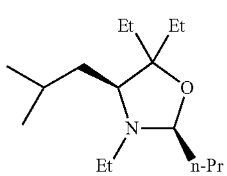 | $C_{16}H_{33}NO$ | 255 | DMSO |
| LC-46 | 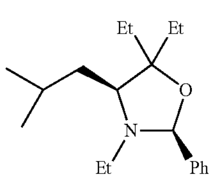 [SMILES: CCN1[C@@H](CC(C)C)C(CC)(CC)O[C@H]1c1ccccc1] | $C_{19}H_{31}NO$ | 289 | DMSO |

Table 2 lists some selected compounds according to an embodiment of the present invention.

TABLE 2

Selected oxazolidine derivatives having various substructures

| Compound | Compound No. | $R^4$ | $R^2$ | $R^3$ |
|---|---|---|---|---|
| (isobutyl-substituted oxazolidine) | 4a | H | Et | Et |
| | 4b | H | Et | n-Pr |
| | 4c | H | Et | Ph |
| | 4d | H | n-Pr | Et |
| | 4e | H | n-Pr | n-Pr |
| | 4f | H | n-Pr | Ph |
| | 5a | PhCO | Et | Et |
| | 5b | PhCO | Et | n-Pr |
| | 5c | PhCO | n-Pr | Et |
| | 5d | PhCO | n-Pr | n-Pr |
| (sec-butyl-substituted oxazolidine) | 4g | H | Et | Et |
| | 4h | H | Et | n-Pr |
| | 4i | H | Et | Ph |
| | 4j | H | n-Pr | Et |
| | 4k | H | n-Pr | n-Pr |
| | 4l | H | n-Pr | Ph |
| | 5e | PhCO | Et | Et |
| | 5f | PhCO | n-Pr | Et |
| | 5g | PhCO | n-Pr | n-Pr |

TABLE 2-continued

Selected oxazolidine derivatives having various substructures

| Compound | Compound No. | $R^4$ | $R^2$ | $R^3$ |
|---|---|---|---|---|
| (benzyl-substituted oxazolidine) | 4m | H | Et | Et |
| | 4n | H | Et | n-Pr |
| | 4o | H | n-Pr | Et |
| | 4p | H | n-Pr | n-Pr |
| (isobutyl-substituted oxazolidine) | 8a | Et | Ph | Et |
| | 8b | Et | Ph | n-Pr |
| | 8c | n-Pr | Bu | Et |
| | 8d | n-Pr | Bu | n-Pr |
| | 8e | Et | Et | Et |
| | 8f | Et | Et | n-Pr |
| | 8g | Et | Et | Ph |

Table 3 lists some selected chiral oxazolidine compounds according to an embodiment of the present invention.

TABLE 3

| Compound No. | Structure | Molecular Formula | Molecular Weight |
|---|---|---|---|
| LC-02-d01 | 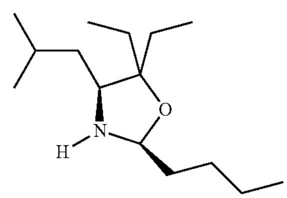 [SMILES: CCCC[C@H]1N[C@@H](CC(C)C)C(CC)(CC)O1] | $C_{15}H_{31}NO$ | 241 |
| LC-02-d02 | 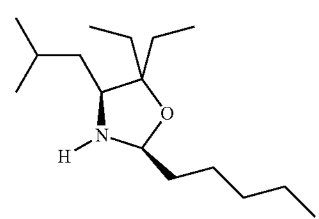 [SMILES: CCCCC[C@H]1N[C@@H](CC(C)C)C(CC)(CC)O1] | $C_{16}H_{33}NO$ | 255 |
| LC-02-d03 | 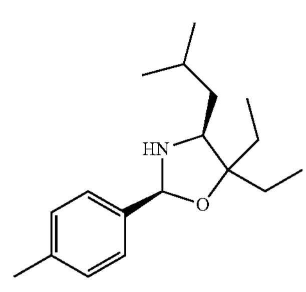 [SMILES: CCC1(CC)O[C@@H](c2ccc(C)cc2)N[C@H]1CC(C)C] | $C_{18}H_{29}NO$ | 275 |

TABLE 3-continued

| Compound No. | Structure | Molecular Formula | Molecular Weight |
|---|---|---|---|
| LC-02-d04 | 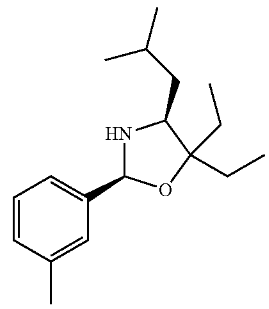 [SMILES: CCC1(CC)O[C@@H](c2cccc(C)c2)N[C@H]1CC(C)C] | $C_{18}H_{29}NO$ | 275 |
| LC-02-d05 | 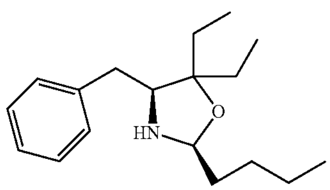 [SMILES: CCCC[C@H]1N[C@@H](Cc2ccccc2)C(CC)(CC)O1] | $C_{18}H_{29}NO$ | 275 |
| LC-02-d06 | 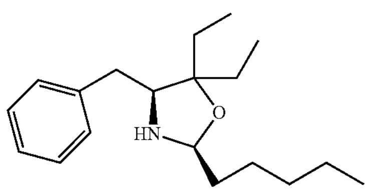 [SMILES: CCCCC[C@H]1N[C@@H](Cc2ccccc2)C(CC)(CC)O1] | $C_{19}H_{31}NO$ | 289 |
| LC-02-d07 | 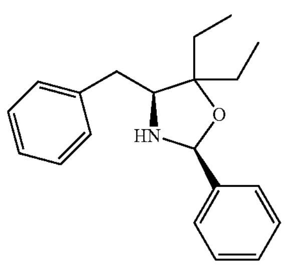 [SMILES: CCC1(CC)O[C@@H](c2ccccc2)N[C@H]1Cc1ccccc1] | $C_{20}H_{25}NO$ | 295 |
| LC-02-d08 | 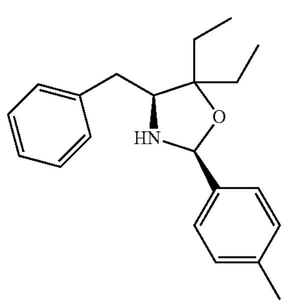 [SMILES: CCC1(CC)O[C@@H](c2ccc(C)cc2)N[C@H]1Cc1ccccc1] | $C_{21}H_{27}NO$ | 309 |
| LC-02-d09 | 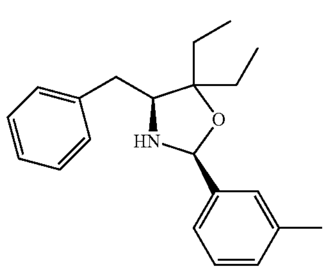 [SMILES: CCC1(CC)O[C@@H](c2cccc(C)c2)N[C@H]1Cc1ccccc1] | $C_{21}H_{27}NO$ | 309 |

TABLE 3-continued

| Compound No. | Structure | Molecular Formula | Molecular Weight |
|---|---|---|---|
| LC-02-d10 | 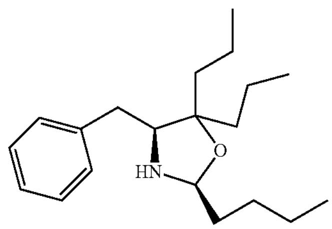 [SMILES: CCCC[C@H]1N[C@@H](Cc2ccccc2)C(CCC)(CCC)O1] | $C_{20}H_{33}NO$ | 303 |
| LC-02-d11 | 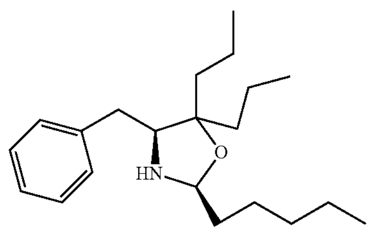 [SMILES: CCCCC[C@H]1N[C@@H](Cc2ccccc2)C(CCC)(CCC)O1] | $C_{21}H_{35}NO$ | 317 |
| LC-02-d12 | 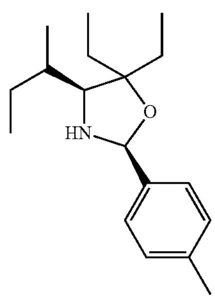 [SMILES: CCC(C)[C@@H]1N[C@H](c2ccc(C)cc2)OC1(CC)CC] | $C_{18}H_{29}NO$ | 275 |
| LC-02-d13 | 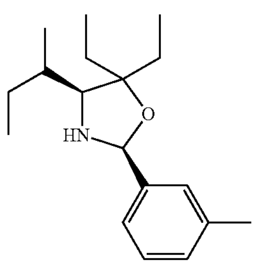 [SMILES: CCC(C)[C@@H]1N[C@H](c2cccc(C)c2)OC1(CC)CC] | $C_{18}H_{29}NO$ | 275 |
| LC-02-d14 | 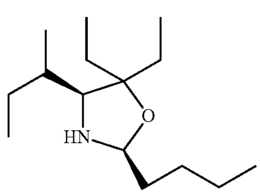 [SMILES: CCCC[C@H]1N[C@@H](C(C)CC)C(CC)(CC)O1] | $C_{15}H_{31}NO$ | 241 |
| LC-02-d15 | 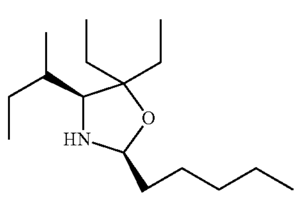 [SMILES: CCCCC[C@H]1N[C@@H](C(C)CC)C(CC)(CC)O1] | $C_{16}H_{33}NO$ | 255 |

Accordingly, in a first set of embodiments, the invention provides a compound of formula (I):

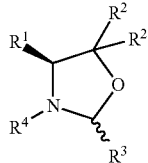
(I)

or a pharmaceutically acceptable salt, N-oxide, prodrug, hydrate and isomers thereof;

$R^1$ is selected from the group consisting of $(C_1-C_8)$alkyl, $(C_1-C_8)$heteroalkyl, arylalkyl, $(C_3-C_8)$cycloalkyl, $(C_3-C_8)$cycloalkyl-alkyl, heterocycloalkyl, heterocycloalkyl-$(C_1-C_6)$alkyl, heteroaryl-$(C_1-C_6)$alkyl, heterocyclyl-alkyl and aryl;

$R^2$ and $R^3$ are each independently selected from the group consisting of —H, $(C_1-C_8)$alkyl, $(C_1-C_8)$heteroalkyl, heteroaryl-alkyl and aryl;

$R^4$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, —$X^1S(O)R^a$, —$X^1S(O)_2R^a$, —$X^1SO_2NH_2$, —$X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group; wherein $R^a$ is $(C_1-C_8)$ alkyl or aryl and each $X^1$ is independently a bond or an $(C_1-C_4)$alkylene; the wavy line denoted by ⁓ indicates the carbon to which the wavy line is attached has a stereoconfiguration of R, S or a mixture thereof; optionally, $R^1$ and $R^4$ together with the atoms to which they are attached form a 5-membered heterocyclic ring containing 0-1 additional ring heteroatom selected from O or N; and wherein each of $R^1$-$R^4$ groups is optionally substituted with from 1-3 $R^b$ substituents independently selected from the group consisting of halogen, —OH, —$OR^c$, —$OSi(R^c)_3$, —$OC(O)O$—$R^c$, —$OC(O)R^c$, —$OC(O)NHR^c$, —$OC(O)N(R^c)_2$, —SH, —$SR^c$, —$S(O)R^c$, —$S(O)_2R^c$, —$SO_2NH_2$, —$S(O)_2NHR^c$, —$S(O)_2N(R^c)_2$, —$NHS(O)_2R^c$, —$NR^cS(O)_2R^c$, —$C(O)NH_2$, —$C(O)NHR^c$, —$C(O)N(R^c)_2$, —$C(O)R^c$, —$C(O)H$, —$C(=S)R^c$, —$NHC(O)R^c$, —$NR^cC(O)R^c$, —$NHC(O)NH_2$, —$NR^cC(O)NH_2$, —$NR^cC(O)NHR^c$, —$NHC(O)NHR^c$, —$NR^cC(O)N(R^c)_2$, —$NHC(O)N(R^c)_2$, —$CO_2H$, —$CO_2R^c$, —$NHCO_2R^c$, —$NR^cCO_2R^c$, —$R^c$, —CN, —$NO_2$, —$NH_2$, —$NHR^c$, —$N(R^c)_2$, —$NR^cS(O)NH_2$, —$NR^cS(O)_2NHR^c$, —$NH_2C(=NR^c)NH_2$, —$N=C(NH_2)NH_2$, —$C(=NR^c)NH_2$, —$N_3$, —NH—OH, —$NR^c$—OH, —$NR^c$—$OR^c$, —N=C=O, —N=C=S. —$Si(R^c)_3$, —NH—$NHR^c$, —$NHC(O)NHNH_2$, —$P(O)(OR^c)_2$, —$N=C=NR^c$ and —S—CN, wherein each $R^c$ is independently an alkyl or aryl, wherein $R^c$ is optionally further substituted with from 1-3 substituents selected from the group consisting of halogen, —OH, —$OR^d$, —SH, —$SR^d$, —$S(O)_2R^d$, —$SO_2NH_2$, —$C(O)NH_2$, —$C(O)NHR^d$, —$C(O)N(R^d)_2$, —$C(O)R^d$, —$C(O)H$, —$NHC(O)R^d$, —$NR^dC(O)R^d$, —$CO_2H$, —$CO_2R^d$, —$R^d$, —CN, —$NO_2$, —$NH_2$, —$NHR^d$, —$N(R^d)_2$, —NH—OH, —$NR^d$—OH, —$NR^d$—$OR^d$, —N=C=O, —N=C=S, —NH—$NHR^d$ and —S—CN, wherein each $R^d$ is independently an $(C_1-C_6)$alkyl.

In a second set of embodiments, the invention provides a compound of formula Ia:

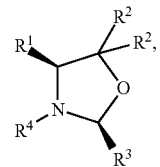
Ia wherein $R^3$ is selected from the group consisting of $(C_1-C_8)$ alkyl, $(C_1-C_8)$heteroalkyl, heteroaryl-alkyl and aryl; and the substitutuents $R^2$ and $R^4$ are as defined in the compounds of the first set.

In a third set of embodiments, the invention provides a compound of formula Ib:

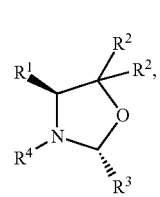
Ib wherein $R^3$ is selected from the group consisting of $(C_1-C_8)$ alkyl, $(C_1-C_8)$heteroalkyl, heteroaryl-alkyl and aryl; and the substitutuents $R^2$ and $R^4$ are as defined in the compounds of the first set.

In a fourth set of embodiments, the invention provides a compound of any of the first, second and third sets, wherein $R^3$ is —H.

In a fifth set of embodiments, the invention provides a compound of any of the first, second, third and fourth sets, wherein $R^1$ is selected from the group consisting of $(C_1-C_8)$ alkyl, $(C_1-C_8)$heteroalkyl, aryl-$(C_1-C_6)$alkyl and heteroaryl-$C_{1-6}$alkyl, each of which is optionally substituted with from 1-3 $R^b$.

In a sixth set of embodiments, the invention provides a compound of any of the first, second, third and fourth sets, wherein $R^1$ is selected from $(C_1-C_8)$alkyl, phenyl-$(C_1-C_6)$ alkyl and 5- or 6-membered heteroaryl-$C_{1-6}$alkyl, each of which is optionally substituted with from 1-3 $R^b$.

In a seventh set of embodiments, the invention provides a compound of any of the first, second, third, fourth, fifth and sixth sets, wherein $R^b$ is selected from the group consisting of halogen, —OH, —$OR^c$, —$OSi(R^c)_3$, —$OC(O)O$—$R^c$, —$OC(O)R^c$, —$OC(O)NHR^c$, —$OC(O)N(R^c)_2$, —SH, —$S(O)R^c$, —$S(O)_2R^c$, —$C(O)N(R^c)_2$, —$C(O)R^c$, —$C(O)H$, —$C(=S)R^c$, —$NHC(O)R^c$, —$NR^cC(O)R^c$, —$CO_2H$, —$CO_2R^c$, —$NHCO_2R^c$, —$NR^cCO_2R^c$, $R^c$, —CN, —$NO_2$, —$NH_2$, —$NHR^c$, —$N(R^c)_2$, —$N_3$, —NH—OH, —$NR^c$—OH and —$NR^c$—$OR^c$.

In an eighth set of embodiments, the invention provides a compound of any of the first, second, third, fourth, fifth, sixth and seventh sets, wherein $R^1$ is selected from the group consisting of $(C_1-C_8)$alkyl, phenyl-$(C_1-C_6)$alkyl and 5-membered heteroaryl-$C_{1-6}$alkyl, wherein the heteroaryl is optionally fused with a 5- or 6-membered aromatic ring having from 0-2 additional heteroatoms selected from N, O or S.

In a ninth set of embodiments, the invention provides a compound of any of the first, second, third, fourth, fifth, sixth, seventh and eighth sets, wherein $R^1$ is selected from $(C_1-C_8)$ alkyl, phenyl-$(C_1-C_6)$alkyl, imidazoly-$C_1$-$C_6$alkyl, pyrazolyl-$(C_1-C_6)$alkyl, oxazoly-$(C_1-C_6)$alkyl, isoxazoyl-$(C_1$-

$C_6$)alkyl, thiazolyl-($C_1$-$C_6$)alkyl, isothiazoly-($C_1$-$C_6$)alkyl, furanyl-($C_1$-$C_6$)alkyl, indolyl-($C_1$-$C_6$)alkyl and thiophenyl-($C_1$-$C_6$)alkyl.

In a tenth set of embodiments, the invention provides a compound of any of the first, second, third, fourth, fifth, sixth, seventh, eighth and ninth sets, wherein $R^1$ is selected from the group consisting of Me, —$CH_2(Me)_2$, —$CH_2CH(Me)_2$, —CHMe(Et), —$CH_2CH_2CH_3$, —$CH_2Ph$, —$CH_2PhOH$, —$CH_2CH_2CH_2CH_2NH_2$, —$CH_2CH_2CONH_2$, -Ph, -PhMe, -$PhNO_2$, -$PhOCH_3$, -$PhNH_2$, -PhF, -PhBr, -PhI, PhCN, -Ph-$COOR^c$, -Ph-$OCOR^c$, -$PhNHCOR^c$, -Ph-COOH, —$CH_2CO_2H$, —$CH_2CH_2COOH$, —$CH_2CONH_2$, —$CH_2OH$, —$CH(OH)CH_3$, indolyl-$CH_2$—, indol-3-yl-methyl, —$(CH_2)_3NHC(=NH)NH_2$, —$CH_2CH_2CHNHCH(NH_2)_2$, imidazolyl-$CH_2$—, imidazol-4-yl-$CH_2$—, imidazol-5-yl-$CH_2$—, $CH_2CH_2SMe$ and —$CH_2SH$.

In an eleventh set of embodiments, the invention provides a compound of any of the first, second, third, fourth, fifth, sixth, seventh, eighth and ninth and tenth sets, wherein $R^1$ is selected from the group consisting of —$CH_2CH(Me)_2$, $CH_3CH_2(CH_3)CH$—, benzyl or imidazoly-$CH_2$—.

In a twelfth set of embodiments, the invention provides a compound of any one of sets 1, 2, 3, 4, 5, 6, 7, 8, 9, 10 and 11, wherein $R^2$ is selected from the group consisting of —H, ($C_1$-$C_8$)alkyl and aryl, wherein the alkyl and aryl are optionally substituted with from 1-3 $R^b$.

In a thirteenth set of embodiments, the invention provides a compound of any one of sets 1, 2, 3, 4, 5, 6, 7, 8, 9, 10, 11 and 12, wherein $R^2$ is selected from the group consisting of —H, ($C_1$-$C_8$)alkyl and phenyl, wherein the alkyl and phenyl are optionally substituted with from 1-3 $R^b$ substituents selected from the group consisting of —OH, —$OR^c$, —$OSi(R^c)_3$, —OC(O)O—$R^c$, —$OC(O)R^c$, —$OC(O)NHR^c$, —OC(O)N($R^c)_2$, —SH, —$SR^c$, —$S(O)R^c$, —$S(O)_2R^c$, —$C(O)N(R^c)_2$, —$C(O)R^c$, —C(O)H, —$C(=S)R^c$, —$NHC(O)R^c$, —$NR^cC(O)R^c$, —$CO_2H$, —$CO_2R^c$, —$NHCO_2R^c$, —$NR^cCO_2R^c$—$R^c$, —CN, —$NO_2$, —$NH_2$, —$NHR^c$, —$N(R^c)_2$, —$N_3$, —NH—OH, —$NR^c$—OH and —$NR^c$—$OR^c$.

In a fourteenth set of embodiments, the invention provides a compound of any one of sets 1, 2, 3, 4, 5, 6, 7, 8, 9, 10, 11, 12 and 13, wherein $R^b$ is selected from the group consisting of halogen, —OH, —$R^c$, —CN, —$NO_2$, —$NH_2$, —$NHR^c$ and —$N(R^c)_2$.

In a fifteenth set of embodiments, the invention provides a compound of any one of sets 1, 2, 3, 4, 5, 6, 7, 8, 9, 10 and 11, wherein $R^2$ is selected from the group consisting of —H, -Me, -Et, —Pr, -Bu, -iPr, -tBu, -iBu, —$CH_2CH_2CH_2CH_2CH_3$, -Ph, -PhMe, -$PhNO_2$, -PhOMe, -$PhNH_2$, -Ph-F, -Ph-Br, -Ph-Cl, -Ph-I, -PhCN, -Ph-$COOR^c$, -Ph-$OCOR^c$, -$PhNHCOR^c$ and -Ph-COOH.

In a sixteenth set of embodiments, the invention provides a compound of the any one of sets the 1, 2, 3, 4, 5, 6, 7, 8, 9, 10, 11, 12, 13, 14 and 15, wherein $R^3$ is selected from the group consisting of —H, ($C_1$-$C_8$)alkyl and aryl, wherein the alkyl and aryl are optionally substituted with from 1-3 $R^b$.

In a seventeenth set of embodiments, the invention provide a compound of any one of sets 1, 2, 3, 4, 5, 6, 7, 8, 9, 10, 11, 12, 13, 14 and 15, wherein $R^3$ is selected from the group consisting of —H, ($C_1$-$C_8$)alkyl and phenyl, wherein the alkyl and phenyl are optionally substituted with from 1-3 $R^b$ substituents selected from the group consisting of —OH, —$OR^c$, —$OSi(R^c)_3$, —OC(O)O—$R^c$, —$OC(O)R^c$, —$OC(O)NHR^c$, —$OC(O)N(R^c)_2$, —SH, —$SR^c$, —$S(O)R^c$, —$S(O)_2R^c$, —$C(O)N(R^c)_2$, —$C(O)R^c$, —C(O)H, —$C(=S)R^c$, —$NHC(O)R^c$, —$NR^cC(O)R^c$, —$CO_2H$, —$CO_2R^c$, —$NHCO_2R^c$, —$NR^cCO_2R^c$, —$R^c$, —CN, —$NO_2$, —$NH_2$, —$NHR^c$, —$N(R^c)_2$, —$N_3$, —NH—OH, —$NR^c$—OH and —$NR^c$—$OR^c$.

In an eighteenth set of embodiments, the invention provides a compound of any one of sets 1, 2, 3, 4, 5, 6, 7, 8, 9, 10, 11, 12, 13, 14, 15, 16 and 17, wherein $R^b$ is selected from the group consisting of halogen, —OH, —$OR^c$, —$R^c$, —CN, —$NO_2$, —$NH_2$, —$NHR^c$ and —$N(R^c)_2$.

In a nineteenth set of embodiments, the invention provides a compound of any one of sets 1, 2, 3, 4, 5, 6, 7, 8, 9, 10, 11, 12, 13, 14 and 15, wherein $R^d$ is selected from the group consisting of —H, -Me, -Et, —Pr, -Bu, -iPr, -tBu, -iBu, —$CH_2CH_2CH_2CH_2CH_3$, -Ph, -PhMe, -$PhNO_2$, -PhOMe, -$PhNH_2$, -Ph-F, -Ph-Br, -Ph-Cl, -Ph-I, -PhCN, -Ph-$COOR^c$, -Ph-$OCOR^c$, -$PhNHCOR^c$ and -Ph-COOH.

In a 20th set of embodiments, the invention provides a compound of any one of sets 1, 2, 3, 4, 5, 6, 7, 8, 9, 10, 11, 12, 13, 14, 15, 16, 17, 18 and 19, wherein $R^4$ is selected from the group consisting of —H, aryl-($C_1$-$C_6$)alkyl, ($C_1$-$C_8$)alkyl, ($C_1$-$C_8$)heteroalkyl, —$C(O)NH_2$, —$C(O)NHR^a$, —C(O)N$(R^a)_2$, —$C(O)R^a$, —C(O)H, —$C(=S)R^a$, —$CO_2H$, —$CO_2R^a$, —$P(O)(OR^a)_2$ and an amino protecting group, wherein the aliphatic and aromatic portion of the $R^4$ group are optionally substituted with from 1-3 $R^b$ substituents.

In a 21st set of embodiments, the invention provides a compound of any one of sets 1, 2, 3, 4, 5, 6, 7, 8, 9, 10, 11, 12, 13, 14, 15, 16, 17, 18 and 19, wherein $R^4$ is selected from the group consisting of —H, phenyl-($C_1$-$C_6$)alkyl, ($C_1$-$C_8$)alkyl, —$C(O)NH_2$, —$C(O)NHR^a$, —$C(O)N(R^a)_2$, —$C(O)R^a$, —C(O)H, —$C(=S)R^a$, —$CO_2H$, —$CO_2R^a$ and an amino protecting group, wherein $R^a$ is alkyl or optionally substituted phenyl.

In a 22nd set of embodiments, the invention provides a compound of any one of sets 1, 2, 3, 4, 5, 6, 7, 8, 9, 10, 11, 12, 13, 14, 15, 16, 17, 18 and 19, wherein $R^4$ is selected from the group consisting of —H, —CHO, PhCO—, PhNHCO—, PhOCO—, $CH_3NHCO$—, $CH_3OCO$—, $CH_3CO$—, EtCO—, -Me, -Et, —Pr, -Bu, iPr, iBu, -tBu, —$CH_2CH_2CH_2CH_2CH_3$ and t-BuO-CO—.

In a $23^{rd}$ set of embodiments, the invention provides a compound of any one of sets 1, 2, 3, 4, 5, 6, 7, 8, 9, 10, 11, 12, 13, 14, 15, 16, 17, 18, 19, 20, 21 and 22, wherein $R^1$ and $R^4$ together with the atoms to which they are attached form a pyrrolidine ring, optionally substituted with from 1-3 $R^d$.

In a 24 th set of embodiments, the invention provides a compound of any one of sets 1, 2, 3, 4, 5, 6, 7, 8, 9, 10, 11, 12, 13, 14, 15, 16, 17, 18, 19, 20, 21 and 22, wherein the compound is selected from the group consisting of:

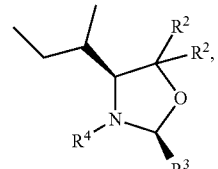

Ia-1

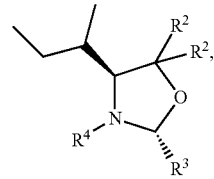

Ib-1

-continued

Ic-1 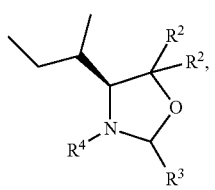

Ia-2 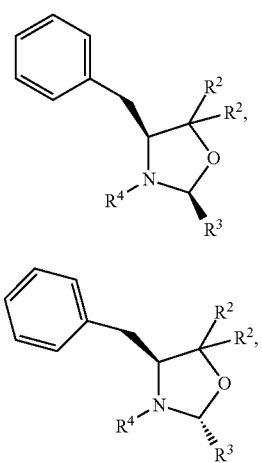

Ib-2

Ic-2

Ia-3

Ib-3

Ic-3

-continued

Ia-4 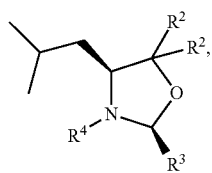

Ib-4 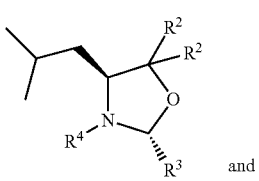

and

Ic-4 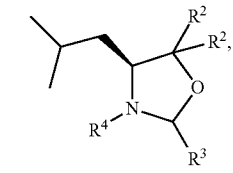

wherein $R^5$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, —$X^1S(O)R^a$, —$X^1S(O)_2R^a$, —$X^1SO_2NH_2$, —$X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group.

In a 25th set of embodiments, the invention provides a compound of any one of sets 1, 2, 3, 4, 5, 6, 7, 8, 9, 10, 11, 12, 13, 14, 15, 16, 17, 18, 19, 20, 21 and 22, wherein the compound is selected from the group consisting of:

Ia-1 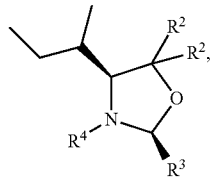

Ib-1 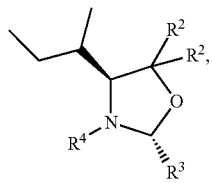

Ic-1 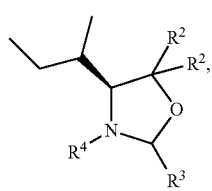

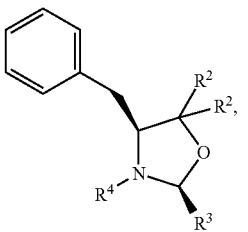

Ia-2

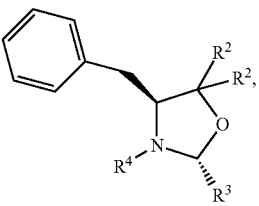

Ib-2

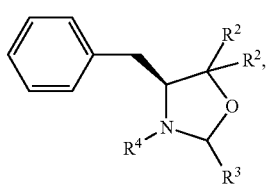

Ic-2

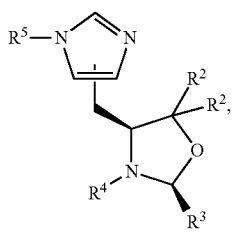

Ia-3

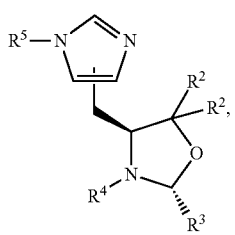

Ib-3

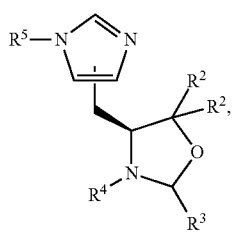

Ic-3

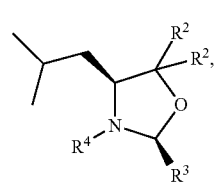

Ia-4

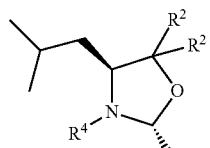

Ib-4 and

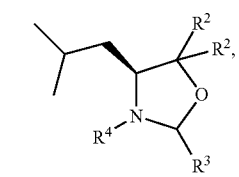

Ic-4 wherein $R^5$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, —$X^1S(O)R^a$, —$X^1S(O)_2R^a$, —$X^1SO_2NH_2$, —$X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group.

In a 26th set of embodiments, the invention provides a compound of any of sets 1, 2, 3, 24 and 25, wherein $R^2$ is $(C_1-C_8)$alkyl, $R^3$ is $(C_1-C_8)$alkyl or optionally substituted aryl and $R^4$ is —H or —$COR^a$.

In a 27th set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25 and 26, wherein $R^3$ is $(C_1-C_8)$alkyl.

In a 28th set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25 and 26, wherein $R^3$ is an optionally substituted aryl.

In a 29th set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27 and 28, wherein $R^4$ is —H.

In a 30th set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27 and 28, wherein $R^4$ is —$COR^a$.

In a 31st set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30, wherein $R^a$ is optionally substituted phenyl.

In a 32nd set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27 and 28, wherein $R^4$ is $(C_1-C_8)$alkyl, $R^2$ is $(C_1-C_8)$alkyl or optionally substituted aryl and $R^3$ is $(C_1-C_8)$alkyl or optionally substituted aryl.

In a 33rd set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27 and 28, wherein $R^4$ is $(C_1-C_8)$alkyl, $R^2$ is $(C_1-C_8)$alkyl and $R^3$ is $(C_1-C_8)$alkyl or optionally substituted aryl.

In a 34th set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27 and 28, wherein $R^4$ is $(C_1-C_8)$alkyl and each of $R^2$ and $R^3$ is independently optionally substituted aryl.

In a 35th set of embodiments, the invention provides a compound of any of sets 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 and 34 wherein the optionally substituted aryl is an optionally substituted phenyl.

In a 36th set of embodiments, the invention provides a pharmaceutical composition comprising a compound of any one of sets 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 and 35, and a pharmaceutically acceptable carrier or excipient.

In a 37th set of embodiments, the invention provides a method of inhibiting the activities of an NMDA receptor, the method comprising: contacting a compound of any one of sets 1-35 or a composition of set 36 with the NMDA receptor.

In a 38th set of embodiments, the invention provides a a method of set 37, wherein the NMDA receptor is an activated glutamate receptor.

In a 39th set of embodiments, the invention provides a method of inhibiting the synapse transmission by glutamate, the method comprising: contacting a compound of any one of sets 1-35 or a composition of set 36 with an activated extrasynaptic NMDA receptor.

In a 40th set of embodiments, the invention provides a method of treating central nervous system disorders in a mammal, the method comprising: contacting a compound of any one of sets 1-35 or a composition of set 36 with the NMDA receptor.

In a 41st set of embodiments, the invention provides a method of treating or preventing a neurodegenerative disease or neuropathological conditions in a mammal, the method comprising: administering to said mammal a therapeutically effective amount of a compound of any one of sets 1-35 or a composition of set 36.

In a 42nd set of embodiments, the invention provides a method of set 41, wherein the disease is selected from the group consisting of amyotrophic lateral sclerosis, Alzheimer's disease, Parkinson's disease, Huntington's disease, neuropathic pain, stroke, epilepsy, CNS trauma, brain trauma, and cardiac arrest.

In a 43rd set of embodiments, the invention provides a method of set 42, wherein the condition is selected from the group consisting of neuropathic pain, stroke, brain trauma and epilepsy.

In a 44th set of embodiments, the invention provides a method of enhancing the brain's cognitive function in a mammal, the method comprising: administering to said mammal a therapeutically effective amount of a compound of any one of sets 1-35 or a composition of set 36.

In a 45th set of embodiments, the invention provides a method of preventing neuronal damage under a stress condition in a mammal, the method comprising: administering to said mammal a therapeutically effective amount of a compound of any one of sets 1-35 or a composition of set 36.

In a 46th set of embodiments, the invention provides a method of set 45, wherein said stress condition is a stroke, head trauma or cardiac arrest.

In a 47th set of embodiments, the invention provides a method of inhibiting the activities of an NMDA receptor, the method comprising: contacting any of compounds LC-01 to LC-46, 4a to 4p, 5a to 5g, 8a to 8g and LC-02d-01 to LC-02d-15 as set forth in Tables 1 to 3 and Examples.

In a 48th set of embodiments, the invention provides a method of treating or preventing neurodegenerative diseases and neuropathological disorders or enhancing the brain's cognitive function in a mammal, said method comprising: administering to said mammal a therapeutically effective amount of any of compounds LC-01 to LC-46, 4a to 4p, 5a to 5g, 8a to 8g and LC-02d-01 to LC-02d-15 as set forth in Tables 1 to 3 and Examples.

Preparation of Compounds

Compounds of the present invention can be prepared using readily available starting materials or known intermediates. Examples of starting materials available from commercial suppliers include, but are not limited to, naturally occurring L-amino acids, such as glycine, alanine, valine, lucine, isolucine, phenylalanine, proline, serine, threonine, tyrosine, cysteine, methionine, asparagines, glutamine, tryptophan, aspartic acid, glutamic acid, lysine, arginine, histidien and the like. The amino acids can be either optically active or racemic. Non commercially available amino acids with various side chains can be prepared using Strecker amino acid synthetic approach by condensing an aldehyde or ketone with ammonium chloride in the presence of potassium cyanide to form an α-aminonitrile, which is subsequently hydrolyzed to give the desired amino-acid (see, Kendall, et al. *Organic Syntheses, Coll. Vol.* 1, 1941, p. 21; Vol. 9, 1929, p. 4; and Clarke, et al. *Organic Syntheses, Coll. Vol.* 2, 1943, p. 29; Vol. 11, 1931, p. 4). All the compounds can be prepared by the methods described in the synthetic schemes and Examples 1 and 2. For example, the compounds set forth in Tables 1-3 can be prepared by the methods described in Schemes 1 to 3 described hereinbelow. Scheme 1 illustrates a Strecker synthetic process.

Scheme 1

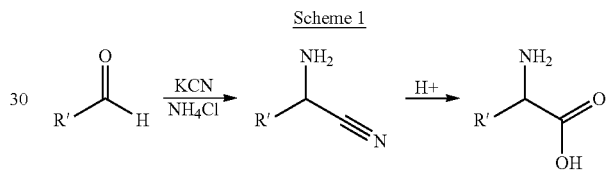

Optically active α-amino acids can be readily prepared by using chiral auxillaries or asymmetric catalysts (see, Ishitani, et al. *J. Am. Chem. Soc.* 2000, 122, 762-766; Huang, et al. *Org, Lett.* 2004, 6, 5027-5029; and Duthaler *Tetrahedron* 1994, 50, 1539-1650). The choice of appropriate reaction conditions are within those of skill in the art.

As shown in the examples below, there are a variety of synthetic routes by which a skilled artisan can prepare compounds and intermediates of the present invention. Schemes 2 and 3 illustrate two approaches for the synthesis of certain optically active oxazolindine derivatives. In each of these schemes R', R'', R''' and R'''' are non-interferring substituents. Depending on the reaction conditions, R', R'' and R''' may optionally contain certain hydroxy, amino and/or carbonyl protecting groups. The choice of the protecting groups are within the ability of those of skill in the art. R', R'' and R''' correspond to substituents $R^1$, $R^2$ and $R^3$, respectively, in formula I.

The schemes below provide certain synthetic routes that can be followed to access certain oxazolidine derivatives of the present invention. Other routes or modification of the routes presented below would be readily apparent to a skilled artisan and within the scope of the present invention.

Scheme 2

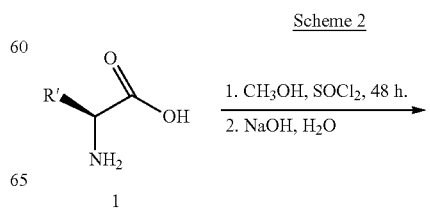

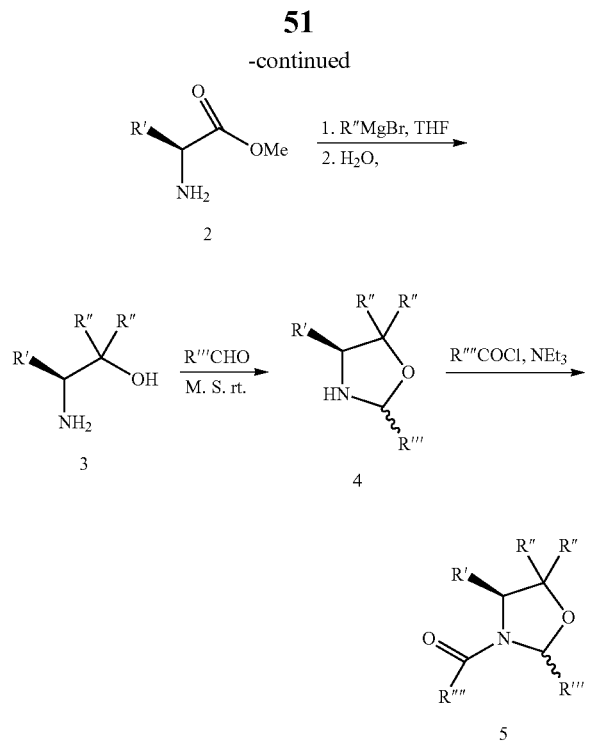

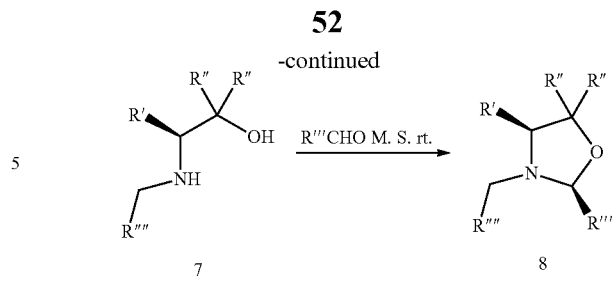

Scheme 2 shows one synthetic approach to oxazolidine derivatives. In Scheme 2, α-amino acid compound 1 is converted to α-amino acid ester compound 2, which is reacted with a Grignard reagent to generate amino alcohol 3. Condensation of amino alcohol compound 3 with an aldehyde to afford an oxazolidine compound 4. Compound 4 obtained can be a single isomer or a mixture of two diastereomers. In circumstances where compound 4 obtained exists as a mixture of two diastereomers, optically active single isomer of compound 4 can be obtained from the diastereomers mixture using standard chiral separation techniques, such as recrystallizations or column chromatographies, which are well known to those of skill in the art. Compound 5 can be synthesized by reacting the secondary amino group with an acyl chloride.

Scheme 3

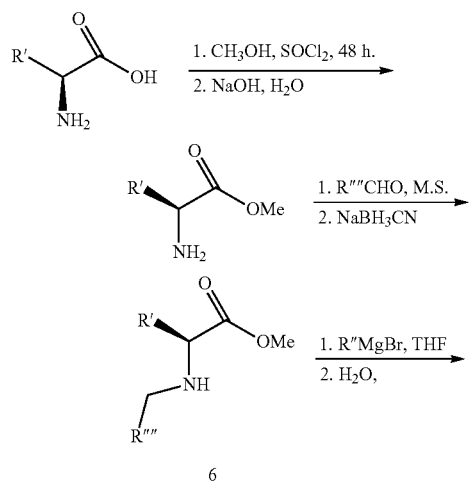

Scheme 3 shows another approach for the synthesis of oxazolidine derivatives. The α-amino group in compound 2 is alkylated through a reductive amination process before compound 2 is converted to amino alcohol 7. The processes for formation of oxazolidine 8 are similar to those shown in Scheme 2.

IV. Pharmaceutical Compositions

In accordance with the present invention, a therapeutically effective amount of a compound of any of Formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g, and LC-02d-01 to LC-02d-15 and a compound as defined in any one of claims 1 to 35 can be used for the preparation of a pharmaceutical composition useful for treating and/or preventing amyotrophic lateral sclerosis, Alzheimer's disease, Parkinson's disease, Huntington's disease, neuropathic pain, stroke, epilepsy, CNS trauma, head trauma, brain trauma, cardiac arrest and other diseases and disorders of the central nervous system.

The compositions of the invention can include compounds of any of Formulas (I), I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g, and LC-O$_2$d01 to LC-02d-15, and a compound as defined in any one of claims 1 to 35, pharmaceutically acceptable salts thereof, a hydrate thereof or a hydrolysable precursor thereof. In general, the compound is mixed with suitable carriers or excipient(s) in a therapeutically effective amount. By a "therapeutically effective dose", "therapeutically effective amount" or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of central nervous system diseases or disorders.

The compounds of any of Formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 that are used in the methods of the present invention can be incorporated into a variety of formulations for therapeutic administration. More particularly, the compounds of any of Formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02-d01 to LC-02d-15 or a pharmaceutically acceptable salt thereof, as defined in any one of claims 1 to 36 can be formulated into pharmaceutical compositions by combination with appropriate, pharmaceutically acceptable carriers or diluents and can be formulated into preparations in solid, semi-solid, liquid or gaseous forms, such as tablets, capsules, pills, powders, granules, dragees, suspensions, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local manner, in a depot or sustained release formulation. In addition, the compounds can be administered in a liposome.

The compounds of any of Formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 can be formulated with common excipients, diluents or carriers and compressed into tablets or formulated as elixirs or solutions for convenient oral administration or administered by intramuscular or intravenous routes. The compounds can be administered transdermally and can be formulated as sustained release dosage forms and the like. Compounds of Formula (I) can be administered alone, in combination with each other or they can be used in combination with other known compounds.

Suitable formulations for use in the present invention are found in *Remington: The Science and Practice of Pharmacy*, 21st ed., Lippincott Williams & Wilkins, Philadelphia, Pa., 2005, which is incorporated herein by reference. Moreover, for a brief review of methods for drug delivery, see, Langer, *Science* (1990) 249: 1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing a compound of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

Dragee cores are provided with suitable coatings. For this purpose, concentrated sugar solutions can be used, which can optionally contain gum arabic, talc, polyvinyl pyrrolidone, carbopol gel, polyethylene glycol and/or titanium dioxide, lacquer solutions and suitable organic solvents or solvent mixtures. Dyestuffs or pigments can be added to the tablets or dragee coatings for identification or to characterize different combinations of active compound doses.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Alternatively, other deliveries for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

The compounds of this invention may also be coupled with a carrier that is a suitable polymer as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

Certain organic solvents such as dimethylsulfoxide (DMSO) also can be employed, although usually at the cost of greater toxicity. Additionally, the compounds can be delivered using a sustained-release, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics*, Ch. 1).

V. Methods of Treating Diseases and Disorders Modulated by NMDA Receptors

In another aspect, the present invention provides a method of inhibiting the activities of an NMDA receptor. The method includes/comprises contacting a compound of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 or a pharmaceutical composition thereof with the NMDA receptor. Preferably, the NMDA receptor is an activated NMDA receptor.

In one embodiment, the compounds of the present invention are NMDA antagonists that can be used to inhibit the binding of NMDA receptor ligand (e.g., glutamate) to NMDA receptor in vitro or in vivo. In general, such methods comprise the step of contacting an NMDA receptor with a sufficient amount of one or more NMDA receptor antagonist as provided herein, in the presence of NMDA receptor ligand in aqueous solution and under conditions otherwise suitable for binding of the ligand to NMDA receptor. The NMDA receptor may be present in suspension (e.g., in an isolated membrane or cell preparation), or in a cultured or isolated neuron cell.

Preferably, the amount of NMDA receptor modulator contacted with the receptor should be sufficient to inhibit NMDA binding to NMDA receptor in vitro as measured, for example, using whole-cell patch clamp studies, calcium mobilization assay, fluormetric imaging plate reader (FLIPR) assey, or neuronal survival assay.

In one embodiment of the invention, the NMDA antagonists of the invention are used to modulate, preferably inhibit, the activity of a NMDA receptor, for example, by contacting one or more compound(s) of the invention with a NMDA receptor (either in vitro or in vivo) under conditions suitable for binding of the modulator(s) to the receptor. The receptor may be present in solution or suspension, in a cultured or isolated cell preparation or within a patient. Any modulation of the activity may be assessed using patch clamp, FLIPR, or calcium assay techniques by detecting the ion current across the surface of neurons, or by survival assay, or immunocytochemical analysis. In general, an effective amount of NMDA antagonist(s) in an amount sufficient to modulate NMDA receptor activity in vitro within patch clamp studies and calcium mobilization assays, followed by neuronal survival assays.

In another embodiment, comparative studies are conducted to determine its efficacy in comparison to the known antagonist memantine. The effect of the compound on cognitive functions, such as in treating dementia, improving memory in test subjects is evaluated in animal models using Morris Water Maze task.

In yet another aspect, the present invention provides methods and use of the compounds of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 for preventing and/or treating a neurodegenerative diseases or neuropathological conditions in a mammal or human. The methods include administering to the mammal or human a therapeutically effective amount of the compounds of the present invention.

In a further aspect, the present invention provides methods and uses of compounds of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 for enhancing the brain's cognitive function in a mammal or human. The methods include administering to the subject a therapeutically effective amount of the compounds of the present invention.

Conditions that can be Treated by NMDA Antagonists:

The present invention provides neuroprotection as well as improves cognitive deficits. As NMDA receptor antagonists, the compounds of the present invention are useful in the treatment of acute and chronic disorders of CNS, ranging from neuropathological conditions to neurodegenerative diseases and conditions related to excitotoxicity. Disease states that can be treated using the compounds of the present invention include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, stroke, hydrocephalus, subarachnoid hemorrhage, vascular insufficiency, brain tumor, head trauma, brain trauma, epilepsy, Parkinson's disease, cerebral microangiopathy, cardiac arrest, pain medication, chemotherapy, oxygen deprivation, e.g, caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, and fetal alcohol syndrome, for example.

The present invention also represents a new paradigm for ischemic stroke treatment. Current treatments are severely limited. Traditionally, acute ischemic stroke is treated using a tissue plasminogen activator (tPA). This drug can prevent some of the adverse impacts associated with stroke but only if it is administered intravenously within the first three hours of the event and only if there is no bleeding in the brain. With such a small therapeutic window, only a small percentage of stroke patients (~3%) receive effective treatment. In recent years, stroke research has focused on developing neuroprotective agents, compounds that may make the brain more resistant to damage from stroke. The compounds of the present invention have the ability to halt the ischemic cascade.

The compounds of the present invention exhibit neuroprotective properties. Moreover, they have demonstrated the abilities to prevent neuronal damage under conditions of stress. They confer protection to neuronal tissue when exposed to stroke-related conditions, and have immense potential as therapeutic drugs in the prevention and management of ischemic stroke.

In one embodiment of the invention, the compounds of the invention can be used for the treatment of diseases selected from the group consisting of amyotrophic lateral sclerosis, Alzheimer's disease, Parkinson's disease and Huntington's disease, acute or chronic neuropathic pain, stroke, brain trauma, epilepsy stroke and dementia.

Treatment methods provided herein include, in general, administration to a patient an effective amount of one or more compounds provided herein, e.g., orally, nasally or parenterally. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein, for example, compounds of formula I. In a preferred embodiment, the compound(s) of the invention are preferably administered to a patient (e.g., a human) orally. The effective amount may be an amount sufficient to modulate the NMDA receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit the NMDA receptor in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

The compounds of the present invention can be administered as frequently as necessary, including hourly, daily, weekly or monthly. Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. The compounds utilized in the pharmaceutical method of the invention are administered at the initial dosage of about 0.0001 mg/kg to about 3000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. It will be understood, however, that the specific dose level for any particular patient will depend upon a variety of factors including the activity of the specific compound employed, the age, body weight, general health, sex, diet, time of administration, route of administration, rate of excretion, drug combination (i.e., other drugs being administered to the patient), the severity of the particular disease undergoing therapy, and other factors, including the judgment of the prescribing medical practitioner. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

The time-release effect can be obtained by capsule materials that dissolve at different pH values, by capsules that release slowly by osmotic pressure or by any other known means of controlled release.

It can be necessary to use dosages outside these ranges in some cases as will be apparent to those skilled in the art. Further, it is noted that the clinician or treating physician will know how and when to interrupt, adjust or terminate therapy in conjunction with individual patient response.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

The compounds of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3' or a pharmaceutically acceptable salt thereof, as defined in any one of claims 1 to 36 or formulae LC-01 to LC-46, 4a to 4p, 5a to 5g, 8a to 8g and LC-02d-01 to LC-02d-15 as set forth in Tables 1 to 3 and the Examples can also be administered in combination with additional therapeutic agents or diagnostic agents can be administered in combination with the compounds of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36 or formulae LC-01 to LC-46, 4a to 4p, 5a to 5g, 8a to 8g and LC-02d-01 to LC-02d-15 as set forth in Tables 1 to 3 and the Examples.

In some embodiments, the present invention provides a compound of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, as defined in any one of claims 1 to 36, for use as a medicament.

In other embodiments, the present invention provides a compound of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, according to any one of claims 1 to 36, for use in treating central nervous system disorders in a mammal, for treating or preventing a neurodegenerative disease or neuropathological conditions in a mammal, for enhancing the brain's cognitive function in a mammal, and for preventing neuronal damage under a stress condition in a mammal. In certain instances, the treatable diseases include, but are not limited to, amyotrophic lateral sclerosis, Alzheimer's disease, Parkinson's disease, Huntington's disease, neuropathic pain, stroke, epilepsy, CNS trauma, brain trauma, and cardiac arrest. The treatable and/or preventable conditions include neuropathic pain, stroke, brain trauma and epilepsy. In other instances, the preventable stress condition includes a stroke, head trauma or cardiac arrest.

In some embodiments, the present invention provides use of a compound of any of formulas I, Ia, Ib, Ic, Ia-1, Ia-2, Ia-3, Ia-4, Ib-1, Ib-2, Ib-3, Ib-4, Ic-1, Ic-2, Ic-3, Ic-4, Ia-3', Ib-3', Ic-3', LC-01 to LC-46, 4a to 4p, 5a to 5g, 8a to 8g and LC-02d-01 to LC-02d-15 or a pharmaceutically acceptable salt thereof, according to any one of claims 1 to 36, in the manufacture of a medicament for the prevention and/or treatment of central nervous system disorders and neurodegenerative disease or neuropathological conditions, for enhancing the brain's cognitive function in a mammal, and for preventing neuronal damage under a stress condition in a mammal. In certain instances, the treatable diseases include, but are not limited to, amyotrophic lateral sclerosis, Alzheimer's disease, Parkinson's disease, Huntington's disease, neuropathic pain, stroke, epilepsy, CNS trauma, brain trauma, and cardiac arrest. The treatable and/or preventable conditions include neuropathic pain, stroke, brain trauma and epilepsy. In other instances, the preventable stress condition includes a stroke, head trauma or cardiac arrest.

VI. Examples

The following abbreviations are used in the Examples and throughout the description of the invention:
NMDA: N-methyl-D-aspartic acid
M.S.: molecular sieves
DMSO: dimethyl sufoxide
EtOAc: ethyl acetate
TLC: thin layer chromatography Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

This example illustrates a general synthetic approach for the preparation of 1,3-N,O-oxazolidine derivatives.

General Procedure for the Preparation of Compound (S)-2

To a mixture of 10 mmol L-amino acid in 50 mL methanol was added dropwise $SOCl_2$ (15 mmol) at $-10°$ C. After warming up to room temperature the reaction mixture was refluxed for 4 h. The organic solvent was concentrated in vacuum, and then the residue was introduced with saturated aqueous $Na_2CO_3$ into pH 9.0 or so. The mixture was extracted three times with EtOAc. The combined organic layers were dried over anhydrous $Na_2SO_4$ and concentrated in vacuum to obtain the amino methyl ester (S)-2.

General Procedure for the Preparation of Amino Alcohol Compound (S)-3 Via the Reaction of the (S)-2 with Grignard Reagents A freshly prepared solution of Grignard reagent (6.2 mmol) in THF was added dropwise under nitrogen atmosphere to a solution of compound (S)-3 (2 mmol) in THF (10 mL). The reaction mixture was stirred at room temperature for over 4 h. When the reaction was complete as checked by TLC, the reaction mixture was cooled to $0°$ C. and a saturated cold aqueous $NH_4Cl$ was dropwise added into the mixture under vigorous stirring. The resulting mixture was extracted three times with EtOAc or ether. The solvent was combined and washed with brine, dried with anhydrous $Na_2SO_4$ and concentrated in vacuum. The crude amino alcohol was further purified by flash column chromatography on silica gel using ethyl acetate and methanol as eluents.

General Procedure for the Preparation of Oxazolidine Compound 4

To a mixture of compound (s)-3 (1 mmol) and molecular sieves (150 mg) in dried $CH_2Cl_2$ (5 mL) was added dropwise an appropriate aldehyde (1.1 mmol) at $0°$ C. The reaction mixture was then stirred at room temperature for over 24 h. When the reaction was complete as checked by TLC, the reaction mixture was filtered and concentrated in vacuum. The crude oxazolidine product was purified by flash column chromatography on silica gel using ethyl acetate and petroleum ether as eluents. For compounds 4a, 4b, 4g and 4h, two epimers were isolated, but only one of their epimers were obtained for other compounds.

General Procedure for the Preparation of Compound 5

To a mixture of compound 4 (1 mmol) and $NEt_3$ (1.5 mmol) in dried $CH_2Cl_2$ (5 mL) was added dropwise benzoyl chloride (1.1 mmol) at $0°$ C. The reaction mixture was then stirred at room temperature over night. When the reaction was complete as checked by TLC, the mixture was washed with diluted aqueous solution of $H_2SO_4$ and the organic layers were separated and dried over anhydrous $Na_2SO_4$. The solvent was removed in vacuum. The crude product obtained was purified by flash column chromatography on silica gel using ethyl acetate and petroleum ether as eluents.

Example 2

This example illustrates another general synthetic approach for the preparation of 1,3-N,O-oxazolidine derivatives.

General Procedure for the Preparation of Compound (S)-6

To a solution of sodium cyanoborohydride (6 mmol) in methanol (20 mL) were added (S)-methyl 2-amino-4-methylpentanoate (2 mmol) and 5 drops of methyl orange solution. The pH was kept at less than 3 (pink coloration of the indicator) by the dropwise addition of a concentrate HCl solution. After 30 min, the pink color was no longer faded and the reaction mixture was stirred overnight. After removal of the solvent, the residue was slurried with water (5 mL) and the pH was adjusted to 9 by the addition of 20% aqueous potassium hydroxide. The mixture was extracted three times with dichloromethane followed by drying with anhydrous $Na_2SO_4$. A yellow oil was obtained after removal of the solvent and was purified by flash column chromatography on silica gel using ethyl acetate and petroleum ether as eluents.

General Procedure for the Preparation of Compound (S)-7

A freshly prepared solution of Grignard reagent (6.2 mmol) in THF was added dropwise to a solution of (S)-6 (2 mmol) in THF (10 mL) under a nitrogen atmosphere at 0° C. The reaction mixture was then stirred at room temperature over 4 h. When the reaction was complete as checked by TLC, the mixture was cooled to 0° C. and a saturated cold aqueous solution of $NH_4Cl$ was added dropwise into the mixture under vigorous stirring. The mixture was then extracted three times with EtOAc or ether. The solvent was combined and washed with brine and dried with anhydrous $Na_2SO_4$. The solution was concentrated in vacuum and the residue containing crude amino alcohol was purified by flash column chromatography on silica gel using ethyl acetate and methanol as eluents.

General Procedure for the Preparation of Oxazolidine Compound (S)-8

To a mixture of compound (S)-7 (1 mmol) and molecular sieves (150 mg) in anhydrous $CH_2Cl_2$ (5 mL) was added dropwise an appropriate aldehyde (1.1 mmol) at 0° C. The reaction was stirred at room temperature for over 24 h. When the reaction was complete as checked by TLC, the reaction mixture was filtered and concentrated in vacuum. The crude oxazolidine compound (S)-8 was purified by flash column chromatography on silica gel with ethyl acetate and petroleum ether as eluents.

Example 3

Synthesis of (2R,4S)-2,5,5-triethyl-4-isobutyloxazolidine (4a-1)

Compound 4a-1 was synthesized according to the procedures described in Examples 1 or 2. The yield is 8.9%. $^1$H NMR (500 MHz, $CDCl_3$): δ4.41 (1H, t, J=6.5 Hz), 2.89 (1H, t, J=7.1 Hz), 1.85-1.40 (9H, m), 0.94 (15H, m); $^{13}$C NMR (125 MHz, $CDCl_3$): δ95.4, 86.1, 64.6, 37.6, 29.7, 18.3, 17.8, 17.7, 16.9, 16.8, 16.6, 9.0, 8.9; MS (FAB-): 212 (M–H$^+$).

Example 4

Synthesis of (2S,4S)-2,5,5-triethyl-4-isobutyloxazolidine (4a-2)

Compound 4a-2 was synthesized according to the procedures described in Examples 1 or 2. The yield is 19.0%.
$^1$H NMR (500 MHz, $CDCl_3$): δ4.32 (1H, t, J=6.0 Hz), 2.76 (1H, t, J=7.2 Hz), 1.85-1.40 (9H, m), 0.94 (15H, m); $^{13}$C NMR (125 MHz, $CDCl_3$): δ 93.5, 82.1, 64.6, 37.6, 29.7, 18.3, 17.8, 17.7, 16.9, 16.8, 16.6, 9.0, 8.9; MS (FAB-): 212 (M–H$^+$).

Example 5

Synthesis of (2R,4S)-5,5-diethyl-4-isobutyl-2-propyloxazolidine (4b-1)

Compound 4b-1 was synthesized according to the procedures described in Examples 1 or 2. The yield is 6.8%. $C_{14}H_{29}NO$, $^1$H NMR (400 MHz, $CDCl_3$): δ4.52 (1H, t, J=5.1 Hz), 2.63 (1H, t, J=6.5 Hz), 1.65-1.40 (11H, m), 0.91 (15H, m); $^{13}$C NMR (100 MHz, $CDCl_3$): δ94.2, 86.5, 66.3, 38.6, 35.7, 26.3, 23.8, 21.7, 16.9, 16.8, 16.6, 9.0, 8.3; MS (FAB-): 226 (M–H$^+$).

Example 6

Synthesis of (2S,4S)-5,5-diethyl-4-isobutyl-2-propyloxazolidine (4b-2)

Compound 4b-2 was synthesized according to the procedures described in Examples 1 or 2. The yield is 23.0%. $C_{14}H_{29}NO$, $^1$H NMR (400 MHz, $CDCl_3$): δ4.40 (1H, t, J=5.1 Hz), 2.89 (1H, t, J=6.5 Hz), 1.65-1.40 (11H, m), 0.93 (15H, m); $^{13}$C NMR (100 MHz, $CDCl_3$): δ96.8, 88.0, 68.7, 38.6, 35.7, 26.3, 23.8, 21.7, 16.9, 16.8, 16.6, 9.0, 8.9; MS (FAB-): 226 (M–H$^+$).

Example 7

Synthesis of (2S,4S)-5,5-diethyl-4-isobutyl-2-phenyloxazolidine (4c)

Compound 4c was synthesized according to the procedures described in Examples 1 or 2. The yield is 36.0%. $C_{17}H_{27}NO$, $^1$H NMR (500 MHz, $CDCl_3$): δ7.93 (1H, d, J=7.5), 7.32 (5H, m), 3.07 (1H, t, J=6.0 Hz), 1.83 (1H, m), 1.36 (6H, m), 0.95 (12H, m) $^{13}$C NMR (125 MHz, $CDCl_3$): δ141.5, 129.0, 128.8, 127.2, 96.8, 90.1, 66.7, 38.6, 25.5, 24.8, 22.7, 9.1, 9.0. MS (FAB-): 260 (M–H$^+$).

Example 8

Synthesis of (2S,4S)-2-ethyl-4-isobutyl-5,5-dipropyloxazolidine (4d)

Compound 4d was synthesized according to the procedures described in Examples 1 or 2. The yield is 32.0%. $C_{15}H_{31}NO$, $^1$H NMR (500 MHz, $CDCl_3$): δ4.01 (1H, t, J=5.1 Hz), 2.90 (1H, t, J=6.5 Hz), 1.85-1.46 (13H, m), 0.94 (15H, m); $^{13}$C NMR (125 MHz, $CDCl_3$): δ90.7, 88.0, 67.7, 38.6, 35.7, 26.3, 23.8, 21.7, 17.9, 17.8, 14.6, 9.0, 8.9. MS (FAB-): 240 (M–H$^+$).

Example 9

Synthesis of (2S,4S)-4-isobutyl-2,5,5-tripropyloxazolidine (4e)

Compound 4e was synthesized according to the procedures described in Examples 1 or 2. The yield is 28.0%. $C_{16}H_{33}NO$, $^1$H NMR (500 MHz, $CDCl_3$): δ4.41 (1H, t, J=6.1 Hz), 2.90 (1H, t, J=6.5 Hz), 1.85-1.36 (15H, m), 0.94 (15H, m); $^{13}$C NMR (125 MHz, $CDCl_3$): δ90.7, 88.0, 67.7, 39.6, 38.7, 35.7, 26.3, 23.8, 22.0, 18.9, 17.8, 15.6, 14.9, 14.8; MS (FAB-): 254 (M–H$^+$).

Example 10

Synthesis of (2S,4S)-4-isobutyl-2-phenyl-5,5-dipropyloxazolidine (4f)

Compound 4f was synthesized according to the procedures described in Examples 1 or 2. The yield is 39.0%. $C_{19}H_{31}NO$, $^1H$ NMR (500 MHz, $CDCl_3$): δ7.93 (1H, d, J=7.5 Hz), 7.41 (5H, m), 3.08 (1H, t, J=6.5 Hz), 1.63 (1H, m), 1.48 (10H, m), 0.96 (12H, m); $^{13}C$ NMR (125 MHz, $CDCl_3$): δ 141.5, 129.0, 128.8, 127.2, 94.8, 89.0, 66.7, 38.6, 35.5, 25.5, 24.8, 22.7, 16.7, 15.6; MS (FAB-): 288 (M–H$^+$).

Example 11

Synthesis of ((2S,4S)-5,5-diethyl-4-isobutyl-2-propyloxazolidin-3-yl)(phenyl)methanone (5a)

Compound 5a was synthesized according to the procedures described in Examples 1 or 2. The yield is 19.0%. $C_{20}H_{31}NO_2$, $^1H$ NMR (400 MHz, $CDCl_3$): δ7.88 (2H, m), 7.45 (3H, m), 4.90 (1H, t, J=6.2 Hz), 3.8 (1H, t, J=5.5 Hz), 1.84 (3H, m), 1.45 (6H, m), 1.02-0.84 (15H, m), $^{13}C$ NMR (100 MHz, $CDCl_3$): δ168.5, 135.5, 129.2, 128.5, 126.9, 93.9, 86.6, 80.1, 37.3, 27.8, 24.8, 23.9, 22.6, 9.6, 8.6; MS (FAB-): 316 (M–H$^+$).

Example 12

Synthesis of ((2S,4S)-5,5-diethyl-4-isobutyl-2-propyloxazolidin-3-yl)(phenyl)methanone (5b)

Compound 5b was synthesized according to the procedures described in Examples 1 or 2. The yield is 18.0%. $C_{21}H_{33}NO_2$, $^1H$ NMR (400 MHz, $CDCl_3$): δ8.08 (2H, m), 7.55 (3H, m), 4.90 (1H, t, J=6.2 Hz), 3.80 (1H, t, J=5.5 Hz), 1.84-1.63 (9H, m), 1.35 (2H, m), 1.02-0.84 (15H, m), $^{13}C$ NMR (100 MHz, $CDCl_3$): δ 168.5, 135.5, 129.2, 128.5, 126.9, 93.9, 85.6, 81.6, 37.3, 35.6, 27.8, 24.8, 23.9, 22.6, 22.1, 17.8, 15.6, 9.6, 8.6; MS (FAB-): 330 (M–H$^+$).

Example 13

Synthesis of ((2S,4S)-2-ethyl-4-isobutyl-5,5-dipropyloxazolidin-3-yl)(phenyl)methanone (5c)

Compound 5c was synthesized according to the procedures described in Examples 1 or 2. The yield is 16.0%. $C_{22}H_{35}NO_2$, $^1H$ NMR (400 MHz, $CDCl_3$): δ8.06 (2H, m), 7.55 (3H, m), 4.90 (1H, t, J=6.2 Hz), 3.78 (1H, t, J=5.5 Hz), 1.94-1.63 (5H, m), 1.45 (8H, m), 0.96 (15H, m), $^{13}C$ NMR (100 MHz, $CDCl_3$): δ 169.3, 135.2, 129.7, 128.5, 126.9, 90.9, 86.6, 82.5, 37.4, 35.6, 27.8, 24.8, 23.9, 23.1, 17.8, 15.6, 15.1, 9.6; MS (FAB-): 344 (M–H$^+$).

Example 14

Synthesis of ((2S,4S)-4-isobutyl-2,5,5-tripropyloxazolidin-3-yl)(phenyl)methanone (5d)

Compound 5d was synthesized according to the procedures described in Examples 1 or 2. The yield is 11.0%. $C_{23}H_{37}NO_2$, $^1H$ NMR (500 MHz, $CDCl_3$): δ7.88 (2H, m), 7.36 (3H, m), 4.94 (1H, t, J=6.2 Hz), 3.83 (1H, t, J=5.5 Hz), 1.64 (5H, m), 1.45-1.28 (10H, m), 0.96 (15H, m), $^{13}C$ NMR (125 MHz, $CDCl_3$): δ 167.9, 135.2, 129.7, 128.5, 126.9, 89.8, 85.2, 81.9, 37.4, 35.6, 35.2, 34.1, 27.8, 24.8, 23.9, 17.8, 17.2, 15.6, 15.1, 14.2, 14.0; MS (FAB-): 358 (M–H$^+$).

Example 15

Synthesis of (2R,4S)-4-sec-butyl-2,5,5-triethyloxazolidine (4g-1)

Compound 4g-1 was synthesized according to the procedures described in Examples 1 or 2. The yield is 7.1%. $^1H$ NMR (500 MHz, $CDCl_3$): δ4.23 (1H, t, J=6.0 Hz), 2.79 (1H, t, J=7.2 Hz), 1.87 (1H, m), 1.56 (9H, m), 0.94 (15H, m); $^{13}C$ NMR (125 MHz, $CDCl_3$): δ96.4, 91.2, 72.3, 37.6, 33.7, 27.1, 26.7, 26.0, 18.3, 16.6, 9.1, 9.0, 8.9; MS (FAB-): 212 (M–H$^+$).

Example 16

Synthesis of (2S,4S)-4-sec-butyl-2,5,5-triethyloxazolidine (4g-2)

Compound 4g-2 was synthesized according to the procedures described in Examples 1 or 2. The yield is 21.1%. $^1H$ NMR (500 MHz, $CDCl_3$): δ4.01 (1H, t, J=5.1 Hz), 2.82 (1H, t, J=6.0 Hz), 1.88 (1H, m), 1.56 (9H, m), 0.96 (15H, m); $^{13}C$ NMR (125 MHz, $CDCl_3$): δ94.7, 90.8, 73.6, 37.6, 33.7, 27.1, 26.7, 26.0, 18.3, 16.6, 9.1, 8.9, 8.8; MS (FAB-): 212 (M–H$^+$).

Example 17

Synthesis of (2R,4S)-4-sec-butyl-5,5-diethyl-2-propyloxazolidine (4h-1)

Compound 4h-1 was synthesized according to the procedures described in Examples 1 or 2. The yield is 6.7%. $^1H$ NMR (500 MHz, $CDCl_3$): δ4.52 (1H, t, J=6.0 Hz), 2.86 (1H, t, J=7.2 Hz), 1.88 (1H, m), 1.56 (9H, m), 1.38 (2H, m), 0.94 (15H, m); $^{13}C$ NMR (125 MHz, $CDCl_3$): δ95.1, 90.9, 74.0, 38.6, 33.7, 27.1, 26.7, 26.0, 18.3, 16.6, 14.6, 10.3, 8.9, 8.7; MS (FAB-): 226 (M–H$^+$).

Example 18

Synthesis of (2S,4S)-4-sec-butyl-5,5-diethyl-2-propyloxazolidine (4h-2)

Compound 4h-2 was synthesized according to the procedures described in Examples 1 or 2. The yield is 23.1%. $^1H$ NMR (500 MHz, $CDCl_3$): δ4.41 (1H, t, J=6.5 Hz), 2.90 (1H, t, J=7.0 Hz), 1.88 (1H, m), 1.56 (9H, m), 1.38 (2H, m), 0.96 (15H, m); $^{13}C$ NMR (125 MHz, $CDCl_3$): δ95.6, 91.8, 74.1, 38.6, 33.7, 27.1, 26.7, 26.0, 18.3, 16.6, 14.6, 10.1, 8.9, 8.8; MS (FAB-): 226 (M–H$^+$).

Example 19

Synthesis of (2S,4S)-4-sec-butyl-5,5-diethyl-2-phenyloxazolidine (4i)

Compound 4i was synthesized according to the procedures described in Examples 1 or 2. The yield is 35%. $C_{17}H_{27}NO$, $^1H$ NMR (400 MHz, $CDCl_3$): δ7.93 (1H, d, J=7.5 Hz), 7.38 (5H, m), 3.06 (1H, t, J=6.5 Hz), 1.80 (1H, m), 1.63-1.47 (6H, m), 0.96 (12H, m); $^{13}C$ NMR (100 MHz, $CDCl_3$): δ 141.5, 129.0, 128.8, 127.2, 95.6, 90.1, 71.2, 33.6, 26.5, 23.8, 22.7, 17.1, 11.2, 9.0; MS (FAB-): 260 (M–H$^+$).

Example 20

Synthesis of (2S,4S)-4-sec-butyl-2-ethyl-5,5-dipropyloxazolidine (4j)

Compound 4j was synthesized according to the procedures described in Examples 1 or 2. The yield is 24%. $C_{15}H_{31}NO$, $^1H$ NMR (500 MHz, $CDCl_3$): δ4.41 (1H, t, J=5.1 Hz), 2.90 (1H, t, J=6.5 Hz), 1.88 (1H, m), 1.65-1.36 (12H, m), 0.94 (15H, m); $^{13}C$ NMR (125 MHz, $CDCl_3$): δ90.7, 88.0, 74.1, 38.6, 35.7, 35.0, 30.1, 26.3, 18.3, 17.9, 17.8, 14.7, 14.2, 11.6, 9.6; MS (FAB-): 240 (M–H$^+$).

Example 21

Synthesis of (2S,4S)-4-sec-butyl-2,5,5-tripropyloxazolidine (4k)

Compound 4k was synthesized according to the procedures described in Examples 1 or 2. The yield is 22.0%. $C_{16}H_{33}NO$, $^1H$ NMR (500 MHz, $CDCl_3$): δ4.40 (1H, t, J=5.1 Hz), 2.93 (1H, t, J=6.5 Hz), 1.83 (1H, m), 1.65-1.36 (14H, m), 0.96 (15H, m); $^{13}C$ NMR (125 MHz, $CDCl_3$): δ90.2, 88.2, 74.3, 38.6, 35.7, 35.0, 32.3, 26.3, 18.8, 17.9, 17.8, 16.5, 15.2, 14.7, 14.2, 12.6; MS (FAB-): 254 (M–H$^+$).

Example 22

Synthesis of (2S,4S)-4-sec-butyl-2-phenyl-5,5-dipropyloxazolidine (4l)

Compound 4l was synthesized according to the procedures described in Examples 1 or 2. The yield is 30.0%. $C_{19}H_{31}NO$, $^1H$ NMR (400 MHz, $CDCl_3$): δ8.03 (1H, d, J=7.5 Hz), 7.38 (5H, m), 2.96 (1H, t, J=6.5 Hz), 1.80 (1H, m), 1.63-1.47 (10H, m), 0.96 (12H, m); $^{13}C$ NMR (100 MHz, $CDCl_3$): δ 141.4, 129.0, 128.8, 127.2, 92.1, 89.1, 75.2, 36.4, 35.9, 33.6, 26.5, 18.7, 17.1, 16.7, 14.7, 13.8, 11.0; MS (FAB-): 288 (M–H$^+$).

Example 23

Synthesis of ((2S,4S)-4-sec-butyl-2,5,5-triethyloxazolidin-3-yl)(phenyl)methanone (5e)

Compound 5e was synthesized according to the procedures described in Examples 1 or 2. The yield is 14.0%. $C_{20}H_{31}NO_2$, $^1H$ NMR (500 MHz, $CDCl_3$): δ, 8.08 (2H, m), 7.55 (3H, m), 4.90 (1H, t, J=5.6 Hz), 3.80 (1H, t, J=4.0 Hz), 2.30 (1H, m), 1.83-1.45 (8H, m), 0.96 (15H, m), $^{13}C$ NMR (125 MHz, $CDCl_3$): δ, 167.5, 135.5, 129.2, 128.5, 126.9, 93.9, 86.6, 78.2, 31.2, 27.8, 26.7, 24.8, 23.9, 19.3, 12.7, 9.6, 8.6, 8.3; MS (FAB-): 316 (M–H$^+$).

Example 24

Synthesis of ((2S,4S)-4-sec-butyl-2-ethyl-5,5-dipropyloxazolidin-3-yl)(phenyl)methanone (5f)

Compound 5f was synthesized according to the procedures described in Examples 1 or 2. The yield is 14.0%. $C_{22}H_{35}NO_2$, $^1H$ NMR (500 MHz, $CDCl_3$): δ8.06 (2H, m), 7.65 (3H, m), 4.90 (1H, t, J=5.6 Hz), 3.83 (1H, t, J=4.0 Hz), 2.30 (1H, m), 1.83-1.65 (4H, m), 1.38 (8H, m), 0.96 (15H, m); $^{13}C$ NMR (125 MHz, $CDCl_3$): δ 168.5, 135.4, 129.2, 128.5, 126.9, 89.9, 84.7, 73.2, 37.5, 36.7, 31.2, 27.8, 26.7, 20.8, 18.3, 17.9, 15.8, 15.3, 12.7, 9.8; MS (FAB-): 344 (M–H$^+$).

Example 25

Synthesis of ((2S,4S)-4-sec-butyl-2,5,5-tripropyloxazolidin-3-yl)(phenyl)methanone (5g)

Compound 5g was synthesized according to the procedures described in Examples 1 or 2. The yield is 30.0%. $C_{23}H_{37}NO_2$, $^1H$ NMR (500 MHz, $CDCl_3$): δ8.06 (2H, m), 7.65 (3H, m), 4.90 (1H, t, J=5.6 Hz), 3.83 (1H, t, J=4.0 Hz), 2.27 (1H, m), 1.83-1.65 (4H, m), 1.38 (10H, m), 0.96 (15H, m); $^{13}C$ NMR (125 MHz, $CDCl_3$): δ 168.9, 135.5, 129.2, 128.5, 126.9, 89.9, 84.7, 73.2, 37.5, 36.7, 36.1, 30.1, 26.7, 18.3, 17.9, 17.2, 16.5, 15.8, 15.3, 13.7, 12.7; MS (FAB-): 358 (M+H$^+$).

Example 26

Synthesis of (2S,4S)-4-benzyl-2,5,5-triethyloxazolidine (4m)

Compound 4m was synthesized according to the procedures described in Examples 1 or 2. The yield is 21.0%. $C_{16}H_{25}NO$, $^1H$ NMR (400 MHz, $CDCl_3$): δ7.31 (2H, m), 7.19 (3H, m), 4.10 (1H, t, J=5.1 Hz), 3.52 (1H, t, J=4.9 Hz), 2.76 (1H, m), 2.56 (1H, m), 1.58 (2H, m), 1.42 (4H, m), 0.96 (9H, m); $^{13}C$ NMR (100 MHz, $CDCl_3$): δ 138.7, 128.7, 128.1, 125.8, 93.1, 87.2, 78.2, 35.2, 31.6, 23.5, 22.1, 9.0, 8.9; MS (FAB-): 246 (M–H$^+$).

Example 27

Synthesis of (2S,4S)-4-benzyl-5,5-diethyl-2-propyloxazolidine (4n)

Compound 4l was synthesized according to the procedures described in Examples 1 or 2. The yield is 23.0%. $C_{17}H_{27}NO$, $^1H$ NMR (400 MHz, $CDCl_3$): δ7.33 (2H, m), 7.29 (3H, m), 4.05 (1H, t, J=5.1 Hz), 3.50 (1H, t, J=4.9 Hz), 2.76 (1H, m), 2.54 (1H, m), 1.50 (2H, m), 1.42-1.28 (6H, m), 0.96 (9H, m); $^{13}C$ NMR (100 MHz, $CDCl_3$): δ 138.6, 128.7, 128.1, 125.8, 94.5, 87.2, 77.2, 37.8, 32.6, 23.5, 22.8, 15.9, 13.3, 9.0; MS (FAB-): 260 (M–H$^+$).

Example 28

Synthesis of (2S,4S)-4-benzyl-2-ethyl-5,5-dipropyloxazolidine (4o)

Compound 4o was synthesized according to the procedures described in Examples 1 or 2. The yield is 20.0%. $C_{18}H_{29}NO$, $^1H$ NMR (400 MHz, $CDCl_3$): δ7.38 (2H, m), 7.28 (3H, m), 4.02 (1H, t, J=5.1 Hz), 3.47 (1H, t, J=4.9 Hz), 2.78 (1H, m), 2.54 (1H, m), 1.80 (2H, m), 1.42-1.28 (8H, m), 0.92 (9H, m); $^{13}C$ NMR (100 MHz, $CDCl_3$): δ 138.6, 128.7, 128.1, 125.8, 93.7, 89.2, 75.2, 37.8, 34.6, 34.1, 31.8, 18.9, 18.0, 14.4, 13.3, 9.0; MS (FAB-): 274 (M–H$^+$).

Example 29

Synthesis of (2S,4S)-4-benzyl-2,5,5-tri-propyloxazolidine (4p)

Compound 4p was synthesized according to the procedures described in Examples 1 or 2. The yield is 18.0%. $C_{19}H_{31}NO$, $^1H$ NMR (400 MHz, $CDCl_3$): δ7.38 (2H, m), 7.29 (3H, m), 3.98 (1H, t, J=5.1 Hz), 3.41 (1H, t, J=4.9 Hz), 2.76 (1H, m), 2.54 (1H, m), 1.50 (2H, m), 1.42-1.28 (10H, m), 0.94 (9H, m); $^{13}$C NMR (100 MHz, CDCl$_3$): δ 138.6, 128.7, 128.1, 125.6, 91.6, 87.2, 76.7, 37.8, 35.6, 35.2, 33.6, 18.1, 17.2, 15.9, 14.7, 13.3, 12.7; MS (FAB-): 288 (M–H$^+$).

Example 30

Synthesis of (2S,4S)-2,3-diethyl-4-isobutyl-5,5-diphenyloxazolidine (8a)

Compound 8a was synthesized according to the procedures described in Examples 1 or 2. The yield is 43.0%. C$_{23}$H$_{31}$NO, $^1$H NMR (400 MHz, CDCl$_3$): δ7.46 (4H, m), 7.38 (6H, m), 4.02 (1H, t, J=6.0 Hz), 3.76 (1H, t, J=7.2 Hz), 2.58 (1H, m), 2.46 (1H, m), 1.68 (3H, m), 1.33 (2H, m), 1.06 (3H, t, J=7.2 Hz), 0.91 (9H, m); $^{13}$C NMR (100 MHz, CDCl$_3$): δ 141.1 129.7, 128.7, 128.3, 126.8, 126.2, 98.9, 93.5, 78.2, 48.7, 36.7, 27.3, 26.7, 22.3, 21.7, 14.1, 10.3; MS (FAB-): 336 (M–H$^+$).

Example 31

Synthesis of (2S,4S)-3-ethyl-4-isobutyl-5,5-diphenyl-2-propyloxazolidine (8b)

Compound 8b was synthesized according to the procedures described in Examples 1 or 2. The yield is 15.0%. C$_{24}$H$_{33}$NO, $^1$H NMR (400 MHz, CDCl$_3$): δ7.48 (4H, m), 7.36 (6H, m), 4.12 (1H, t, J=6.0 Hz), 3.80 (1H, t, J=7.2 Hz), 2.60 (1H, m), 2.50 (1H, m), 1.68 (3H, m), 1.33 (4H, m), 1.08 (3H, t, J=7.2 Hz), 0.90 (9H, m); $^{13}$C NMR (100 MHz, CDCl$_3$): δ 142.0, 141.1 129.7, 128.7, 128.3, 126.8, 126.2, 98.1, 90.1, 78.2, 48.7, 37.6, 33.2, 27.3, 21.1, 20.8, 18.7, 14.1, 11.7; MS (FAB-): 350 (M–H$^+$).

Example 32

Synthesis of (2S,4S)-5,5-dibutyl-2-ethyl-4-isobutyl-3-propyloxazolidine (8c)

Compound 8c was synthesized according to the procedures described in Examples 1 or 2. The yield is 11.0%. C$_{20}$H$_{41}$NO, $^1$H NMR (500 MHz, CDCl$_3$): δ 4.01 (1H, t, J=6.0 Hz), 2.98 (1H, t, J=6.5 Hz), 2.55 (2H, m), 1.65 (3H, m), 1.45-1.25 (16H, m), 0.96 (18H, m); $^{13}$C NMR (125 MHz, CDCl$_3$): δ94.5, 89.9, 73.2, 49.7, 35.8, 34.3, 33.6, 27.9, 27.5, 27.1, 26.5, 24.3, 23.6, 23.4, 23.2, 21.9, 14.3, 14.0, 11.2, 10.5; MS (FAB-): 310 (M–H$^+$).

Example 33

Synthesis of (2S,4S)-5,5-dibutyl-4-isobutyl-2,3-dipropyloxazolidine (8d)

Compound 41 was synthesized according to the procedures described in Examples 1 or 2. The yield is 14.0%. C$_{21}$H$_{43}$NO, $^1$H NMR (500 MHz, CDCl$_3$): δ 4.10 (1H, t, J=6.0 Hz), 2.98 (1H, t, J=6.5 Hz), 2.45 (2H, m), 1.65 (3H, m), 1.45-1.25 (18H, m), 0.96 (18H, m); $^{13}$C NMR (125 MHz, CDCl$_3$): δ91.2, 89.4, 74.2, 49.1, 36.8, 35.8, 34.3, 33.6, 27.9, 27.1, 26.5, 24.3, 23.6, 23.4, 23.2, 21.9, 18.9, 14.7, 14.3, 14.0, 11.5; MS (FAB-): 324 (M–H$^+$).

Example 34

Synthesis of (2S,4S)-2,3,5,5-tetraethyl-4-isobutyloxazolidine (8e)

Compound 8e was synthesized according to the procedures described in Examples 1 or 2. The yield is 17.0%. C$_{15}$H$_{31}$NO, $^1$H NMR (500 MHz, CDCl$_3$): δ3.98 (1H, t, J=6.5 Hz), 2.89 (1H, t, J=7.2 Hz), 2.38 (2H, q, J=8.0 Hz), 1.84-1.45 (7H, m), 1.35 (2H, m), 1.02 (3H, t, J=7.8 Hz), 0.96 (15H, m); $^{13}$C NMR (125 MHz, CDCl$_3$): δ95.5, 88.7, 71.2, 47.6, 35.8, 28.3, 26.7, 25.4, 25.0, 23.1, 22.4, 14.7, 11.2, 9.2, 8.9; MS (FAB-): 240 (M–H$^+$).

Example 35

Synthesis of (2S,4S)-3,5,5-triethyl-4-isobutyl-2-propyloxazolidine (8f)

Compound 8f was synthesized according to the procedures described in Examples 1 or 2. The yield is 15.0%. C$_{16}$H$_{33}$NO, $^1$H NMR (500 MHz, CDCl$_3$): δ4.01 (1H, t, J=6.5 Hz), 2.89 (1H, t, J=7.2 Hz), 2.38 (2H, q, J=8.0 Hz), 1.84-1.45 (7H, m), 1.35 (4H, m), 1.02 (3H, t, J=7.8 Hz), 0.96 (15H, m); $^{13}$C NMR (125 MHz, CDCl$_3$): δ94.3, 86.7, 70.1, 47.6, 37.5, 35.8, 28.3, 26.7, 25.4, 23.1, 22.4, 18.7, 14.7, 12.7, 9.2, 8.9; MS (FAB-): 254 (M–H$^+$).

Example 36

Synthesis of (2S,4S)-3,5,5-triethyl-4-isobutyl-2-phenyloxazolidine (8g)

Compound 8g was synthesized according to the procedures described in Examples 1 or 2. The yield is 18.0%. C$_{19}$H$_{31}$NO, $^1$H NMR (400 MHz, CDCl$_3$): δ7.36 (5H, m), 5.62 (1H, s), 3.02 (1H, t, J=6.5 Hz), 2.38 (2H, q, J=8.0 Hz), 1.84-1.45 (5H, m), 1.35 (2H, m), 1.02 (3H, t, J=7.8 Hz), 0.96 (12H, m); $^{13}$C NMR (100 MHz, CDCl$_3$): δ 141.7, 129.2, 128.8, 128.4, 96.4, 92.7, 71.2, 43.5, 37.8, 27.8, 26.7, 25.4, 23.1, 22.8, 18.7, 11.2, 9.0; MS (FAB-): 288 (M–H$^+$).

Example 37

Synthesis of (2S,4S)-2-butyl-5,5-diethyl-4-isobutyloxazolidine (LC-02d-01)

Compound (LC-02d-01) was synthesized according to the procedures described in Examples 1 or 2. $^1$H NMR (500 MHz, CDCl$_3$): δ4.46 (1H, t, J=6.0 Hz), 2.80 (1H, t, J=6.8 Hz), 1.80-1.30 (15H, m), 0.91 (15H, m); $^{13}$C NMR (100 MHz, CDCl$_3$): δ94.9, 86.0, 65.0, 38.0, 35.7, 26.3, 23.8, 22.7, 21.7, 18.9, 16.9, 16.8, 16.6, 9.0, 8.9; C$_{15}$H$_{31}$NO, FW=241.

Example 38

Synthesis of (2S,4S)-5,5-diethyl-4-isobutyl-2-pentyloxazolidine (LC-02d-02)

Compound (LC-02d-02) was synthesized according to the procedures described in Examples 1 or 2. $^1$H NMR (400 MHz, CDCl$_3$): δ4.50 (1H, t, J=5.3 Hz), 2.61 (1H, t, J=6.5 Hz), 1.65-1.30 (17H, m), 0.93 (15H, m); $^{13}$C NMR (100 MHz, CDCl$_3$): δ94.1, 86.4, 66.0, 38.5, 35.9, 31.8, 26.0, 23.5, 21.4, 20.8, 16.9, 16.8, 16.6, 9.0, 8.9. C$_{16}$H$_{33}$NO, FW=255

Example 39

Synthesis of (2S,4S)-5,5-diethyl-4-isobutyl-2-p-tolyloxazolidine (LC-02d-03)

Compound (LC-02d-03) was synthesized according to the procedures described in Examples 1 or 2. $^1$H NMR (500 MHz, CDCl$_3$): δ7.91 (1H, d, J=7.3), 7.30 (4H, m), 3.05 (1H, t, J=6.3 Hz), 2.37 (3H, s), 1.85 (1H, m), 1.32 (6H, m), 0.94 (12H, m). $^{13}$C NMR (125 MHz, CDCl$_3$): δ 138.8, 136.9, 128.8, 128.0, 96.5, 90.4, 66.9, 38.4, 25.4, 24.8, 22.6, 22.0, 21.3, 9.1, 9.0. C$_{18}$H$_{29}$NO, FW=275.

Example 40

Synthesis of (2S,4S)-5,5-diethyl-4-isobutyl-2-m-tolyloxazolidine (LC-02d-04)

Compound (LC-02d-04) was synthesized according to the procedures described in Examples 1 or 2. $^1$H NMR (500 MHz, CDCl$_3$): δ7.98 (1H, d, J=7.1), 7.30 (4H, m), 3.07 (1H, t, J=6.1 Hz), 2.35 (3H, s), 1.80 (1H, m), 1.35 (6H, m), 0.91 (12H, m). $^{13}$C NMR (125 MHz, CDCl$_3$): δ 138.9, 135.4, 129.8, 128.4, 127.5, 125.0, 96.6, 90.7, 66.8, 38.3, 25.3, 24.9, 22.5, 21.6, 21.3, 9.1, 9.0. C$_{18}$H$_{29}$NO, FW=275.

Example 41

Synthesis of (2S,4S)-4-benzyl-2-butyl-5,5-diethyloxazolidine (LC-02d-05)

Compound (LC-02d-05) was synthesized according to the procedures described in Examples 1 or 2. $^1$H NMR (400 MHz, CDCl$_3$): δ7.30 (5H, m), 4.08 (1H, t, J=5.1 Hz), 3.51 (1H, t, J=4.9 Hz), 2.7-2.50 (2H, m), 1.6-1.3 (10H, m), 0.96 (9H, m); $^{13}$C NMR (100 MHz, CDCl$_3$): δ 138.6, 128.7, 128.1, 125.8, 94.5, 87.2, 77.2, 37.8, 32.6, 23.5, 22.8, 15.9, 13.3, 9.0, 8.9. C$_{18}$H$_{29}$NO, FW=275.

Example 42

Synthesis of (2S,4S)-4-benzyl-5,5-diethyl-2-pentyloxazolidine (LC-02d-06)

Compound (LC-02d-6) was synthesized according to the procedures described in Examples 1 or 2. $^1$H NMR (400 MHz, CDCl$_3$): δ7.31 (5H, m), 4.06 (1H, t, J=5.1 Hz), 3.54 (1H, t, J=4.9 Hz), 2.7-2.50 (2H, m), 1.6-1.3 (12H, m), 0.94 (9H, m); $^{13}$C NMR (100 MHz, CDCl$_3$): δ 138.7, 128.7, 128.0, 125.7, 94.4, 87.1, 77.1, 37.8, 32.6, 31.7, 23.5, 22.8, 21.2, 15.9, 13.3, 9.0. C$_{19}$H$_{31}$NO, FW=289.

Example 43

Synthesis of (2S,4S)-4-benzyl-5,5-diethyl-2-phenyloxazolidine (LC-02d-07)

Compound (LC-02d-07) was synthesized according to the procedures described in Examples 1 or 2. $^1$H NMR (400 MHz, CDCl$_3$): δ7.93 (1H, J=6.5 Hz) 7.50-7.10 (9H, m), 3.42 (1H, t, J=4.9 Hz), 2.7-2.5 (2H, m), 1.6-1.4 (4H, m), 0.94 (6H, m); $^{13}$C NMR (100 MHz, CDCl$_3$): δ 141.5, 138.7, 128.7, 128.6, 128.1, 128.0, 125.8, 92.7, 89.0, 73.6, 35.2, 32.6, 23.5, 8.9. C$_{20}$H$_{25}$NO, FW=295.

Example 44

Synthesis of (2S,4S)-4-benzyl-5,5-diethyl-2-p-tolyloxazolidine (LC-02d-08)

Compound (LC-02d-08) was synthesized according to the procedures described in Examples 1 or 2. $^1$H NMR (400 MHz, CDCl$_3$): δ7.91 (1H, J=6.4 Hz) 7.50-7.10 (8H, m), 3.45 (1H, t, J=5.1 Hz), 2.7-2.5 (2H, m), 2.38 (3H, s), 1.6-1.4 (4H, m), 0.94 (6H, m); $^{13}$C NMR (100 MHz, CDCl$_3$): δ 141.5, 138.7, 128.7, 128.6, 128.1, 128.0, 125.8, 92.7, 89.0, 73.7, 35.2, 32.6, 23.5, 8.9. C$_{21}$H$_{27}$NO, FW=309.

Example 45

Synthesis of (2S,4S)-4-benzyl-5,5-diethyl-2-m-tolyloxazolidine (LC-02d-09)

Compound (LC-02d-09) was synthesized according to the procedures described in Examples 1 or 2. $^1$H NMR (400 MHz, CDCl$_3$): δ7.92 (1H, J=6.4 Hz) 7.50-7.10 (8H, m), 3.46 (1H, t, J=5.0 Hz), 2.8-2.5 (2H, m), 2.4 (3H, s), 1.6-1.4 (4H, m), 0.94 (6H, m); $^{13}$C NMR (100 MHz, CDCl$_3$): δ 138.7, 138.4, 135.2, 130.0, 128.7, 128.5, 128.1, 128.0, 125.8, 92.7, 89.0, 73.7, 35.2, 32.6, 22.6, 8.9. C$_{21}$H$_{27}$NO, FW=309.

Example 46

Synthesis of (2S,4S)-4-benzyl-2-butyl-5,5-dipropyloxazolidine (LC-02d-10)

Compound (LC-02d-10) was synthesized according to the procedures described in Examples 1 or 2. $^1$H NMR (400 MHz, CDCl$_3$): δ7.40-7.20 (5H, m), 3.97 (1H, t, J=5.1 Hz), 3.40 (1H, t, J=4.9 Hz), 2.7-2.5 (2H, m), 1.5-1.2 (14H, m), 0.94 (9H, m); $^{13}$C NMR (100 MHz, CDCl$_3$): δ 138.6, 128.7, 128.1, 125.6, 91.6, 87.2, 76.7, 37.8, 35.5, 35.2, 23.6, 22.7, 18.1, 17.2, 15.9, 14.7, 13.3, 12.7. C$_{20}$H$_{33}$NO, FW=303.

Example 47

Synthesis of (2S,4S)-4-benzyl-2-pentyl-5,5-dipropyloxazolidine (LC-02d-11)

Compound (LC-02d-11) was synthesized according to the procedures described in Examples 1 or 2. $^1$H NMR (400 MHz, CDCl$_3$): δ7.40-7.20 (5H, m), 3.96 (1H, t, J=5.2 Hz), 3.40 (1H, t, J=4.9 Hz), 2.7-2.5 (2H, m), 1.5-1.2 (16H, m), 0.93 (9H, m); $^{13}$C NMR (100 MHz, CDCl$_3$): δ138.7, 128.6, 128.2, 125.6, 91.5, 87.1, 76.8, 37.8, 35.5, 35.2, 31.8, 23.5, 22.7, 18.1, 17.2, 15.9, 14.7, 13.3, 12.7. C$_{21}$H$_{35}$NO, FW=317.

Example 48

Synthesis of (2S,4S)-4-sec-butyl-5,5-diethyl-2-p-tolyloxazolidine (LC-02d-12)

Compound (LC-02d-12) was synthesized according to the procedures described in Examples 1 or 2. $^1$H NMR (400 MHz, CDCl$_3$): δ7.93 (1H, d, J=7.4 Hz), 7.35 (4H, m), 3.03 (1H, t, J=6.6 Hz), 2.36 (3H, s), 1.82 (1H, m), 1.63-1.47 (6H, m), 0.96 (12H, m); $^{13}$C NMR (100 MHz, CDCl$_3$): δ 141.5, 136.7, 129.0, 128.8, 95.5, 90.4, 71.2, 33.6, 26.5, 23.8, 22.7, 22.0, 17.1, 11.2, 9.0. C$_{18}$H$_{29}$NO, FW=275.

Example 49

Synthesis of (2S,4S)-4-sec-butyl-5,5-diethyl-2-m-tolyloxazolidine (LC-02d-13)

Compound (LC-02d-13) was synthesized according to the procedures described in Examples 1 or 2. $^1$H NMR (400 MHz, CDCl$_3$): δ7.92 (1H, d, J=7.2 Hz), 7.10-7.50 (4H, m), 3.01 (1H, t, J=6.5 Hz), 2.40 (3H, s), 1.83 (1H, m), 1.63-1.47 (6H, m), 0.91-0.96 (12H, m); $^{13}$C NMR (100 MHz, CDCl$_3$):

δ 138.9, 135.7, 129.9, 128.4, 127.5, 125.1, 95.1, 90.3, 71.3, 33.6, 26.5, 23.8, 22.7, 22.2, 17.1, 11.2, 9.0. $C_{18}H_{29}NO$, FW=275.

Example 50

Synthesis of (2S,4S)-4-sec-butyl-2-butyl-5,5-diethyloxazolidine (LC-02d-14)

Compound (LC-02d-14) was synthesized according to the procedures described in Examples 1 or 2. $^1$H NMR (500 MHz, CDCl$_3$): δ4.40 (1H, t, J=6.5 Hz), 2.91 (1H, t, J=7.0 Hz), 1.88 (1H, m), 1.6-1.3 (13H, m), 0.95 (15H, m); $^{13}$C NMR (125 MHz, CDCl$_3$): δ95.6, 91.8, 74.1, 38.6, 33.7, 27.1, 26.7, 26.0, 22.7, 18.3, 16.6, 14.6, 10.1, 8.9, 8.8. $C_{15}H_{31}NO$, FW=241.

Example 51

Synthesis of (2S,4S)-4-sec-butyl-5,5-diethyl-2-pentyloxazolidine (LC-02d-15)

Compound (LC-02d-15) was synthesized according to the procedures described in Examples 1 or 2. $^1$H NMR (500 MHz, CDCl$_3$): δ4.41 (1H, t, J=6.5 Hz), 2.92 (1H, t, J=7.0 Hz), 1.88 (1H, m), 1.6-1.2 (15H, m), 0.90-0.96 (15H, m); $^{13}$C NMR (125 MHz, CDCl$_3$): δ95.6, 91.8, 74.1, 38.0, 33.7, 31.8, 27.1, 26.7, 26.0, 22.7, 21.0, 18.3, 16.6, 14.6, 10.1, 8.9, 8.8. $C_{16}H_{33}NO$, FW=255.

Example 52

Methods

Assays, Detections and Tests

1. Whole-Cell Patch Clamp

Hippocampal neurons were prepared from embryonic day 18 Sprague-Dawley rats. After the hippocampus had been removed from the brain, isolated cells were plated onto Poly d-Lysine (PDL) (P0899, Sigma)-coated 35 mm dishes (153066, NUNC) at a density of $3\times10^5$ cell per plate using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Half of the medium was changed with NB, B27 and 50 μM L-glutamine every 2 to 3 days. On day 12 in vitro (12 DIV), whole-cell patch clamp was performed. The internal solution contained 120 mM cesium chloride, 20 mM tetraethylammonium chloride, 2 mM magnesium chloride, 1 mM calcium chloride and 10 mM HEPES (pH 7.2). The external solution contained 137 mM sodium chloride, 1 mM sodium bicarbonate, 0.34 mM sodium phosphate dibasic, 5.37 mM potassium chloride, 0.44 mM potassium phosphate monobasic, 2.5 mM HEPES (pH 7.4) and 22.2 mM glucose. Samples mixed with 50 μM NMDA (M3262, Sigma) were arranged in linear array of up to 8 individual controlled pipes (List Medical, Germany) which were connected to solution reservoirs. Memantine (10 μM, M9292, Sigma) was used as a positive control. Pipettes were fire-polished to produce a pipette resistance of 3-5 MΩ. Holding potential of patched cells was kept at −80 mV and currents were recorded using Axopatch-200B amplifier (Axon Instruments, USA). Tetrodotoxin (5 μM) and bicuculline methiodide (20 μM) (0109, Tocris) were present in the bath solution to block synaptic transmission mediated by voltage-gated sodium channels and $Ca^{2+}$ activated potassium channels, respectively. Data was analyzed by pClamp9 software and percentage of inhibition on NMDA-induced current was represented in comparison to solvent control.

2. Neuronal Cultures and Neuron Survival Assay Against NMDA (N-Methyl-D-Aspartic) Insult Primary cortical and hippocampal neurons were prepared from embryonic day 18 (E18) Sprague-Dawley rats. Neurons were plated on 24-well plate (TPP, Corning) at a density of $2\times10^5$ cells per well using Neurobasal medium (Invitrogen) supplemented with 2% B27 (Invitrogen). Neurons at 11-12 days in vitro (12 DIV) were subjected to drug treatment. Neurons were pretreated with the test compound for 2 hours prior to NMDA treatment. 0.1 μM (+)-MK-801 Hydrogen Maleate (Sigma) was added as a positive control. Briefly, the neurons were rinsed with Locke's solution (5 mM potassium chloride, 128 mM sodium chloride, 2.7 mM calcium chloride, 1 mM di-sodium hydrogen orthophosphate, 5 mM HEPES and 10 mM glucose in Milli-Q water) without $Mg^{2+}$, and incubated with addition of glycine (10 μM) for 15 minutes. After the incubation, the neurons were co-treated with the test compound (dissolved in Locke's plus glycine solution) and NMDA (20 μM; Sigma) for 20 minutes. Neurons were rinsed with Locke's plus $Mg^{2+}$ and replaced with fresh growth medium. The cell death was assayed and quantified using the lactate dehydrogenase release assay (Roche) after 24 hours.

3. Immunocytochemical Analysis of Neurons after NMDA Insult

Primary cortical and hippocampal neurons were prepared from embryonic day 18 (E18) Sprague-Dawley rats. Neurons were plated on 35-mm dishes (NUNC) at a density of $1\times10^6$ cells per plate using Neurobasal medium (Invitrogen) supplemented with 2% B27 (Invitrogen). Neurons at 11-12 days in vitro (DIV) were subjected to treatment with the test compounds. Neurons were pretreated with the test compound for 2 hours prior to NMDA treatment. 0.1 μM (+)-MK-801 Hydrogen Maleate (Sigma) was added as a positive control. Briefly, the neurons were rinsed with Locke's solution (5 mM potassium chloride, 128 mM sodium chloride, 2.7 mM calcium chloride, 1 mM di-sodium hydrogen orthophosphate, 5 mM HEPES and 10 mM glucose in Milli-Q water) without $Mg^{2+}$, and incubated with addition of glycine (10 μM) for 15 minutes. After the incubation, the neurons were co-treated with the test compound (dissolved in Locke's plus glycine solution) and NMDA (20 μM; Sigma) for 20 minutes. Neurons were rinsed with Locke's plus $Mg^{2+}$ and replaced with fresh growth medium. After incubation in culture medium for 24 hours, neurons were fixed with 4% paraformaldehyde for 20 minutes at room temperature, permeabilized and blocked with 4% goat serum and 0.4% Triton X-100. Double staining was performed by incubating the neurons with mouse monoclonal antibody specific for β tubulin isotype III (1:1000; Sigma) at 4° C. overnight followed by FITC-conjugated goat anti-mouse antibody (1:1000; Invitrogen). Neurons were counter-stained with DAPI (1:5000) to visualize nuclei before mounting. Neurons were then analyzed by a fluorescence microscope using a 40× objective (DMRA; Leica). Immunofluorescent images were acquired with a RT Slider digital camera (#2.3.1, Diagnostics Instruments), collected with SPOT software (Diagnostics Instruments) and prepared for presentation with Adobe Photoshop®.

4. Middle Cerebral Artery Occlusion (MCAO) Model

Before surgery, male rats were 259-354 g fasted overnight with free access to water. Briefly, rats were anesthetized with chloral hydrate (400 mg/kg, ip). Through a midline neck incision, the right common and external carotid artery were isolated from muscles and coagulated. A suture with a blunted tip was inserted into the internal carotid through the external carotid artery stump and advanced up to 21 mm or till resistance was left. A thermostatically regulated heating pad was used to maintain temperature at 37° C. After 2 h of MCAO, the suture was removed to restore blood flow. In sham group, the same surgical procedure was performed except that the suture was introduced into the external carotid artery but not advanced. After surgery, the incision was sutured and the rats were returned to their cage with free access to water and food.

Functional Tests

Neurological function of ischemic rats was graded on modified Neurological Severity Score (mNSS) system in a range of 0 to 18 (normal score, 0; maximal deficit score, 18). The mNSS system is a composite evaluation of motor and sensory function, balance impairment and reflex abnormality of ischemic animals (Chen et al., 2001 Intravenous administration of human umbilical cord blood reduces behavioral deficits after stroke in rats. *Stroke* 32:2682-8.). In the severity scores of injury, 1 score point is awarded for the inability to perform the test or for the lack of a tested reflex; thus, the higher the score, the more severe is the injury.

Infarct Volume

At 3 days after ischemia, whole brains were rapidly removed. The brain were sliced into 2-mm-thick coronal sections and stained with 1% 2,3,5-triphenyltetrazoliumchloride (TTC, Sigma) at 37° C. for 30 minutes in the dark, followed by fixation with 4% paraformaldehyde (PFA) at 4° C. overnight. The sections were scanned with scanner connected to a computer. The unstained areas, defined as infarct tissue, were calculated by using an image analysis program. The infarct volume was calculated by measuring the unstained area in each slice. The infarct area in each slice was calculated by subtracting the normal ipsilateral (ischemic) area from that of the contralateral (non-ischemic) hemisphere to reduce errors due to cerebral edema and was presented as a percentage relative to the area of the contralateral hemisphere.

Edema Volume

The contralateral hemispheric volume was used as a control for calculation of ischemia-induced brain edema in the ipsilateral hemisphere. A net difference in hemispheric volumes was gained by subtracting the volume of the hemisphere from that of the infracted hemisphere. Brain swelling was expressed as a percentage of the net difference in ischemic hemispheric volume over the contralateral hemispheric volume.

Data Analysis

Values are expressed as mean±S.E.M. Comparisons between the groups were done by student t test.

5. Morris Water Maze 6-8 week old outbred male I.C.R. mice, weighing 25-35g were housed two per cage in a climatically controlled animal room (23-25° C.) under 12 hours light/dark cycling. The animals were allowed access to water and food ad lib. The mice used for the experiment were brought to particular laboratory conditions for two days. All the experiments were conducted between 14:00 and 18:00. Scopolamine hydrobromide (Sigma, USA) was dissolved in saline in 4 mg/kg and administered in a volume of 10 ml/kg body weight. The experimental mice were randomly assigned into 3 groups, each consisting of 12 mice with similar mean body weights and age. Test sample was dissolved in physiological saline before the experiments each day. Scopolamine was administered through intraperitoneal injection (i.p.) at 30 minutes before the swimming tasks to induce memory deficit. Oral administrations (p.o.) of the test compound, or saline (0.9%) was started at the first day of the task and administrated according to a volume of 10 ml/kg body weight. Oral drug administrations were 45 minutes before the swimming tasks and conducted daily for 4 consecutive days until the end of the task.

Each mouse was subjected to 4 trials per day for 4 consecutive days. A trial began when a mouse held facing the pool wall was immersed in the water. The mouse was then allowed 60 seconds to search for the platform. If the mouse failed to escape within this time period, it was guided and placed on the platform. Regardless of whether the mouse found the platform or not, it remained there for 20 seconds. There was a 30 seconds recovery period between trials. The 4 trials were started randomly from the 3 points (between north an west) located farthest from the platform. Because both the escape latency and swimming distance of mice in the behavioral experiment showed similar group differences, only the escape latency to find the platform in the water maze was used to evaluate the memory performance in the tested mice. The student t-test with repeated measures was used to analyze latency values, and calculated as the mean latency periods for each mouse. Data are expressed as means±S.E.M, *=P<0.05 and **=P<0.005 versus scopolamine.

6. Forced Swim Test (FST)

Outbred male I.C.R. mice of ~3-4 weeks old weighing 20-22 g were used. The mice had free access to food (rodent chow #2053, 5g/mouse/day) and water. The cage floors were covered with wood shavings and the mice were handled once per week while the cages were cleaned. Mice were randomly assigned into groups: group 1—test group; group 2—Vehicle; group 3—imipramine. Number of mice per group was ~10-15. To facilitate adaptation to novel surroundings, mice were transported to the testing area from the core animal facility at least one week prior to testing. All experimental sessions were conducted between 0900 and 1200 hours. Briefly, mice were put into a pyrex cylinder of 30 cm in height and 11.5 cm in diameter with water (10 cm) to a level that they would not be able to touch the bottom. Mice were put into the cylinder for twice, first day 15 min and second day 6 min. The duration of immobility (within the last 4 min in the 6-min time frame) of mice in FST were recorded using Etho-Vision® XT Mobility (Noldus software). The parameters to score the behavior of animals in the FST were fine-tuned by visual inspection. The threshold settings in EthoVision to distinguish between immobility, mobility and strong mobility were established. The mean score resulting from this inspection was used as threshold setting during the entire experiment. The test compound was orally administered at 24 hour (right after the 15-min swim) and 45 min before the swimming session (6-min swim). Mice were fasted for 12 hours before testing.

7. Western Blot Detection for Phosphorylation of Signaling Proteins

Embryonic day 18 Sprague Dawley rat pups were decapitated, their brains removed, and the cortices were isolated. Tissues were triturated and isolated neurons were plated onto 60 mm plate and cultured with Neurobasal medium supplemented with 2% B27 (Invitrogen). Experiments were performed after 10-12 days in vitro (DIV). Cultured cells were stimulated with a test compound or vehicle control (DMSO) for different time intervals and then lysed with RIPA buffer including protease inhibitors. Cell lysates were stored at −80° C. before use. Before being loaded, the lysates were heated to 95° C. for 10 min, vortexed and centrifuged for 7 min at 15,000×g. Supernatants were electrophoresed on 10% SDS-polyacrylamide gel and transblotted to nitrocellulose membrane. The membranes were washed with 5% (w/v) powdered milk dissolved in PBS with 0.1% Triton X-100, followed by incubation at 4° C. overnight with rabbit polyclonal against phospho-ERK or phosphor-AKT (1:1000, Cell Signaling Technology). Next, the membranes were washed and incubated with horseradish peroxidase (HRP)-conjugated secondary antibodies. The signal was visualized using ECL Western Blotting Kit. Blots were stripped and probed for total ERK or AKT expression.

Example 53

Compound LC-02 Exhibits NMDA Receptor Antagonist Activity Via Whole Cell Patch Clamp As shown in FIG. 1, whole cell patch clamp studies were conducted to measure the ion current across the surface of hippocampal neurons in the presence and absence of the novel compounds to demonstrate NMDA receptor activity. The NMDA receptor is a gated ion channel, which allows inflow of current during a nerve impulse. Antagonists to the receptor would prevent the inflow of current. As seen in FIG. 1, co-application of LC-02 resulted in a decreases in NMDA induced current in hippocampal neurons.

In FIG. 1A, hippocampal neurons from embryonic day 18 rats were isolated, trypsinized, plated onto 35-mm plates at a density of $3 \times 10^4$ cells/plate and cultured in Neurobasal medium (NB) supplemented with B27 nutrient. Rat hippocampal neurons (10-14 DIV) were treated with NMDA (50 µM) in the absence or presence of the compound LC-02 (10 µg/mL). Data is presented as % of NMDA-induced current. DMSO is the solvent control.

In FIG. 1B, NMDA antagonistic effect of LC-02 on current responses of a single hippocampal neuron. NMDA (200 uM) was applied for 2.5 sec every 30 sec but these inter-response intervals have been deleted from the above figure for a better resolution of the kinetics of individual responses (blank space in trace). LC-02 (500 uM) was co-applied with NMDA. Partial recovery of NMDA-induced current was readily observed after LC-02 was washed out.

In FIG. 1C, effects of LC-02 on pooled NMDA current responses. Normalized peak and plateau currents are shown in the absence (DMSO) and presence of LC-02. LC-02 significantly inhibits NMDA-induced current. *=P<0.05, **=P<0.001, n=6.

Example 54

Figure 2:
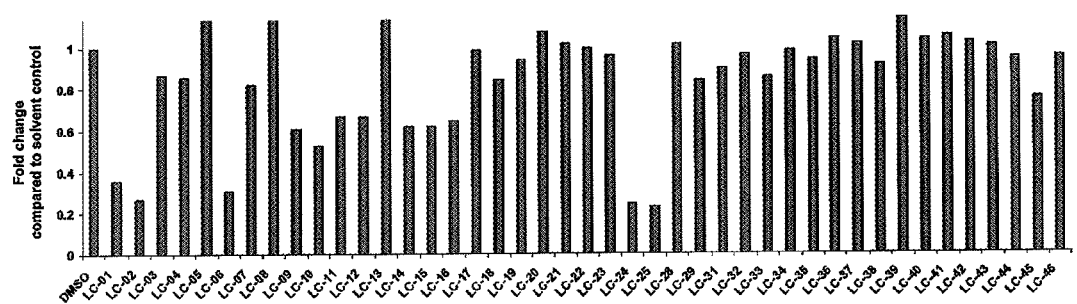
FIG. 2 illustrates the effect of NMDA insults on cortical neurons in the absence (DMSO) and presence of these novel compounds. Oxazolidine derivatives protect against NMDA excitotoxicity in rat cortical neurons.

LC Oxazolidine Derivative Compounds Protect Rat Primary Cortical Neurons Against NMDA Excitotoxicity Novel compounds (LC-01-LC-46) were subjected to NMDA survival assays to evaluate their ability to reduce NMDA receptor-mediated excitotoxicity in primary cortical neuronal cells. FIG. 2 shows the effect of NMDA insults on cortical neurons in the absence (DMSO) and presence of these novel compounds. Cell death was reduced by more than 60% in some instances, compared to the DMSO control. The LC series of compounds protect against NMDA excitotoxicity in rat cortical neurons.

Embryonic rat cortical neurons (11 DIV) were treated with NMDA (20 µM) in the absence or presence of the LC series of compounds (10-30 µg/ml). LC-01, LC-02, LC-06, LC-24 and LC-25 significantly protected rat primary cortical neurons from NMDA insults while LC-09, LC-10, LC-11, LC-12, LC-14, LC-15, LC-16 indicated weaker neuroprotective effects. LDH release in the medium after overnight incubation was measured and fold change was calculated when compared to the solvent control, DMSO.

Example 55

Figure 3:
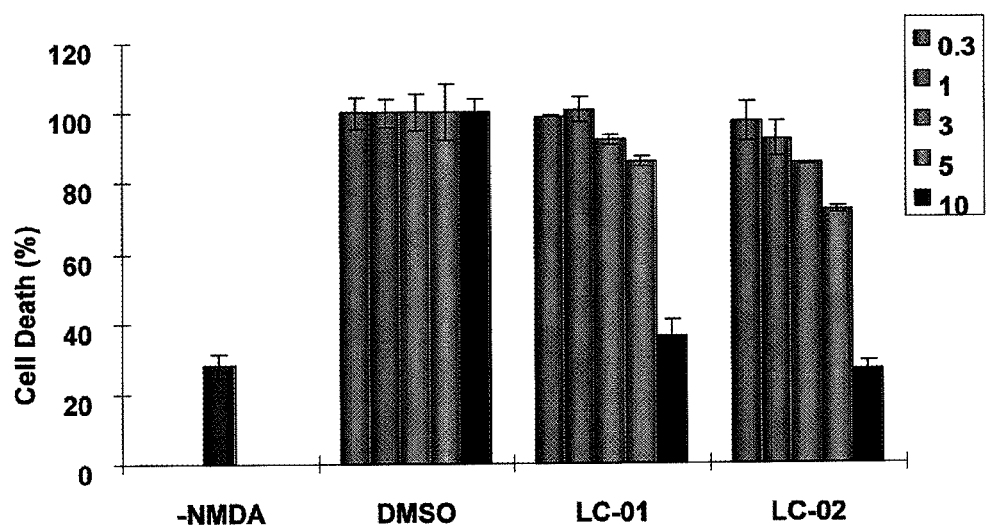
FIG. 3 shows that cell death was markedly reduced in the presence of either LC-01 or LC-02 (10 µg/mL) in comparison to the negative control (DMSO). Compounds LC-01 and LC-02 protect against NMDA excitotoxicity in rat cortical neurons at various concentrations.

Dose-Dependent Protective Effect of Compounds LC-01 and LC-02 on Rat Primary Cortical Neurons Upon NMDA Insult Dose-dependant NMDA survival assays were conducted on the compounds LC-01 and LC-02. Rat primary cortical neurons were subjected to NMDA (20 µM) in the absence and presence of varying concentrations of these compounds. FIG. 3 shows that cell death was markedly reduced in the presence of either LC-01 or LC-02 (10 µg/mL) in comparison to the negative control (DMSO). Compounds LC-01 and LC-02 protect against NMDA excitotoxicity in rat cortical neurons at various concentrations.

Embryonic rat cortical neurons (DIV 11) were treated with NMDA (20 µM) in the absence or presence of LC-01 or LC-02 (µg/mL). LDH release in the medium after overnight incubation was measured and cell cytotoxicity was calculated in percentage when compared to the solvent control, DMSO.

Example 56

Figure 4:
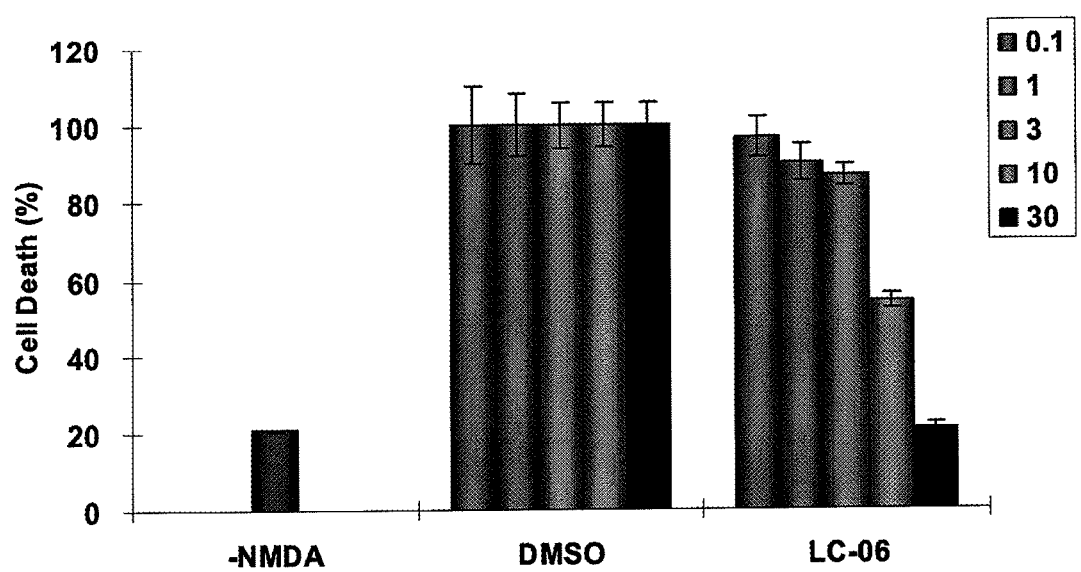
FIG. 4 shows that cell death was markedly reduced in the presence of LC-06 (10 µg/mL) in comparison to the negative control (DMSO). Compound LC-06 protects against NMDA excitotoxicity in rat cortical neurons.

Dose-Dependent Protective Effect of Compound LC-06 on Rat Primary Cortical Neurons Upon NMDA Insult Dose-dependent NMDA survival assays were conducted on the compound LC-06. Rat primary cortical neurons were subjected to NMDA (20 µM) in the absence and presence of varying concentrations of the compound. FIG. 4 shows that cell death was markedly reduced in the presence of LC-06 (10 µg/mL) in comparison to the negative control (DMSO). LC-06 protects against NMDA excitotoxicity in rat cortical neurons.

Embryonic rat cortical neurons (DIV 11) were treated with NMDA (20 µM) in the absence or presence of LC-06 (µg/mL). LDH release in the medium after overnight incubation was measured and cell cytotoxicity was calculated in percentage when compared to the solvent control, DMSO.

Example 57

Figure 5:
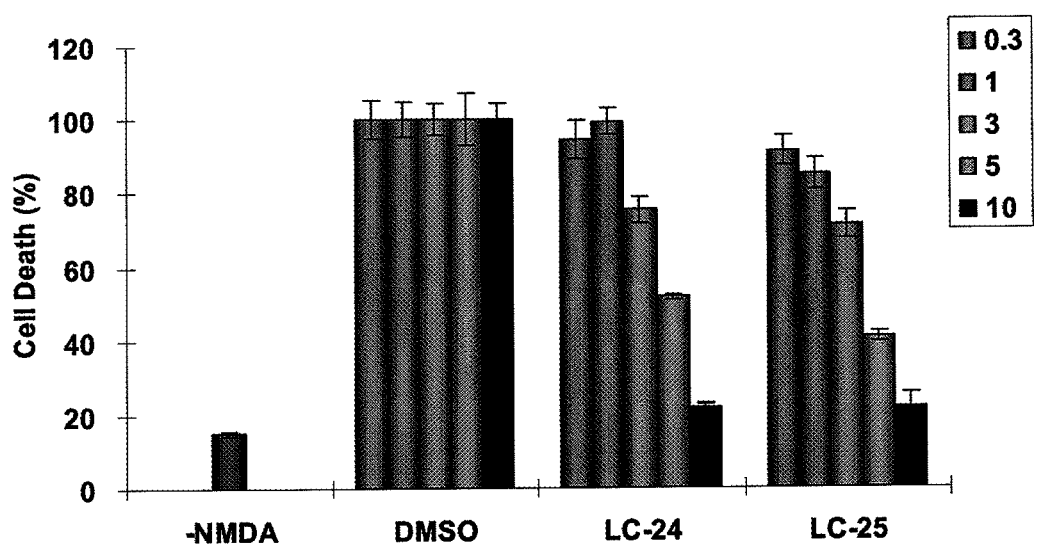
FIG. 5 shows that cell death was markedly reduced in the presence of either LC-24 or LC-25 (10 µg/mL) in comparison to the negative control (DMSO). Compounds LC-24 and LC-25 protect against NMDA excitotoxicity in rat cortical neurons.

Dose-Dependent Upon Protective Effect of Compounds LC-24 and LC-25 on Rat Primary Cortical Neurons Upon NMDA Insult Dose-dependent NMDA survival assays were conducted on the compounds LC-24 and LC-25. Rat primary cortical neurons were subjected to NMDA (20 µM) in the absence and presence of varying concentrations of these compounds. FIG. 5 shows that cell death was markedly reduced in the presence of either LC-24 or LC-25 (10 µg/mL) in comparison to the negative control (DMSO). LC-24 and LC-25 protect against NMDA excitotoxicity in rat cortical neurons.

Embryonic rat cortical neurons (11 DIV) were treated with NMDA (20 µM) in the absence or presence of LC-24 or LC-25 (µg/mL). LDH release in the medium after overnight incubation was measured and cell cytotoxicity was calculated in percentage when compared to solvent control (DMSO).

Example 58

Figure 6:
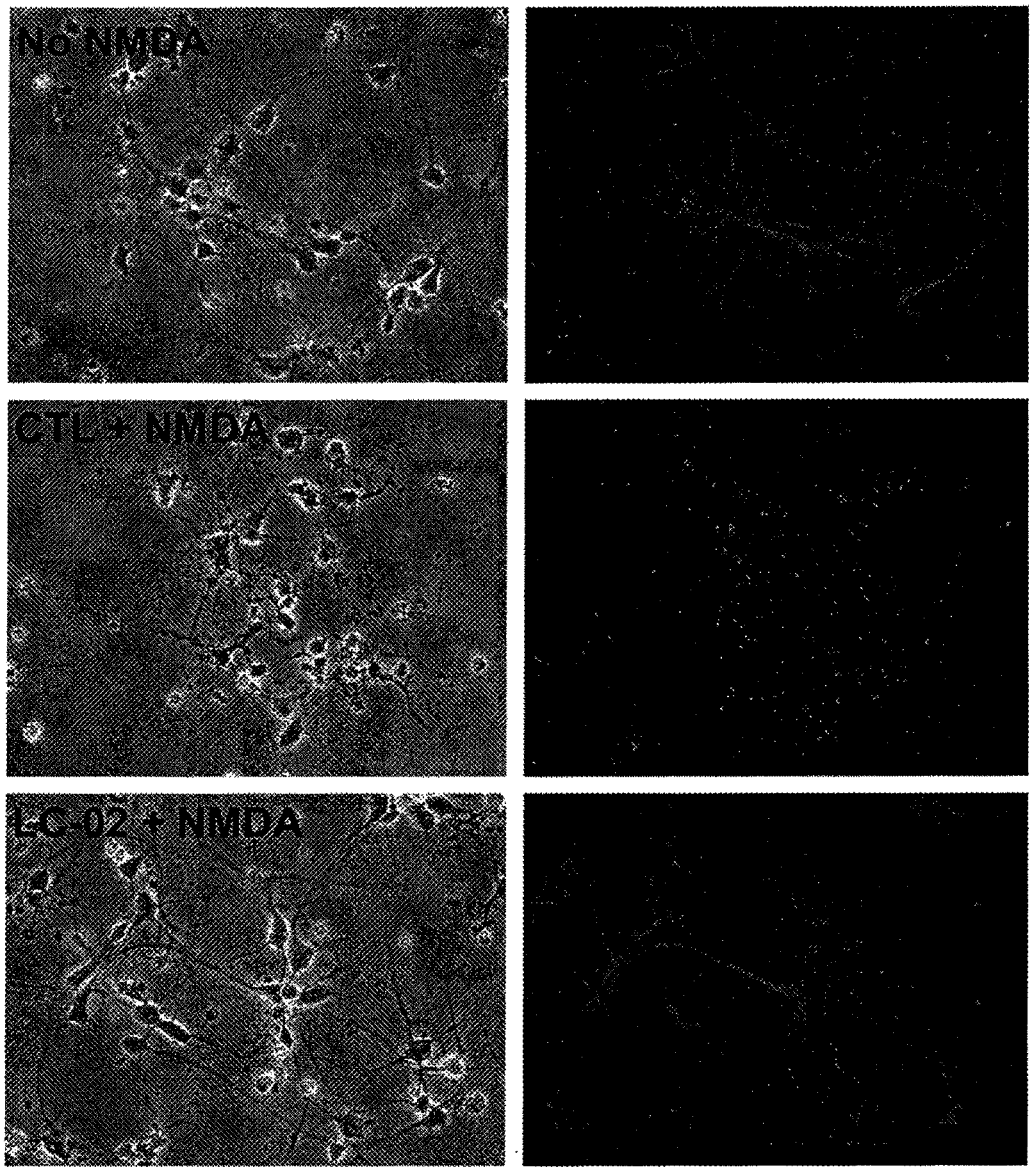
FIG. 6 illustrates that NMDA insults clearly led to cell death while the addition of compound LC-02 (10 µg/ml) protected the cells from excitotoxicity and the resulting apoptosis at a level similar to control cells (no NMDA insults). Compound LC-02 protects embryonic rat primary cortical neurons against NMDA excitotoxicity.

Compound LC-02 Prevents NMDA-Induced Excitotoxicity in Rat Primary Cortical Neurons The ability of compound LC-02 to protect against NMDA insults was visually presented through immunostaining experiments. Primary rat cortical neurons subjected to NMDA insults were observed in the absence and presence of LC-02 as seen in FIG. 6 (CTL+NMDA and LC-02+NMDA, respectively). NMDA insults clearly led to cell death while the addition of compound LC-02 (10 µg/ml) protected the cells from excitotoxicity and the resulting apoptosis at a level similar to control cells (no NMDA insults). Compound LC-02 protects embryonic rat primary cortical neurons against NMDA excitotoxicity.

LC-02 (10 µg/mL) protects embryonic rat primary cortical neurons against NMDA excitotoxicity. Neurites were immunostained with beta-tubulin type III antibody and detected with FITC-conjugated antibody. Cell bodies were highlighted with DAPI stain. DMSO was used as the solvent control (CTL).

Example 59

Figure 7:
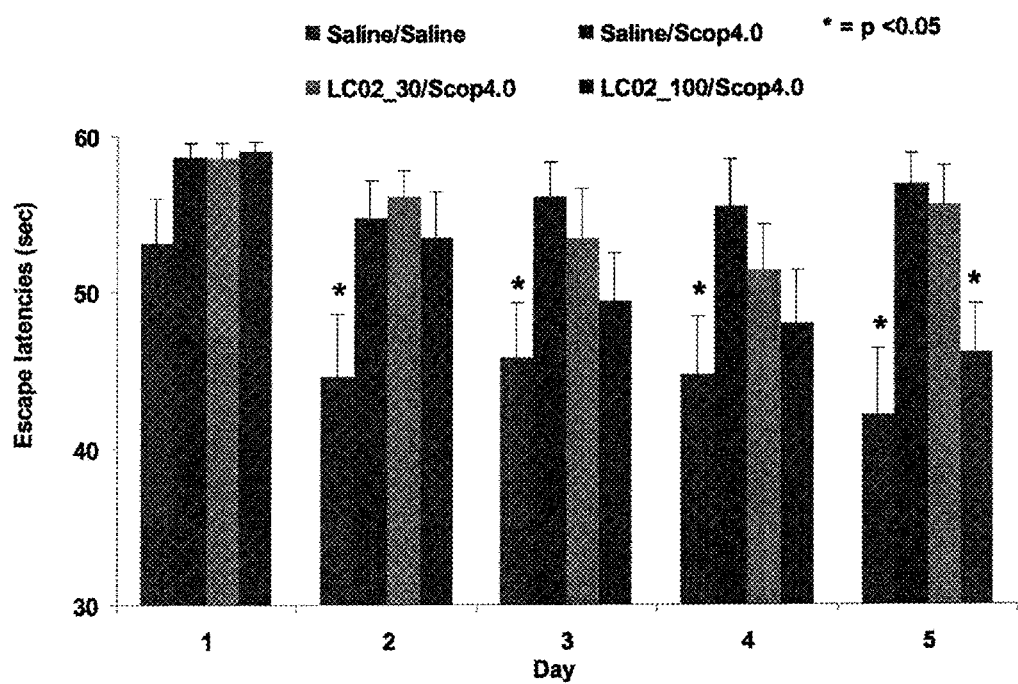
FIG. 7 shows that compound LC-02 decreases escape latencies in scopolamine-induced memory deficit mice.

Compound LC-02 Decreases Escape Latencies in Scopolamine-Induced Memory Deficit Mice Scopolamine (SCOP; 4 mg/kg) was first administered intra-peritoneally to mice to impair their memories. Scopolamine-induced memory impaired mice were then orally administered one of two different doses of LC-02 (30 or 100 mg/kg) and subjected to the Morris water maze over a period of 5 days. On each day, the time taken for the mice to detect the hidden platform in the water maze was measured, in seconds. Measurements were calculated as the mean latency periods for each mouse; n=24. Data are expressed as mean±s.e.m. and compared to Saline/SCOP group. Doses are represented in mg/kg. As shown in FIG. 7, LC-02 decreases escape latencies in scopolamine-induced memory deficit mice.

Example 60

Figure 8:
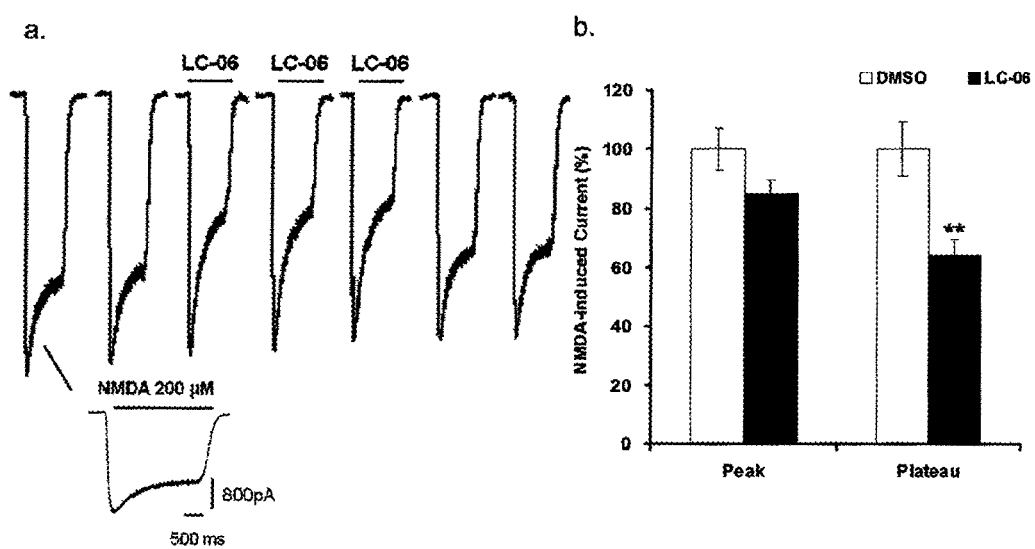
FIG. 8 illustrates that compound LC-06 decreases NMDA induced current in hippocampal neurons. (a) NMDA antagonistic effect of LC-06 on current responses of a single hippocampal neuron. (b) Effects of LC-06 on pooled NMDA current responses.

Compound LC-06 Exhibits NMDA Receptor Antagonist Activity Via Whole Cell Patch Clamp The NMDA receptor is a gated ion channel, which allows inflow of current during a nerve impulse. Whole cell patch clamp studies were conducted to measure the ion current across the surface of hippocampal neurons in the presence and absence of LC-06 to demonstrate NMDA receptor antagonist activity since antagonists to the receptor would prevent the inflow of current. As seen in FIG. 8, co-application of LC-06 with NMDA resulted in a decrease in NMDA-induced current.

In FIG. 8, (a) NMDA antagonistic effect of LC-06 on current responses of a single hippocampal neuron. NMDA (200 uM) was applied for 2.5 sec every 30 sec but these inter-response intervals have been deleted from the above figure for a better resolution of the kinetics of individual responses (blank space in trace). LC-06 (500 uM) was co-applied with NMDA. Partial recovery of NMDA-induced current was readily observed after LC-06 was washed out. (b) Effects of LC-06 on pooled NMDA current responses. Normalized peak and plateau currents are shown in the absence (DMSO) and presence of LC-06. LC-06 significantly inhibits NMDA-induced current. **=P<0.001, n=6.

Example 61

Figure 9:
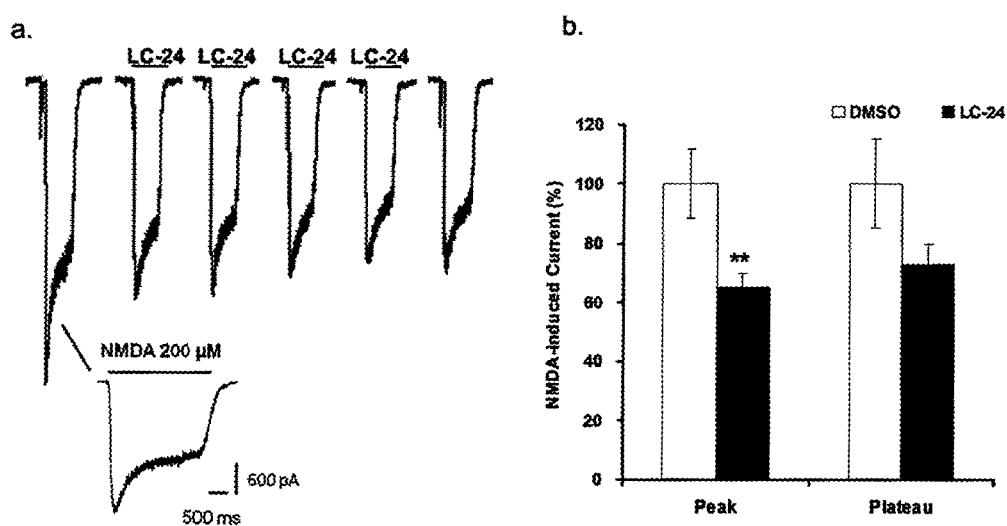
FIG. 9 illustrates that compound LC-24 decreases NMDA induced current in hippocampal neurons. (a) NMDA antagonistic effect of LC-24 on current responses of a single hippocampal neuron. (b) Effects of LC-24 on pooled NMDA current responses.

Compound LC-24 Exhibits NMDA Receptor Antagonist Activity Via Whole Cell Patch Clamp The NMDA receptor is a gated ion channel, which allows inflow of current during a nerve impulse. Whole cell patch clamp studies were conducted to measure the ion current across the surface of hippocampal neurons in the presence and absence of LC-24 to demonstrate NMDA receptor antagonist activity since antagonists to the receptor would prevent the inflow of current. As seen in FIG. 9, co-application of LC-24 with NMDA resulted in a decrease in NMDA-induced current.

In FIG. 9, (a) NMDA antagonistic effect of LC-24 on current responses of a single hippocampal neuron. NMDA (200 uM) was applied for 2.5 sec every 30 sec but these inter-response intervals have been deleted from the above figure for a better resolution of the kinetics of individual responses (blank space in trace). LC-24 (500 uM) was co-applied with NMDA. Partial recovery of NMDA-induced current was readily observed after LC-24 was washed out. (b) Effects of LC-24 on pooled NMDA current responses. Normalized peak and plateau currents are shown in the absence (DMSO) and presence of LC-24. LC-24 significantly inhibits NMDA-induced current. **=P<0.001, n=6.

Example 62

Figure 10:
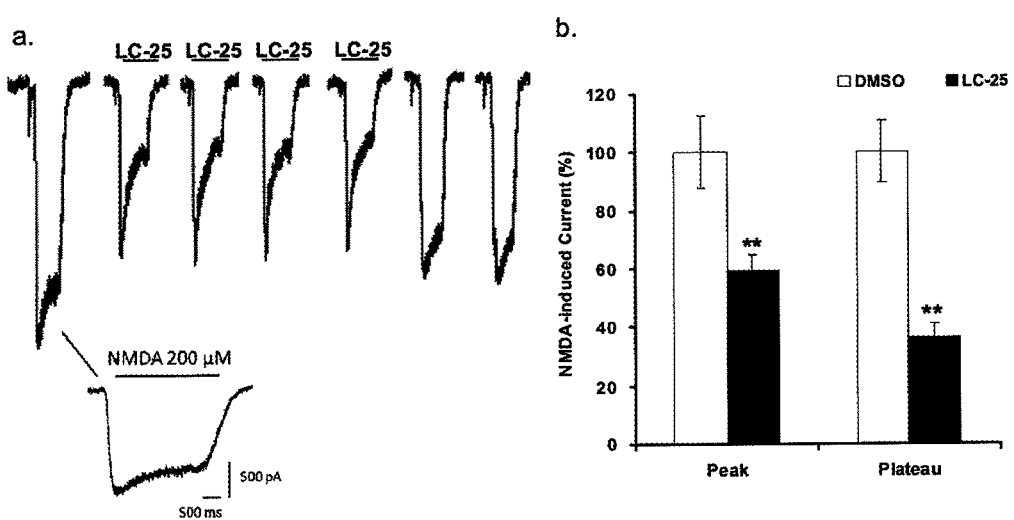
FIG. 10 illustrates that compound LC-25 decreases NMDA induced current in hippocampal neurons. (a) NMDA antagonistic effect of LC-25 on current responses of a single hippocampal neuron. (b) Effects of LC-25 on pooled NMDA current responses.

Compound LC-25 Exhibits NMDA Receptor Antagonist Activity Via Whole Cell Patch Clamp The NMDA receptor is a gated ion channel, which allows inflow of current during a nerve impulse. Whole cell patch clamp studies were conducted to measure the ion current across the surface of hippocampal neurons in the presence and absence of LC-25 to demonstrate NMDA receptor antagonist activity since antagonists to the receptor would prevent the inflow of current. As seen in FIG. 10, co-application of LC-25 with NMDA resulted in a decrease in NMDA-induced current.

In FIG. 10, (a) NMDA antagonistic effect of LC-25 on current responses of a single hippocampal neuron. NMDA (200 uM) was applied for 2.5 sec every 30 sec but these inter-response intervals have been deleted from the above figure for a better resolution of the kinetics of individual responses (blank space in trace). LC-25 (500 uM) was co-applied with NMDA. Partial recovery of NMDA-induced current was readily observed after LC-25 was washed out. (b) Effects of LC-25 on pooled NMDA current responses. Normalized peak and plateau currents are shown in the absence (DMSO) and presence of LC-25. LC-25 significantly inhibits NMDA-induced current. **=P<0.001, n=6.

Example 63

Compound LC-02 Improves Neurological Scores in Rats Subjected to MCAO

Rats were subjected to middle cerebral artery occlusion (MCAO) to induce focal cerebral ischemia. Neurological functions of these ischemic rats were then graded on a modified Neurological Severity Score (mNSS) system from a range of 0 to 18 (normal score, 0; maximal deficit score, 18).

Figure 11:
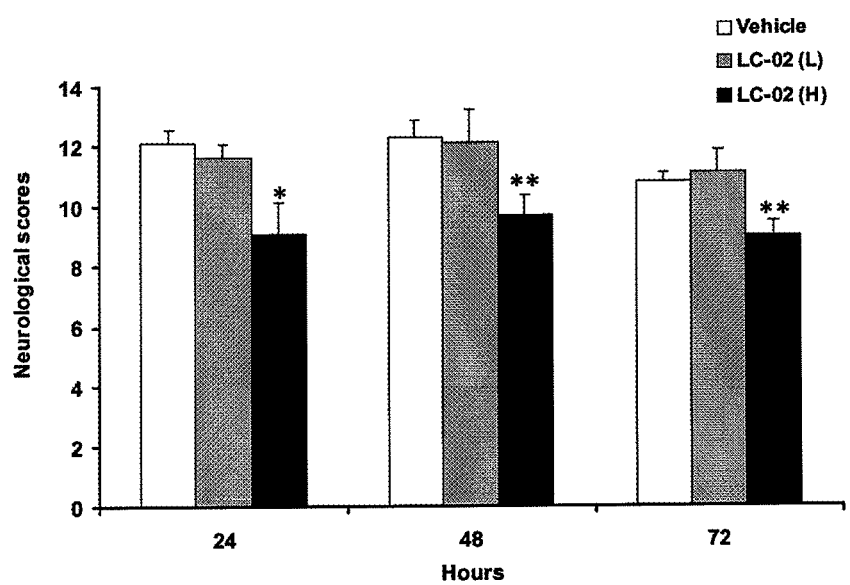
FIG. 11 shows LC-02 improves behavioral test scores in MCAO rats. Behavioral functional tests were performed in rats after MCAO. Group I: Vehicle (1.5% DMSO/saline) n=10, open bars; Group II: LC-02 (L, 35 mg/kg) n=8, grey bars; Group III: LC-02 (H, 70 mg/kg) n=9, solid bars. *P<0.05 and **P<0.01 vs control.

The mNSS system is a composite evaluation of motor and sensory function, balance impairment and reflex abnormality of ischemic animals. In the severity scores of injury, 1 score point is awarded for the inability to perform the test or for the lack of a tested reflex; thus, the higher the score, the more severe the injury. As shown in FIG. 11, oral treatment of LC-02 (70 mg/kg, H) at 24, 48 and 72 hours after MCAO significantly improved functional recovery, as evidenced by mNSS scores compared with vehicle-treated control.

Behavioral functional tests were performed in rats after MCAO. Group I: Vehicle (1.5% DMSO/saline) n=10, open bars; Group II: LC-02 (L, 35 mg/kg) n=8, grey bars; Group III: LC-02 (H, 70 mg/kg) n=9, solid bars. *P<0.05 and **P<0.01 vs control.

Example 64

LC-02 Decreased Cerebral Infarction and Edema in MCAO-Induced Cerebral Ischemia 3 days after ischemia, whole brains were rapidly removed, sliced into 2-mm-thick coronal sections, stained with 1% 2,3,5-triphenyltetrazoliumchloride (TTC) and fixed (FIG. 6a). The sections were then scanned for infarct tissue using an image analysis program. Infarct volume was measured in the coronal brain sections. Two hours of MCAO 24 hours of reperfusion showed an infarct volume of 38.70%±1.73%. However, the infarct volume was decreased to 34.45%±3.38%, and 18.49%±2.34% (P<0.01) in 35 and 70 mg/kg LC02-treated rats, respectively (FIGS. 12a and 12b**).

Infarct volume and edema volume were also measured. (FIGS. 6d and 6e) Two hours of MCAO and 24 hours of reperfusion resulted in 3.80±0.76% increase in the ipsilateral volume due to edema (FIG. 12d). However, LCO2 at the dose of 35 and 70 mg/kg reduced edema volume to 2.44±0.43%, and 2.85±0.80% of the ipsilateral hemisphere, respectively.

Figure 12:
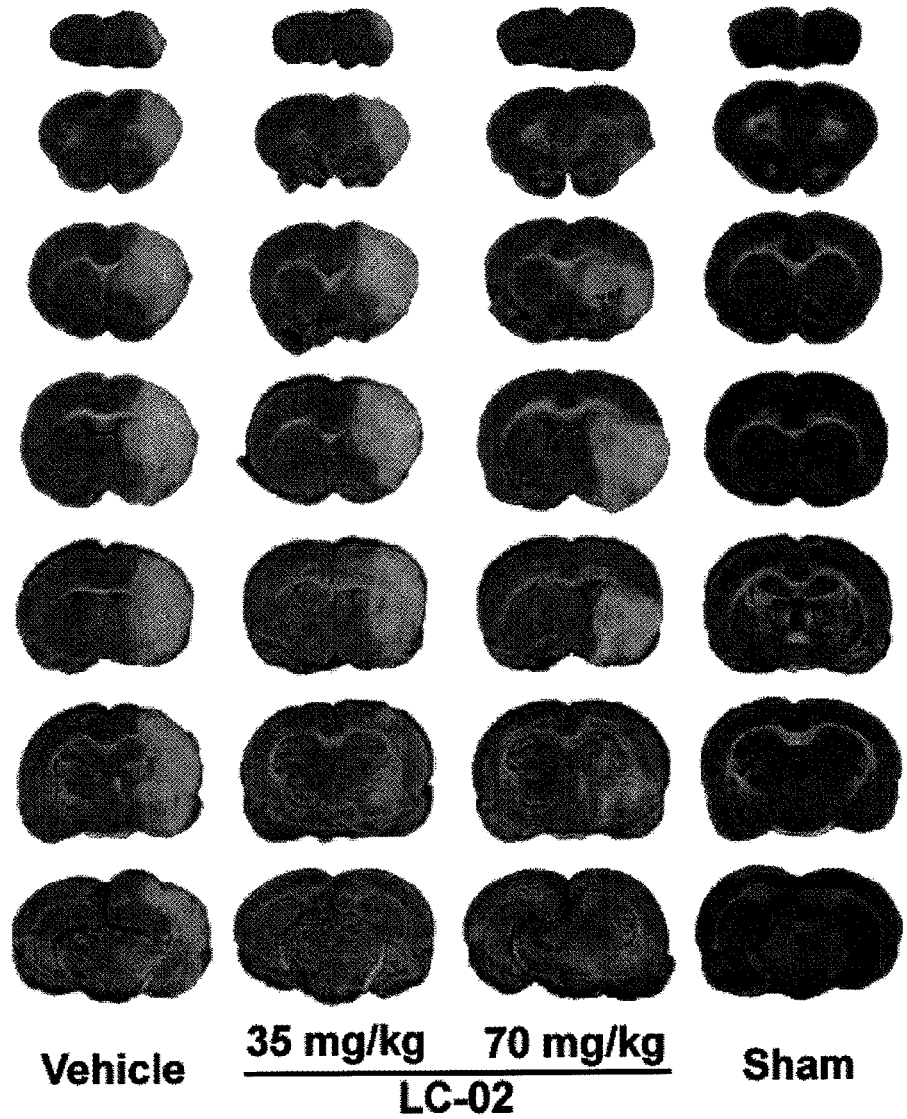
FIG. 12: (a) Illustrative coronal sections (2-mm thick) of ischemic or sham rats. The infarct area in the ischemic cerebral hemisphere were represented as distinct pale-stained area in rats with 2 hours MCAO treated with 1.5% DMSO/saline (vehicle) or LC-02 of 35 and 70 mg/kg at 6, 24 and 48 hours following the onset of ischemia. (b) Infarct area of ischemic rats was measured in 2-mm-thick coronal brain sections treated with 1.5% DMSO/saline or LC-02 (35 mg/kg (L) and 70 mg/kg (H)) at 6, 24 and 48 hours following the onset of ischemia. P<0.01 as compared to the vehicle-treated group. (c) Total infarct volume in rat brain tissues after 2 hours of MCAO treated with vehicle or LC-02 (35 and 70 mg/kg) at 6, 24 and 48 hours following the onset of ischemia. P<0.01 as compared to the vehicle-treated group. (d) Volume of edema in rat brain tissues after 2 hours of MCAO treated with vehicle or LC-02 (35 and 70 mg/kg) at 6, 24 and 48 hours following the onset of ischemia, **P<0.01 as compared to the vehicle-treated group. Data are expressed as the mean±S.E.M. of rats in each group.
Figure 12:
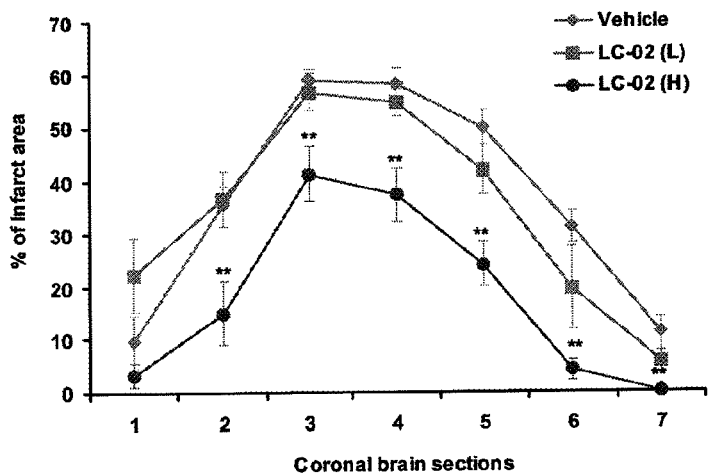
Figure 12:
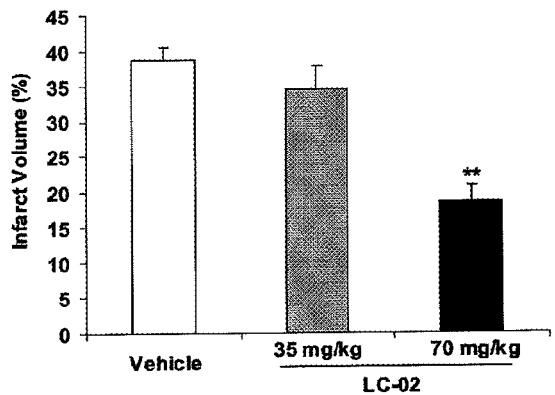
Figure 12:
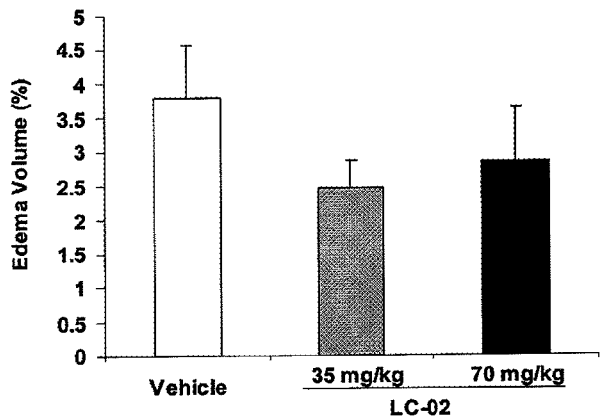

In FIG. 12, (a) Illustrative coronal sections (2-mm thick) of ischemic or sham rats. The infarct area in the ischemic cerebral hemisphere were represented as distinct pale-stained area in rats with 2 hours MCAO treated with 1.5% DMSO/saline (vehicle) or LC-02 of 35 and 70 mg/kg at 6, 24 and 48 hours following the onset of ischemia. (b) Infarct area of ischemic rats was measured in 2-mm-think coronal brain sections treated with 1.5% DMSO/saline or LC-02 (35 mg/kg (L) and 70 mg/kg (H)) at 6, 24 and 48 hours following the onset of ischemia. P<0.01 as compared to the vehicle-treated group. (c) Total infarct volume in rat brain tissues after 2 hours of MCAO treated with vehicle or LC-02 (35 and 70 mg/kg) at 6, 24 and 48 hours following the onset of ischemia. P<0.01 as compared to the vehicle-treated group. (d) Volume of edema in rat brain tissues after 2 hours of MCAO treated with vehicle or LC-02 (35 and 70 mg/kg) at 6, 24 and 48 hours following the onset of ischemia, **P<0.01 as compared to the vehicle-treated group. Data are expressed as the mean±S.E.M. of rats in each group.

Example 65

Figure 13:
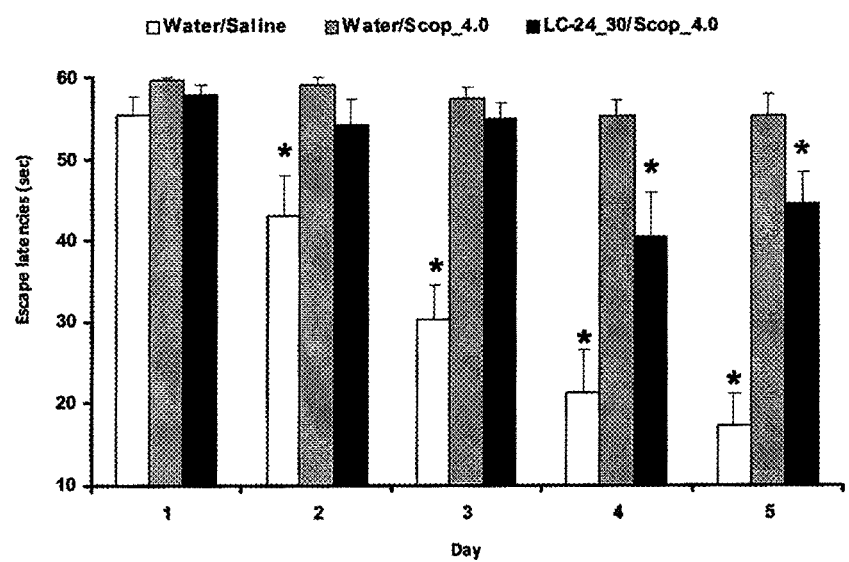
FIG. 13 illustrates that compound LC-24 reverses scopolamine-induced performance deficits in Morris Water Maze test Mice were first orally administered LC-24 (30 mg/kg), scopolamine (4 mg/kg) was i.p. administered to mice 15 min to impair their memories. Treated mice were subjected to the Morris Water Maze 30 min after scopolamine injection and the procedures were repeated over a period of 4 days. On each day, the time taken for the mice to detect the hidden platform in the water maze was measured, in seconds.

LC-24 Shortens the Escape Latencies of Memory-Deficit Mice in Morris Water Maze Test As shown in FIG. 13, the therapeutic effect of LC-24 on spatial learning and memory in mice was demonstrated using the Morris Water Maze task, the favoured test to study hippocampal-dependant learning and memory. The Morris Water Maze consists of a water pool with a hidden, submerged escape platform. The rats must learn, over a period of consecutive days, the location of the platform using either contextual or local cues. The time taken to locate the hidden platform (escape latency) is a measure of the animal's cognitive abilities.

For the compound designated LC-24, the test subjects in the control group (saline) took ~20 seconds to detect the platform after 4 days of training. In contrast, the scopolamine-induced memory-impaired group required more than three times the amount of time to locate the platform after an identical training period. LC-24 reduced the increased escape latency induced by scopolamine at a concentration of 30 mg/kg.

In FIG. 13, mice were first orally administered LC-24 (30 mg/kg), scopolamine (4 mg/kg) was i.p. administered to mice 15 min to impair their memories. Treated mice were subjected to the Morris Water Maze 30 min after scopolamine injection and the procedures were repeated over a period of 4 days. On each day, the time taken for the mice to detect the hidden platform in the water maze was measured, in seconds.

Example 66

Figure 14:
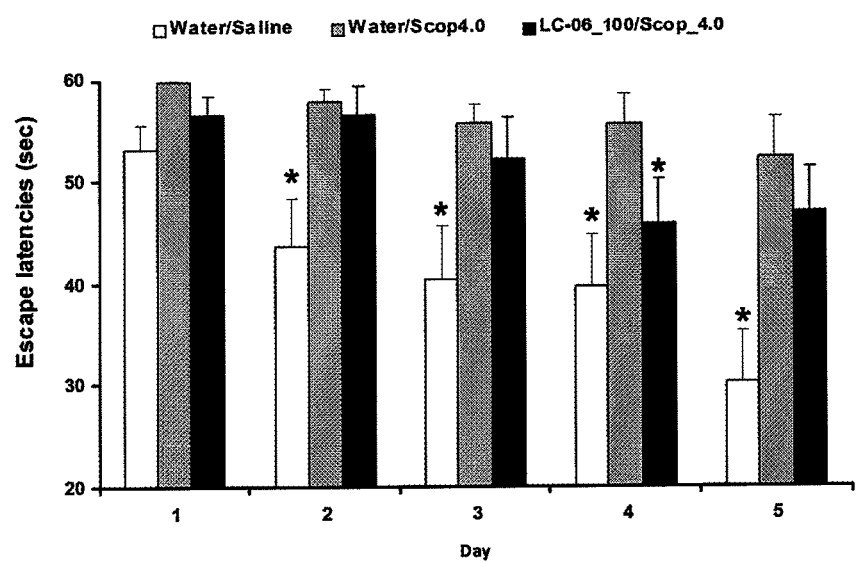
FIG. 14 illustrates that compound LC-06 reverses scopolamine-induced performance deficits in Morris Water Maze test. Mice were first orally administered LC-06 (100 mg/kg), scopolamine (4 mg/kg) was i.p. administered to mice 15 min to impair their memories. Treated mice were subjected to the Morris Water Maze 30 min after scopolamine injection and the procedures were repeated over a period of 4 days. On each day, the time taken for the mice to detect the hidden platform in the water maze was measured, in seconds.

LC-06 Shortens the Escape Latencies of Memory-Deficit Mice in Morris Water Maze Test The therapeutic effect of LC-06 on spatial learning and memory in mice was demonstrated using the Morris Water Maze task. The memory of test subjects were first impaired using scopolamine (4 mg/kg). Scopolamine-administered mice were then administered LC-06 (100 mg/kg), and the time taken to locate the hidden platform (escape latency) was measured. As seen in FIG. 14, test subjects in the control group (saline) took ~40 seconds to detect the platform after 4 days of training, while the scopolamine-induced memory-impaired group required almost twice the amount of time to locate the platform after an identical training period. LC-06 reversed the increased escape latency induced by scopolamine at a concentration of 100 mg/kg.

As shown in FIG. 14, mice were first orally administered LC-06 (100 mg/kg), scopolamine (4 mg/kg) was i.p. administered to mice 15 min to impair their memories. Treated mice were subjected to the Morris Water Maze 30 min after scopolamine injection and the procedures were repeated over a period of 4 days. On each day, the time taken for the mice to detect the hidden platform in the water maze was measured, in seconds.

Example 67

LC-02 Significantly Reduces Immobility Time of Mice in the Forced Swim Test

The Forced Swim Test (FST) is a popular animal model for assessing depression. Animals are subjected to two trials during which they are forced to swim in an acrylic glass cylinder filled with water from which they cannot escape. The time that the test animal spends in an immobile state in the second trial is measured (immobility time). This immobility time is decreased by antidepressants.

LC-02 (100 mg/kg, p.o.) or a known anti-depressant, imipramine, (15 mg/kg, i.p.) or water control was administered 7 times, once per day for 6 days and 45 min before the task. The task was then performed twice and the duration of time the mice spent in an immobile state during the second trial was measured. As indicated in FIG. 15, a significant reduction in mobility was observed for mice treated with LC-02, similar to that observed with the anti-depressant imipramine.

Figure 15:
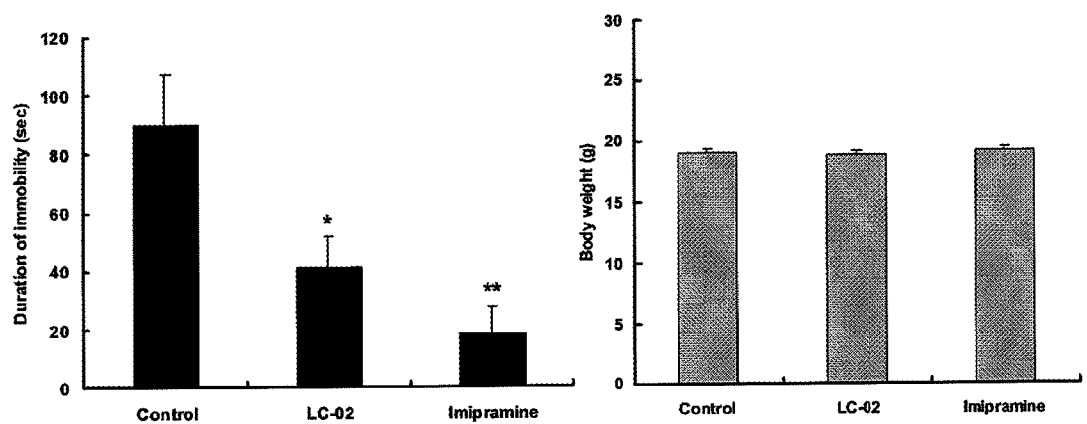
FIG. 15 illustrates that compound LC-02 significantly reduces the duration of immobility time of mice in the Forced Swim Test. The immobility time was recorded by Etho-Vision XT (Noldus) during a 6-min forced swim test, and data within the last 4 min were compared. Mice were judged to be immobile when they ceased to struggle. Data is presented as average of SEM from 3 independent experiments, n=15. *=P<0.05, **=P<0.005. Similar weight of mice was used in the test.

As shown in FIG. 15, the immobility time was recorded by Etho-Vision XT (Noldus) during a 6-min forced swim test, and data within the last 4 min were compared. Mice were judged to be immobile when they ceased to struggle. Data is presented as average of SEM from 3 independent experiments, n=15. *=P<0.05, **=P<0.005. Similar weight of mice was used in the test.

Example 68

Figure 16:
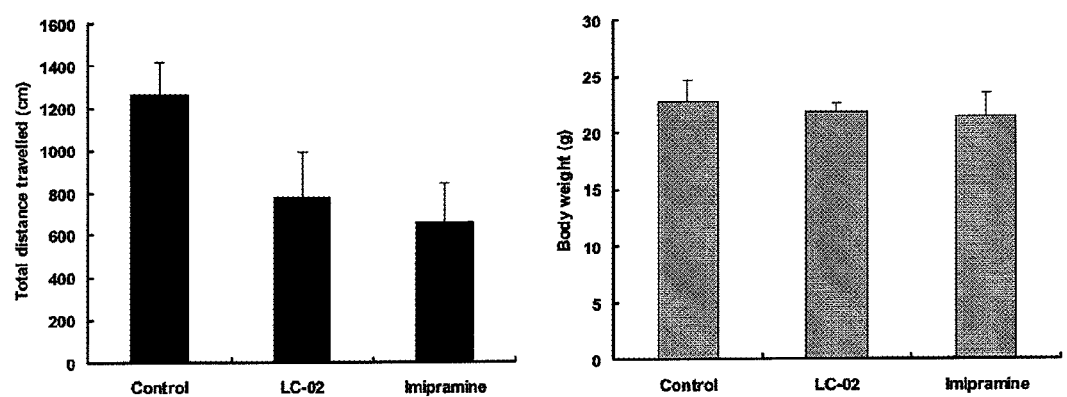
FIG. 16 shows that compound LC-02-treated mice do not result in increased excitable behavior.

LC-02 Does not Result in Increased Excitable Behaviour Response in the Open Field Test As shown in FIG. 16, compound LC-02 significantly reduced the immobility time in the Forced Swim Test (FST), indicative of a potential anti-depressant effect. Therefore, an Open Field Test (OFT) was performed to confirm that the anti-depressant effect observed in the FST by LC-02-treated mice was not a result of excitability. The Open Field Test (OFT) is designed to measure behavioral responses such as locomotor activity, hyperactivity, exploratory behaviors, as well as anxiety. Rats and mice tend to avoid brightly illuminated, novel, and open spaces. Thus, the open field environment acts as an anxiogenic stimulus and allows for measurement of anxiety-induced locomotor activity and exploratory behaviors. The OFT is a one trial test with little or no impact on the animal's subsequent behavior.

A similar treatment paradigm as that in the FST was performed on the mice prior to the OFT. LC-02 (100 mg/kg, p.o.) or imipramine, (15 mg/kg, i.p.) or water control was administered 7 times, once per day for 6 days and 45 min before the task. As shown in FIG. 16, the total distance travelled did not significantly differ in the LC-02-treated mice compared to the control group. Therefore, the anti-depressant effect observed in the FST was not associated with increased excitability.

As shown in FIG. 16, mice were transferred to the experimental room 40 min prior to initiating the test to acclimate and habituate the mice to the field. The total distance traveled during the last five minutes in the open field was recorded by a videocamera (mounted over the open field 2 meters above the floor) and scored by the Noldus EthoVision XT software package. LC-02 (100 mg/kg, p.o.), imipramine (15 mg/kg, i.p.) or water control was administered 7 times, once per day for 6 days and 45 min before the task. Data is presented as average of SEM from 3 independent experiments, n=15. *=P<0.05, **=P<0.005. Similar weight of mice was used in the test.

Example 69

LC-06 Reduces the Duration of Immobility of Mice in the Forced Swim Test

LC-06 (100 mg/kg, p.o.), a known anti-depressant, imipramine, (15 mg/kg, i.p.) or water control was administered 7 times, once per day for 6 days and 45 min before the task. The task was then performed twice and the duration of time the mice spent in an immobile state during the second trial was measured. As indicated in FIG. 17, a significant reduction in mobility was observed for mice treated with LC-02, similar to that observed with the anti-depressant imipramine.

Figure 17:
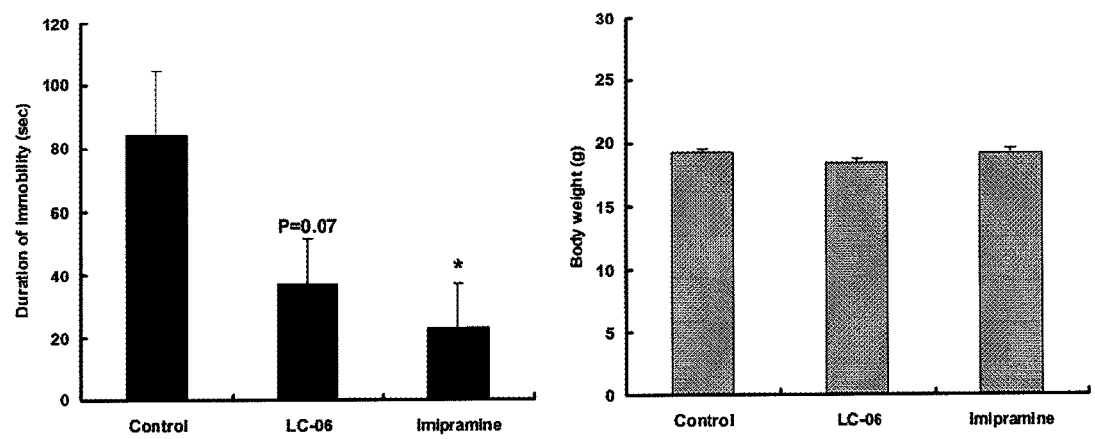
FIG. 17 illustrates that compound LC-06 reduces the duration of immobility of mice in the Forced Swim Test.

As shown in FIG. 17, the immobility time was recorded by Etho-Vision XT (Noldus) during a 6-min forced swim test, and data within the last 4 min were compared. Mice were judged to be immobile when they ceased to struggle. Data is presented as average of SEM from 3 independent experiments, n=15. *=P<0.05, **=P<0.005. Similar weight of mice was used in the test.

Example 70

LC-24 and LC-25 Significantly Reduce the Duration of Immobility of Mice in the Forced Swim Test LC-24 (100 mg/kg, p.o.), LC-25 (100 mg/kg, p.o.), imipramine (15 mg/kg, i.p.) or water control was administered 7 times, once per day for 6 days and 45 min before the task. The task was then performed twice and the duration of time the mice spent in an immobile state during the second trial was measured. As indicated in FIG. 18, a significant reduction in mobility was observed for mice treated with LC-24 and LC-25, similar to that observed with the anti-depressant imipramine.

Figure 18:
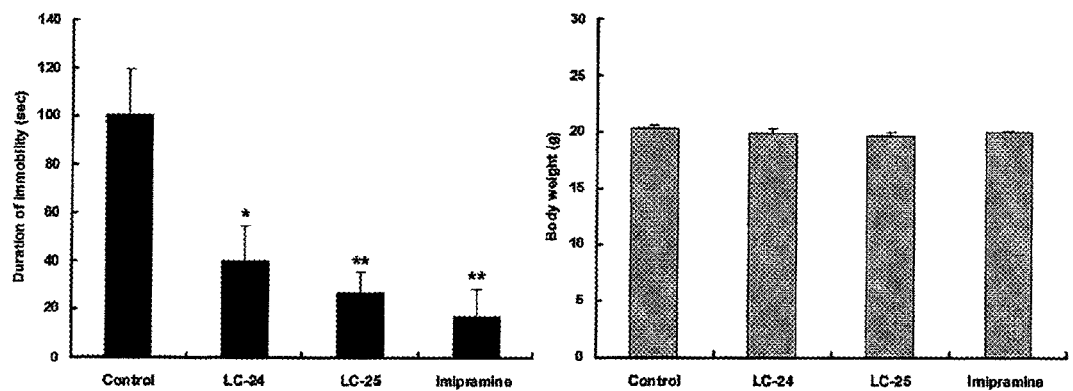
FIG. 18 illustrates that compounds LC-24 and LC-25 significantly reduce the duration of immobility of mice in the Forced Swim Test. The immobility time was recorded by Etho-Vision XT (Noldus) during a 6-min forced swim test, and data within the last 4 min were compared. Mice were judged to be immobile when they ceased to struggle. Data is presented as average of SEM from 3 independent experiments, n=15. *=P<0.05, **=P<0.005. Similar weight of mice was used in the test.

As shown in FIG. 18, the immobility time was recorded by Etho-Vision XT (Noldus) during a 6-min forced swim test, and data within the last 4 min were compared. Mice were judged to be immobile when they ceased to struggle. Data is presented as average of SEM from 3 independent experiments, n=15. *=P<0.05, **=P<0.005. Similar weight of mice was used in the test.

Example 71

LC-02 Induces the Phosphorylation of ERK and AKT Protein in Rat Cortical Neurons To study the biological effect of LC-02 in cortical neurons, a western blot analysis was performed using various antibodies against cellular phospho-proteins. LC-02 induced phosphorylation of ERK after a 15-min treatment period and persisted to 60 min when compared to D5 (DMSO control). AKT protein was phosphorylated within 5-15 min after initiation of the treatment.

Figure 19:
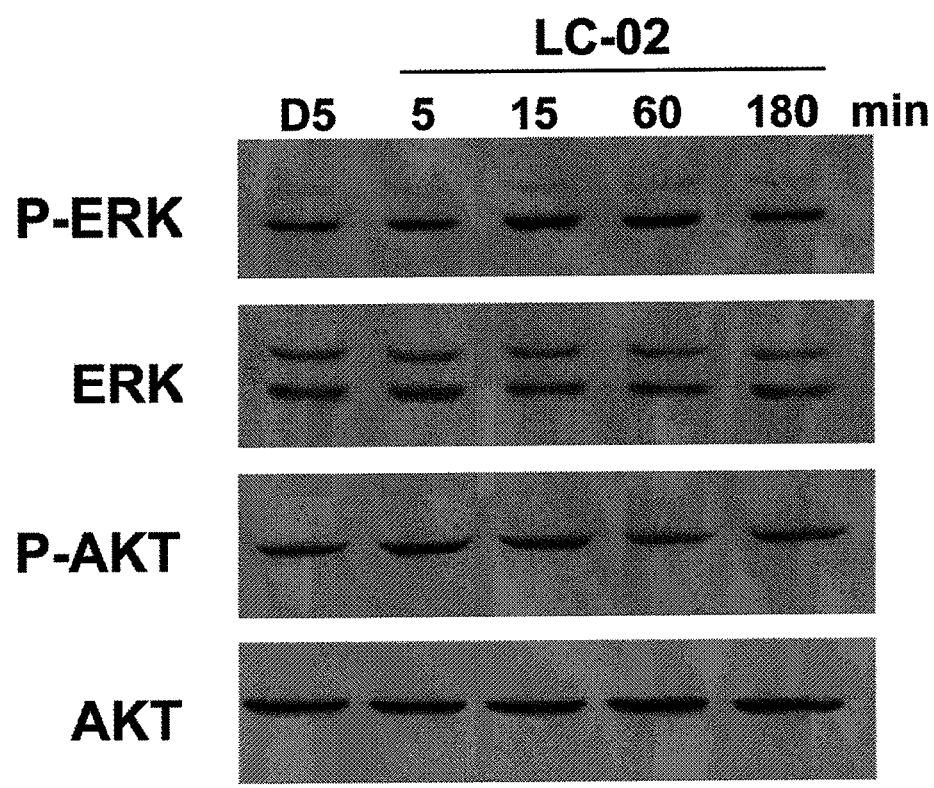
FIG. 19 illustrates that compound LC-02 induces the phosphorylation of ERK and AKT protein in rat cortical neurons.

As shown in FIG. 19, rat cortical neurons of 11 DIV were treated with LC-02 (500 µM) for various time intervals. Western blot analysis was performed on the total cell lysates. Antibodies against phospho-ERK1/2 and phospho-AKT were used and detected with HRP conjugated secondary antibodies. Protein bands were visualized using ECL Western blot detection kit. 30 µg of proteins were loaded and equal loading of proteins were compared by probing with antibodies against total protein of ERK and AKT.

Example 72

LC-02 Inhibits the Ligand Binding of Adenosine and Opioid Receptors

To determine the pharmacological profile and potential targets of LC-02, 80 binding assays were performed (High-throughput Profile, CEREP, France). LC-02 was evaluated at a single concentration in these specific binding assays. As shown in Table 4, LC-02 showed a moderate inhibitory effect on ligand binding to the adenosine A3 receptor and the opioid kappa receptor. A cutoff of 25% is considered as a moderate effect. LC-02 showed a 30% inhibition on $[^{125}I]$AB-MECA binding to the A3 receptor and $[^{3}H]$U 69593 to the kappa receptor.

TABLE 4

| LC-02 inhibition of ligand binding of adenosine and opioid receptors | |
|---|---|
| Targets | % of inhibition of ligand binding |
| Adenosine A1 | 5 |
| Adenosine A2$_A$ | 6 |
| Adenosine A3 | 30 |
| Opioid (delta) | 18 |
| Opioid (kappa) | 26 |
| Opioid (mu) | 14 |

Compound LC-02 (10 μM) was subjected to ligand binding assays with human A3 and rat kappa receptor overexpressing cells. Results are expressed as a percent of control specific agonist response [100-(measured specific response/control specific agonist response)×100] obtained in the presence of LC-02.

Although the foregoing invention has been described in some detail by way of illustration and example for purposes of clarity of understanding, one with skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound of formula (I):

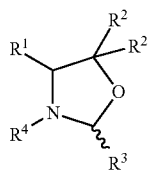

I or pharmaceutically acceptable salts and solvates thereof; wherein:
$R^1$ is selected from the group consisting of $(C_1-C_8)$alkyl, $(C_1-C_8)$heteroalkyl, $(C_3-C_8)$cycloalkyl, $(C_3-C_8)$cycloalkyl-alkyl, heterocycloalkyl, heterocycloalkyl-$(C_1-C_6)$alkyl, heterocyclyl-alkyl, aryl, phenyl-$(C_1-C_6)$alkyl, imidazolyl-$C_1$-$C_6$alkyl, pyrazolyl-$(C_1-C_6)$alkyl, oxazolyl-$(C_1-C_6)$alkyl, isoxazolyl-$(C_1-C_6)$alkyl, thiazolyl-$(C_1-C_6)$alkyl, isothiazolyl-$(C_1-C_6)$alkyl, furanyl-$(C_1-C_6)$alkyl, and thiophenyl-$(C_1-C_6)$alkyl;
$R^2$ is $(C_1-C_8)$alkyl;
$R^3$ is selected from the group consisting of —H, $(C_1-C_8)$alkyl, $(C_1-C_8)$heteroalkyl, heteroaryl-alkyl and aryl;
$R^4$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, $X^1S(O)R^a$, $X^1S(O)_2R^a$, $X^1SO_2NH_2$, $X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group; wherein $R^a$ is $(C_1-C_8)$alkyl or aryl and each $X^1$ is independently a bond or an $(C_1-C_4)$alkylene;
the wavy line denoted by ⌇ indicates the carbon to which the wavy line is attached has a stereoconfiguration of R, S or a mixture thereof;
optionally, $R^1$ and $R^4$ together with the atoms to which they are attached form a 5-membered heterocyclic ring containing 0-1 additional ring heteroatom selected from O or N; and
wherein each of $R^1$-$R^4$ groups is optionally substituted with from 1-3 $R^b$ substituents independently selected from the group consisting of halogen, —OH, —$OR^c$, —$OSi(R^c)_3$, —OC(O)O—$R^c$, —OC(O)Rc, —OC(O)NHRc, —OC(O)N($R^c$)$_2$, —SH, —$SR^c$, —S(O)$R^c$, —S(O)$_2R^c$, —SO$_2$NH$_2$, —S(O)$_2$NHR$^c$, —S(O)$_2$N($R^c$)$_2$, —NHS(O)$_2R^c$, —$NR^cS(O)_2R^c$, —C(O)NH$_2$, —C(O)NHR$^c$, —C(O)N($R^c$)$_2$, —C(O)$R^c$, —C(O)H, —C(=S)$R^c$, —NHC(O)$R^c$, —$NR^cC(O)R^c$, —NHC(O)NH$_2$, —$NR^cC(O)NH_2$, —$NR^cC(O)NHR^c$, —NHC(O)NHR$^c$, —$NR^cC(O)N(R^c)_2$, —NHC(O)N($R^c$)$_2$, —CO$_2$H, —CO$_2R^c$, —NHCO$_2R^c$, —$NR^cCO_2R^c$, —$R^c$, —CN, —NO$_2$, —NH$_2$, —NHR$^c$, —N($R^c$)$_2$, —$NR^cS(O)NH_2$, —$NR^cS(O)_2NHR^c$, —NH$_2$C(=$NR^c$)NH$_2$, —N=C(NH$_2$)NH$_2$, —C(=$NR^c$)NH$_2$, —N$_3$, —NH—OH, —$NR^c$—OH, —$NR^c$—$OR^c$, —N=C=O, —N=C=S, —Si($R^c$)$_3$, —NH—NHR$^c$, —NHC(O)NHNH$_2$, —P(O)(O$R^c$)$_2$, —N=C=$NR^c$ and —S—CN, wherein each $R^c$ is independently an alkyl or aryl, wherein $R^c$ is optionally further substituted with from 1-3 substituents selected from the group consisting of halogen, —OH, —$OR^d$, —SH, —$SR^d$, —S(O)$_2R^d$, —SO$_2$NH$_2$, —C(O)NH$_2$, —C(O)NHR$^d$, —C(O)N($R^d$)$_2$, —C(O)$R^d$, —C(O)H, —NHC(O)$R^d$, —$NR^dC(O)R^d$, —CO$_2$H, —CO$_2R^d$, —$R^d$, —CN, —NO$_2$, —NH$_2$, —NHR$^d$, —N($R^d$)$_2$, —NH—OH, —$NR^d$—OH, —$NR^d$—$OR^d$, —N=C=O, —N=C=S, —NH—NHR$^d$ and —S—CN, wherein each $R^d$ is independently an $(C_1-C_6)$alkyl.

2. The compound of claim 1, having formula Ia:

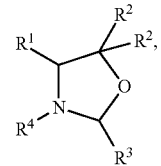

Ia wherein $R^3$ is selected from the group consisting of $(C_1-C_8)$alkyl, $(C_1-C_8)$heteroalkyl, heteroaryl-alkyl and aryl.

3. The compound of claim 1, having formula Ib:

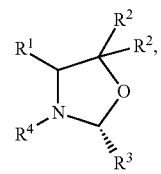

Ib wherein $R^3$ is selected from the group consisting of $(C_1-C_8)$alkyl, $(C_1-C_8)$heteroalkyl, heteroaryl-alkyl and aryl.

4. The compound of claim 1, wherein $R^3$ is —H.

5. The compound of claim 1, wherein $R^1$ is selected from the group consisting of $(C_1-C_8)$alkyl, $(C_1-C_8)$heteroalkyl, and aryl-$(C_1-C_6)$alkyl, each of which is optionally substituted with from 1-3 $R^b$.

6. The compound of claim 5, wherein $R^1$ is selected from imidazolyl-$C_1$-$C_6$alkyl, pyrazolyl-$(C_1-C_6)$alkyl, oxazolyl-$(C_1-C_6)$alkyl, isoxazolyl-$(C_1-C_6)$alkyl, thiazolyl-$(C_1-C_6)$alkyl, isothiazolyl-$(C_1-C_6)$alkyl, furanyl-$(C_1-C_6)$alkyl, and thiophenyl-$(C_1-C_6)$alkyl; each of which is optionally substituted with from 1-3 $R^b$.

7. The compound of claim 6, wherein $R^b$ is selected from the group consisting of halogen, —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —SR$^c$, —S(O)R$^c$, —S(O)$_2$R$^c$, —C(O)N(R$^c$)$_2$, —C(O)R$^c$, —C(O)H, —C(=S)R$^c$, —NHC(O)R$^c$, —NR$^c$C(O)R$^c$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —N$_3$, —NH—OH, —NR$^c$—OH and —NR$^c$—OR$^c$.

8. The compound of claim 5, wherein $R^1$ is selected from the group consisting of group consisting of -Me, —CH$_2$(Me)$_2$, —CH$_2$CH(Me)$_2$, —CHMe(Et), —CH$_2$CH$_2$CH$_3$, —CH$_2$Ph, —CH$_2$PhOH, —CH$_2$CH$_2$CH$_2$CH$_2$NH$_2$, —CH$_2$CH$_2$CONH$_2$, -Ph, -PhMe, -PhNO$_2$, -PhOCH$_3$, -PhNH$_2$, -PhF, -PhBr, -PhI, PhCN, -Ph-COOR$^c$, -Ph-OCOR$^c$, -PhNHCOR$^c$, -Ph-COOH, —CH$_2$CO$_2$H, —CH$_2$CH$_2$COOH, —CH$_2$CONH$_2$, —CH$_2$OH, —CH(OH)CH$_3$, —(CH$_2$)$_3$NHC(=NH)NH$_2$, —CH$_2$CH$_2$CHNHCH(NH$_2$)$_2$, imidazolyl-CH$_2$—, imidazol-4-yl-CH$_2$—, imidazol-5-yl-CH$_2$—, CH$_2$CH$_2$SMe and —CH$_2$SH.

9. The compound of claim 8, wherein $R^1$ is selected from the group consisting of —CH$_2$CH(Me)$_2$, CH$_3$CH$_2$(CH$_3$)CH—, benzyl or imidazoly-CH$_2$—.

10. The compound of claim 1, wherein $R^2$ is optionally substituted with from 1-3 $R^b$.

11. The compound of claim 10, wherein $R^2$ is optionally substituted with from 1-3 $R^b$ substituents selected from the group consisting of —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —SR$^c$, —S(O)R$^c$, —S(O)$_2$R$^c$, —C(O)N(R$^c$)$_2$, —C(O)R$^c$, —C(O)H, —C(=S)R$^c$, —NHC(O)R$^c$, —NR$^c$C(O)R$^c$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —N$_3$, —NH—OH, —NR$^c$—OH and —NR$^c$—OR$^c$.

12. The compound of claim 11, wherein $R^b$ is selected from the group consisting of halogen, —OH, —OR$^c$, —R$^c$, —CN, —NO$_2$, —NH$_2$, —NHR$^c$ and —N(R$^c$)$_2$.

13. The compound of claim 10, wherein $R^2$ is selected from the group consisting of —H, -Me, -Et, —Pr, -Bu, i-Pr, t-Bu, i-Bu, —CH$_2$CH$_2$CH$_2$CH$_2$CH$_3$.

14. The compound of claim 1, wherein $R^3$ is selected from the group consisting of —H, (C$_1$-C$_8$)alkyl and aryl, wherein the alkyl and aryl are optionally substituted with from 1-3 $R^b$.

15. The compound of claim 14, wherein $R^3$ is selected from the group consisting of —H, (C$_1$-C$_8$)alkyl and phenyl, wherein the alkyl and phenyl are each optionally substituted with from 1-3 $R^b$ substituents selected from the group consisting of —OH, —OR$^c$, —OSi(R$^c$)$_3$, —OC(O)O—R$^c$, —OC(O)R$^c$, —OC(O)NHR$^c$, —OC(O)N(R$^c$)$_2$, —SH, —SW, —S(O)R$^c$, —S(O)$_2$R$^c$, —C(O)N(R$^c$)$_2$, —C(O)R$^c$, —C(O)H, —C(=S)R$^c$, —NHC(O)R$^c$, —NR$^c$C(O)R$^c$, —CO$_2$H, —CO$_2$R$^c$, —NHCO$_2$R$^c$, —NR$^c$CO$_2$R$^c$, —R$^c$, —CN, —NO$_2$, —NH$_2$, —NHR$^c$, —N(R$^c$)$_2$, —N$_3$, —NH—OH, —NR$^c$—OH and —NR$^c$—OR$^c$.

16. The compound of claim 15, wherein $R^b$ is selected from the group consisting of halogen, —OH, —OR$^c$, —R$^c$, —CN, —NO$_2$, —NH$_2$, —NHR$^c$ and —N(R$^c$)$_2$.

17. The compound of claim 14, wherein $R^3$ is selected from the group consisting of —H, -Me, -Et, —Pr, -Bu, i-Pr, t-Bu, i-Bu, —CH$_2$CH$_2$CH$_2$CH$_2$CH$_3$, -Ph, -PhMe, -PhNO$_2$, -PhOMe, -PhNH$_2$, -Ph-F, -Ph-Br, -Ph-Cl, -Ph-I, -PhCN, -Ph-COOR$^c$, -Ph-OCOR$^c$, —PhNHCOR$^c$ and -Ph-COOH.

18. The compound of claim 1, wherein $R^4$ is selected from the group consisting of —H, aryl-(C$_1$-C$_6$)alkyl, (C$_1$-C$_8$)alkyl, (C$_1$-C$_8$)heteroalkyl, —C(O)NH$_2$, —C(O)NHR$^a$, —C(O)N(R$^a$)$_2$, —C(O)R$^a$, —C(O)H, —C(=S)R$^a$, —CO$_2$H, —CO$_2$R$^a$, —P(O)(OR$^a$)$_2$ and an amino protecting group, wherein the aliphatic and aromatic portions of the $R^4$ group are each optionally substituted with from 1-3 $R^b$ substituents.

19. The compound of claim 18, wherein $R^4$ is selected from the group consisting of —H, phenyl-(C$_1$-C$_6$)alkyl, (C$_1$-C$_8$)alkyl, —C(O)NH$_2$, —C(O)NHR$^a$, —C(O)N(R$^a$)$_2$, —C(O)R$^a$, —C(O)H, —C(=S)R$^a$, —CO$_2$H, —CO$_2$R$^a$ and an amino protecting group, wherein $R^a$ is alkyl or phenyl optionally substituted with from 1-3 $R^b$ groups.

20. The compound of claim 18, wherein $R^4$ is selected from the group consisting of —H, —CHO, PhCO—, PhNHCO—, PhOCO—, CH$_3$NHCO—, CH$_3$OCO—, CH$_3$CO—, EtCO—, -Me, -Et, —Pr, -Bu, i-Pr, i-Bu, t-Bu, —CH$_2$CH$_2$CH$_2$CH$_2$CH$_3$ and t-BuO-CO—.

21. The compound of claim 1, wherein the compound is selected from the group consisting of:

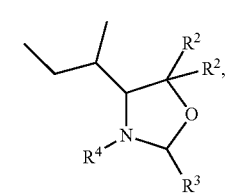

Ia-1

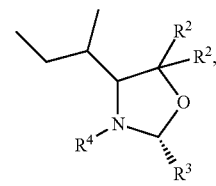

Ib-1

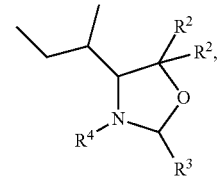

Ic-1

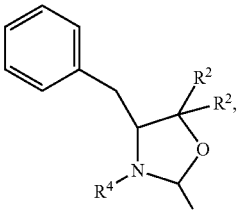

Ia-2

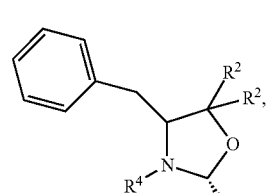

Ib-2

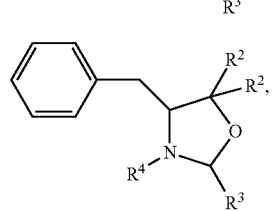

Ic-2

-continued

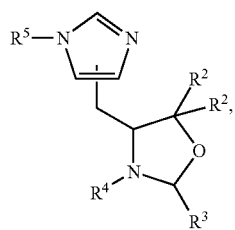
Ia-3

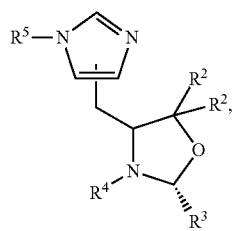
Ib-3

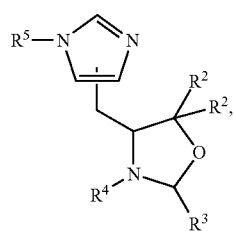
Ic-3

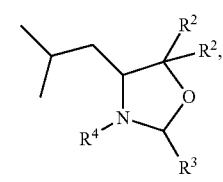
Ia-4

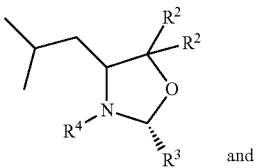
Ib-4 and

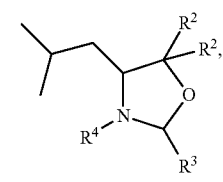
Ic-4 wherein R⁵ is selected from the group consisting of —H, (C₁-C₈)alkyl, (C₁-C₈)heteroalkyl, arylalkyl, (C₃-C₈)cycloalkyl, (C₃-C₈)cycloalkyl-alkyl, —X¹S(O)Rᵃ, —X¹S(O)₂Rᵃ, —X¹SO₂NH₂, —X¹S(O)₂NHRᵃ, —X¹S(O)₂N(Rᵃ)₂, —X¹C(O)NH₂, —X¹C(O)NHRᵃ, —X¹C(O)N(Rᵃ)₂, —X¹C(O)Rᵃ, —X¹C(O)H, —X¹C(=S)Rᵃ, —X¹CO₂H, —X¹CO₂Rᵃ, —X¹P(O)(ORᵃ)₂ and an amino protecting group.

22. The compound of claim 21, wherein the compound is selected from the group consisting of:

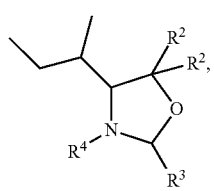
Ia-1

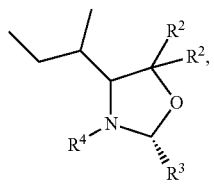
Ib-1

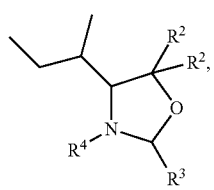
Ic-1

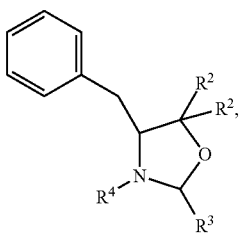
Ia-2

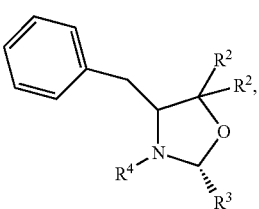
Ib-2

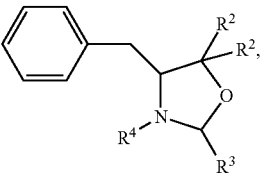
Ic-2

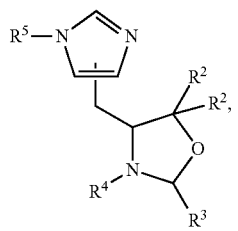
Ia-3'

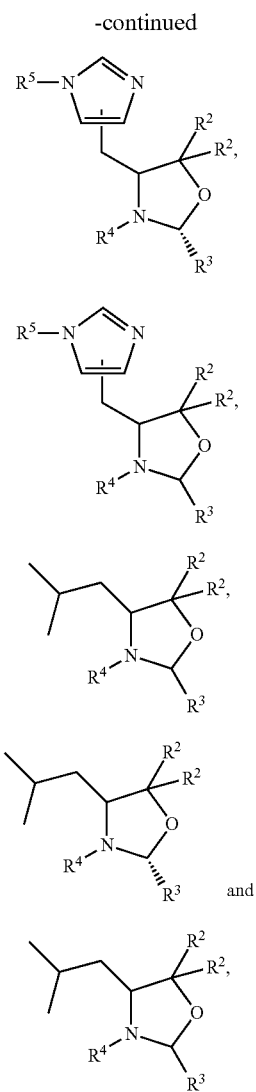

Ib-3'

Ic-3'

Ia-4

Ib-4 and

Ic-4 wherein $R^5$ is selected from the group consisting of —H, $(C_1-C_8)$alkyl, $(C_1-C_8)$heteroalkyl, arylalkyl, $(C_3-C_8)$cycloalkyl, $(C_3-C_8)$cycloalkyl-alkyl, —$X^1S(O)R^a$, —$X^1S(O)_2R^a$, —$X^1SO_2NH_2$, —$X^1S(O)_2NHR^a$, —$X^1S(O)_2N(R^a)_2$, —$X^1C(O)NH_2$, —$X^1C(O)NHR^a$, —$X^1C(O)N(R^a)_2$, —$X^1C(O)R^a$, —$X^1C(O)H$, —$X^1C(=S)R^a$, —$X^1CO_2H$, —$X^1CO_2R^a$, —$X^1P(O)(OR^a)_2$ and an amino protecting group.

23. The compound of claim 21, wherein $R^2$ is $(C_1-C_8)$alkyl, $R^3$ is $(C_1-C_8)$alkyl or aryl optionally substituted with from 1-3 $R^b$ groups and $R^4$ is —H or —$COR^a$.

24. The compound of claim 23, wherein $R^3$ is $(C_1-C_8)$alkyl.

25. The compound of claim 23, wherein $R^3$ is an aryl optionally substituted with from 1-3 $R^b$ groups.

26. The compound of claim 23, wherein $R^4$ is —H.

27. The compound of claim 23, wherein $R^4$ is —$COR^a$.

28. The compound of claim 27, wherein $R^a$ is phenyl optionally substituted with from 1-3 $R^b$ groups.

29. The compound of claim 21, wherein $R^4$ is $(C_1-C_8)$alkyl, $R^2$ is $(C_1-C_8)$alkyl and $R^3$ is $(C_1-C_8)$alkyl or aryl, wherein the aryl of $R^3$ groups is optionally substituted with from 1-3 $R^b$.

30. The compound of claim 29, wherein $R^4$ is $(C_1-C_8)$alkyl, $R^2$ is $(C_1-C_8)$alkyl and $R^3$ is $(C_1-C_8)$alkyl or aryl optionally substituted with from 1-3 $R^b$ groups.

31. The compound of claim 29, wherein $R^4$ is $(C_1-C_8)$alkyl and $R^3$ is an aryl optionally substituted with from 1-3 $R^b$ groups.

32. The compound of claim 29, wherein the aryl is phenyl optionally substituted with from 1-3 $R^b$ groups.

33. A pharmaceutical composition comprising a compound of claim 1 and a pharmaceutically acceptable carrier or excipient.

34. A method of inhibiting the activities of an NMDA receptor, said method comprising: contacting a compound of claim 1 with the NMDA receptor.

35. The method of claim 34, wherein the NMDA receptor is an activated glutamate receptor.

36. A method of inhibiting the synapse transmission by glutamate, said method comprising: contacting a compound of claim 1 with an activated extrasynaptic NMDA receptor.

37. A method of treating central nervous system disorders in a mammal, said method comprising: contacting a compound of claim 1 with the NMDA receptor.

38. A method of treating or preventing a neurodegenerative disease or neuropathological conditions in a mammal, said method comprising: administering to said mammal a therapeutically effective amount of a compound of claim 1.

39. The method of claim 38, wherein said disease is selected from the group consisting of amyotrophic lateral sclerosis, Alzheimer's disease, Parkinson's disease, Huntington's disease, neuropathic pain, stroke, epilepsy, CNS trauma, brain trauma, and cardiac arrest.

40. The method of claim 38, wherein said condition is selected from the group consisting of neuropathic pain, stroke, brain trauma and epilepsy.

41. A method of enhancing the brain's cognitive function in a mammal, said method comprising: administering to said mammal a therapeutically effective amount of a compound of claim 1.

42. A method of treating neuronal damage under a stress condition in a mammal, said method comprising: administering to said mammal a therapeutically effective amount of a compound of claim 1.

43. The method of claim 42, wherein said stress condition is a stroke, head trauma or cardiac arrest.

44. A method of inhibiting the activities of an NMDA receptor, said method comprising: contacting the NMDA receptor with any of

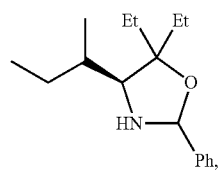

4i

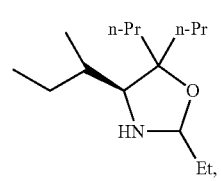

4j

-continued
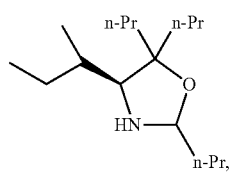 4k
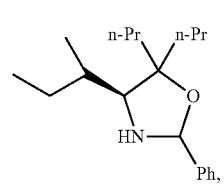 4l
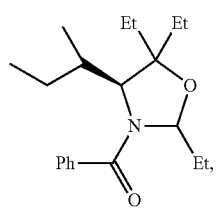 5e
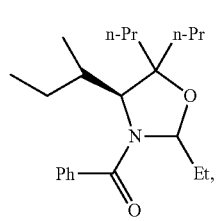 5f
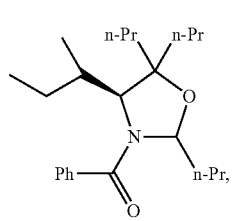 5g
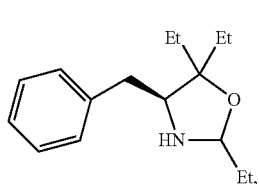 4m
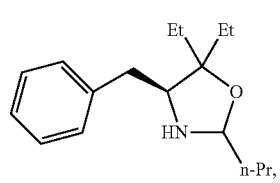 4n
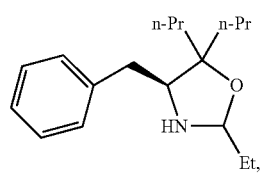 4o
-continued
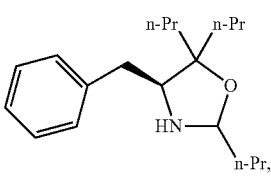 4p
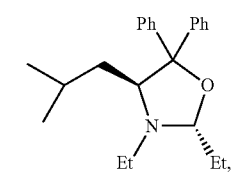 8a
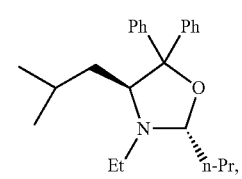 8b
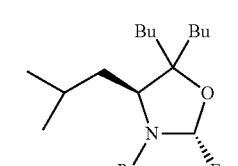 8c
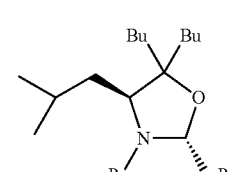 8d
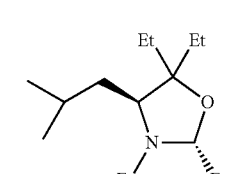 8e
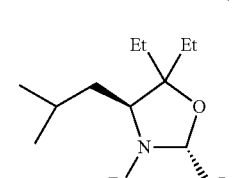 8f
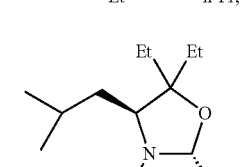 8g
LC-1

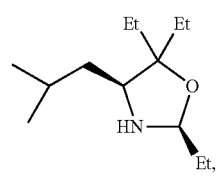 LC-2
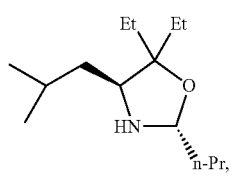 LC-3
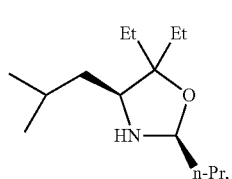 LC-4
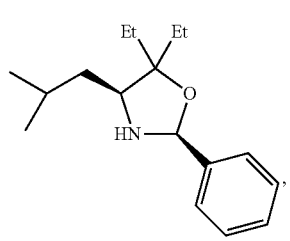 LC-5
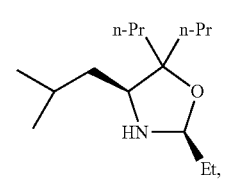 LC-6
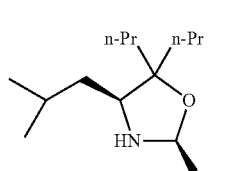 LC-7
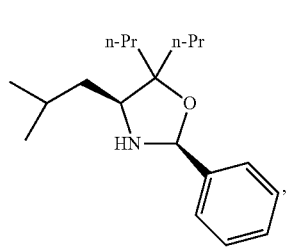 LC-8
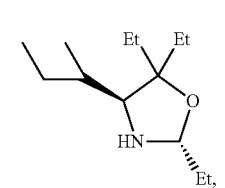 LC-9
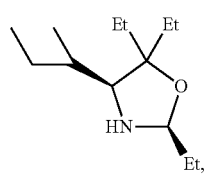 LC-10
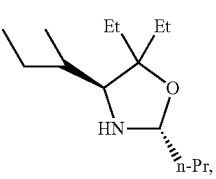 LC-11
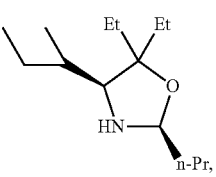 LC-12
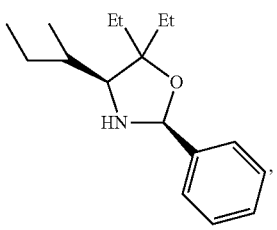 LC-13
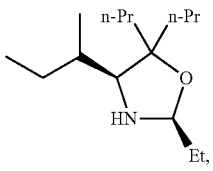 LC-14
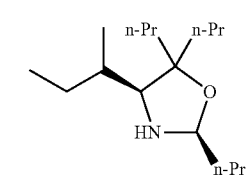 LC-15
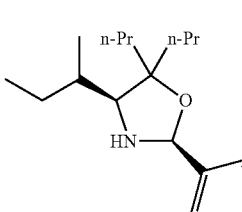 LC-16
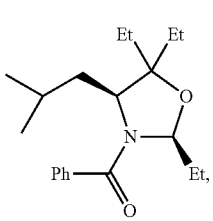 LC-17

| | |
|---|---|
| LC-18 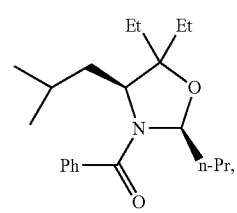 | LC-26 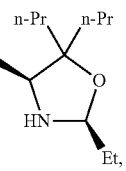 |
| LC-19 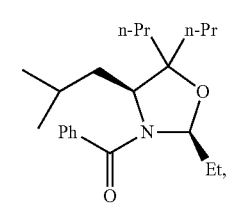 | LC-27 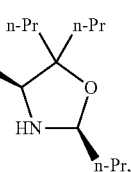 |
| LC-20 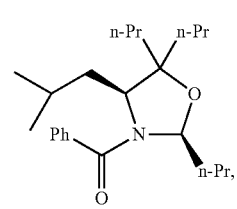 | LC-28 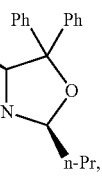 |
| LC-21 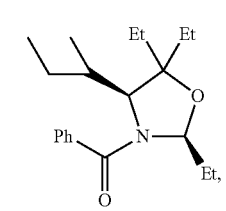 | LC-29 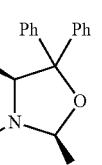 |
| LC-22 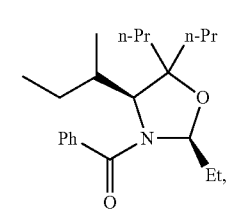 | LC-30 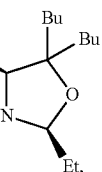 |
| LC-23 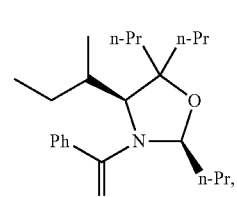 | LC-31 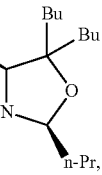 |
| LC-24 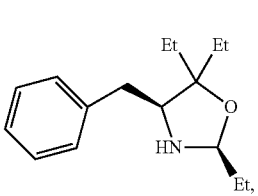 | LC-32 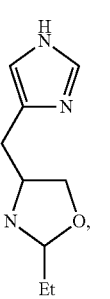 |
| LC-25 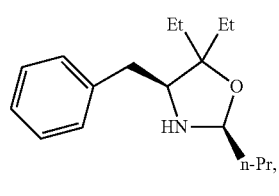 | |

LC-33 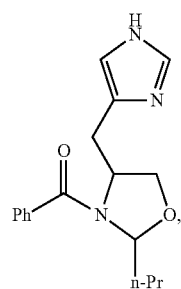
LC-34 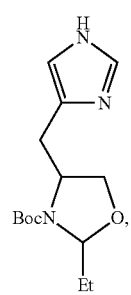
LC-35 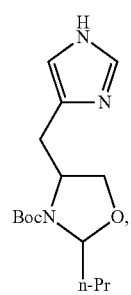
LC-36 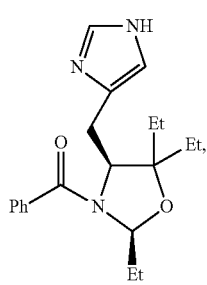
LC-37 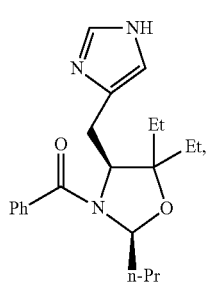
LC-38 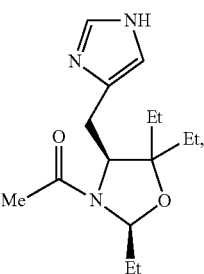
LC-39 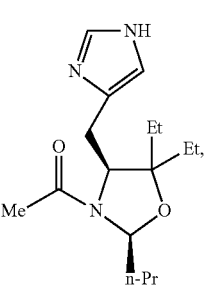
LC-40 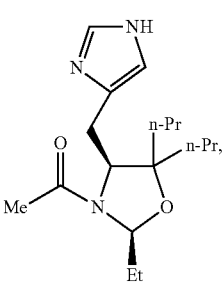
LC-41 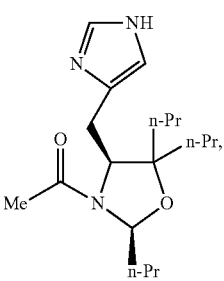
LC-42 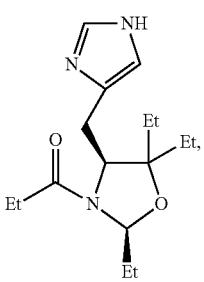

| | |
|---|---|
| LC-43 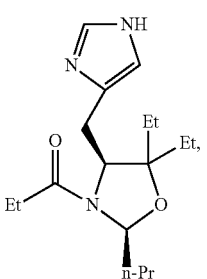 | LC-02-d04 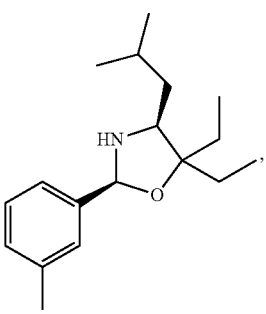 |
| LC-44 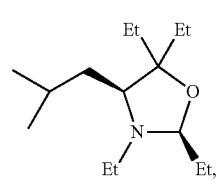 | LC-02-d05 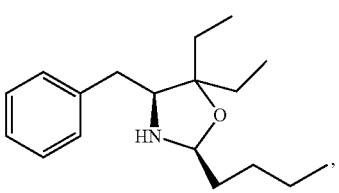 |
| LC-45 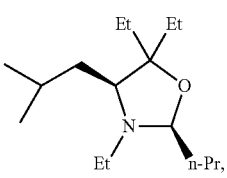 | LC-02-d06 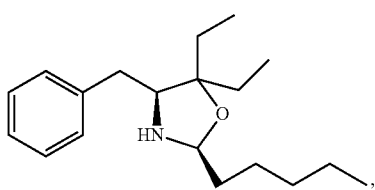 |
| LC-46 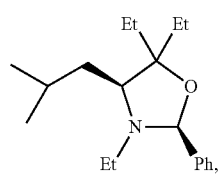 | LC-02-d07 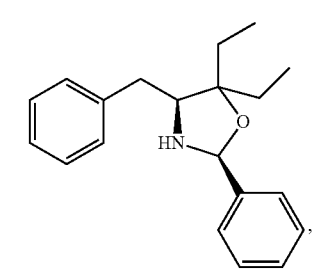 |
| LC-02-d01 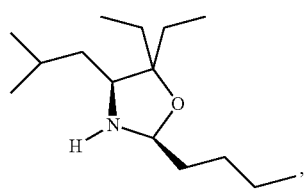 | LC-02-d08 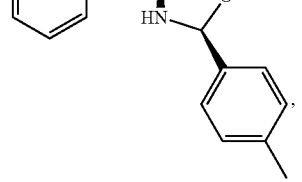 |
| LC-02-d02 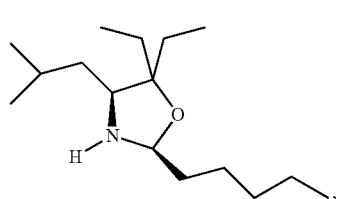 | |
| LC-02-d03 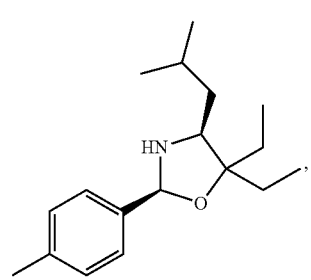 | LC-02-d09 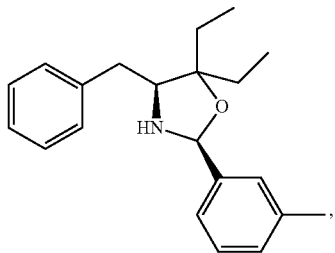 |

-continued
LC-02-d10
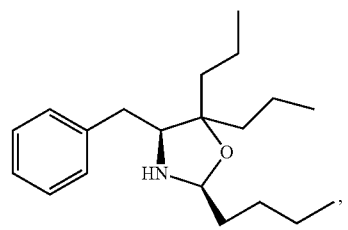
LC-02-d11
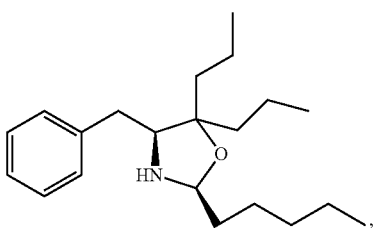
LC-02-d12
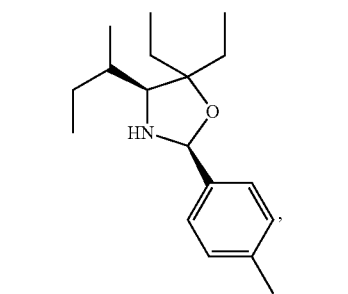
LC-02-d13
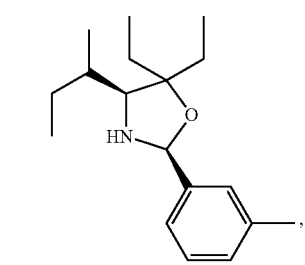
LC-02-d14
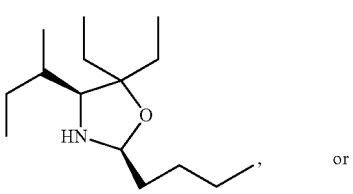
or
LC-02-d15
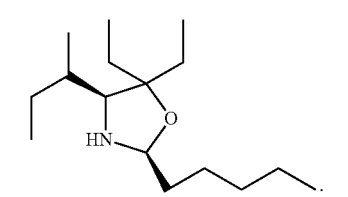
45. A method of treating neurodegenerative diseases and neuropathological disorders or enhancing the brain's cognitive function in a mammal, said method comprising: administering to said mammal a therapeutically effective amount of any of
4i
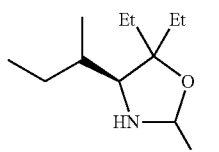
4j
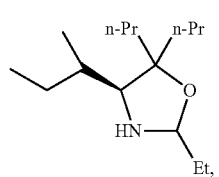
4k
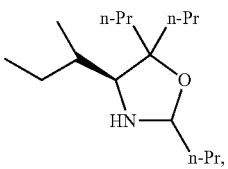
4l
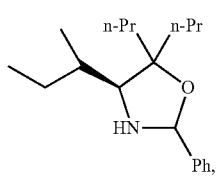
5e
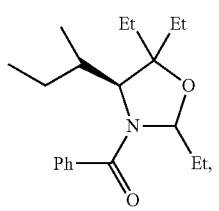
5f
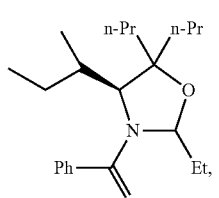
5g
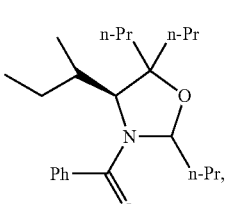
4m
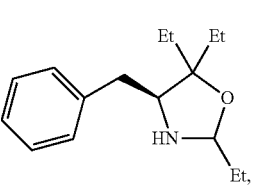

105
-continued
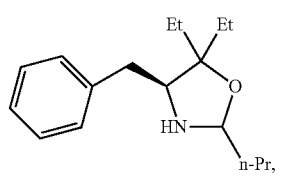 4n
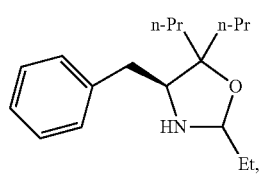 4o
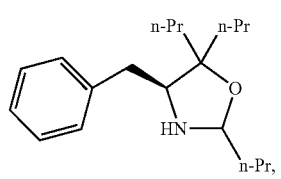 4p
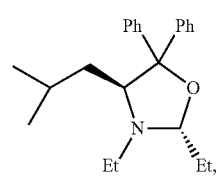 8a
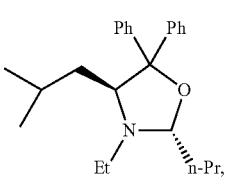 8b
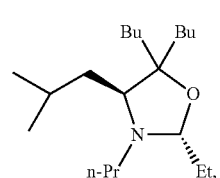 8c
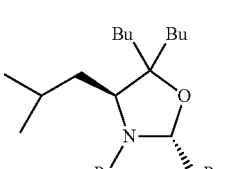 8d
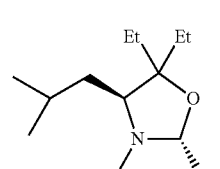 8e
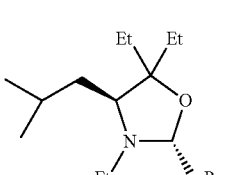 8f
106
-continued
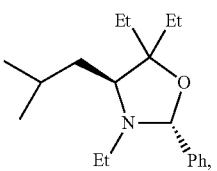 8g
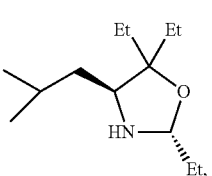 LC-1
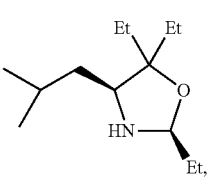 LC-2
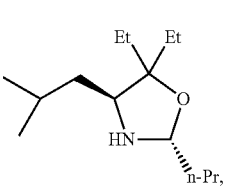 LC-3
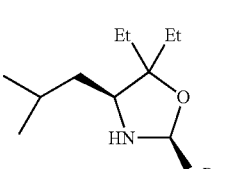 LC-4
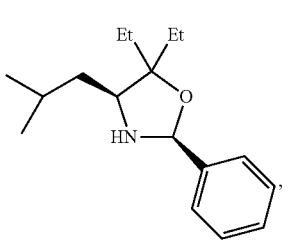 LC-5
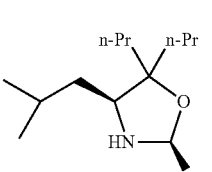 LC-6
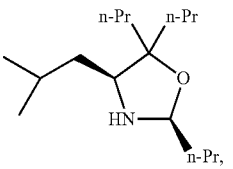 LC-7

| 107 -continued | | 108 -continued | |
|---|---|---|---|
| 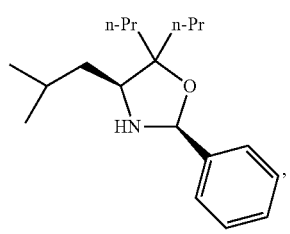 | LC-8 | 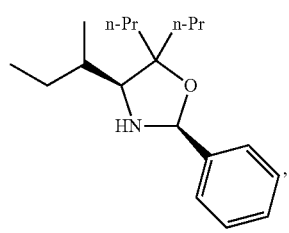 | LC-16 |
| 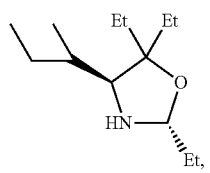 | LC-9 | 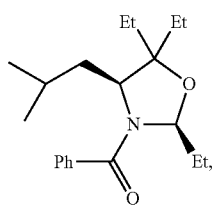 | LC-17 |
| 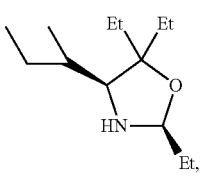 | LC-10 | 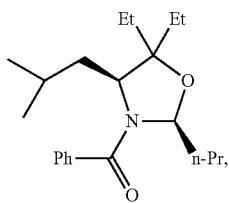 | LC-18 |
| 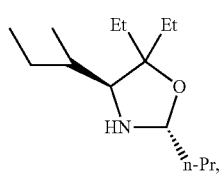 | LC-11 | 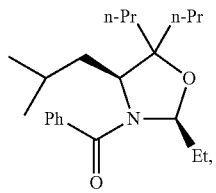 | LC-19 |
| 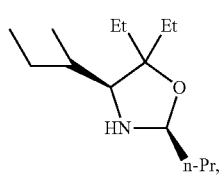 | LC-12 | 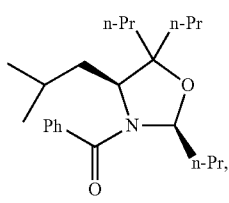 | LC-20 |
| 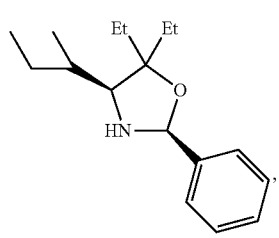 | LC-13 | 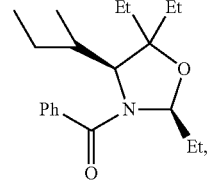 | LC-21 |
| 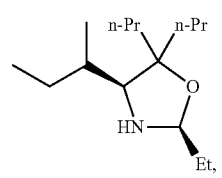 | LC-14 | 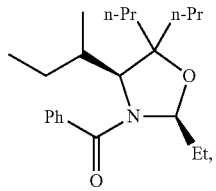 | LC-22 |
| 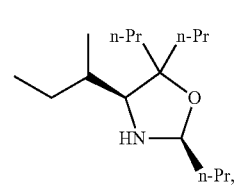 | LC-15 | 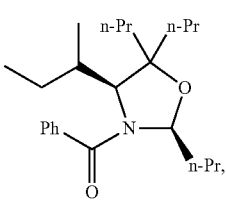 | LC-23 |

| | |
|---|---|
| 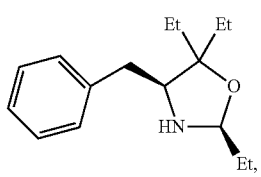 | LC-24 |
| 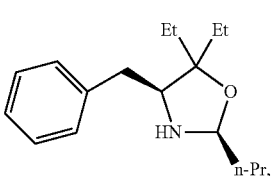 | LC-25 |
| 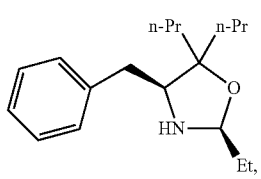 | LC-26 |
| 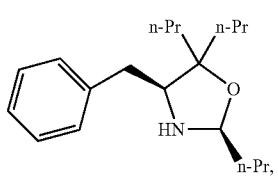 | LC-27 |
| 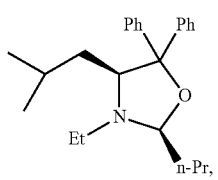 | LC-28 |
| 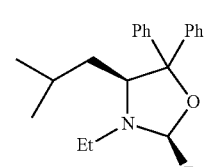 | LC-29 |
| 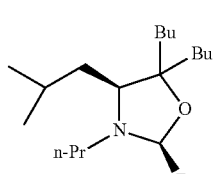 | LC-30 |
| 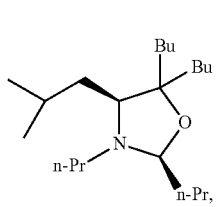 | LC-31 |
| | |
|---|---|
| 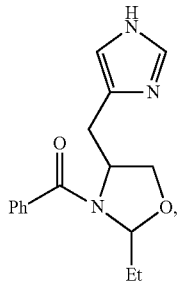 | LC-32 |
| 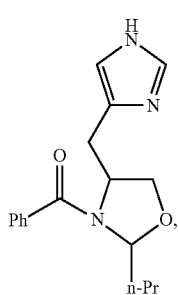 | LC-33 |
| 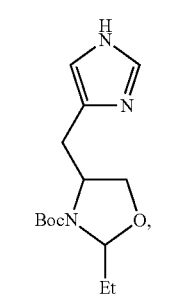 | LC-34 |
| | LC-35 |
| 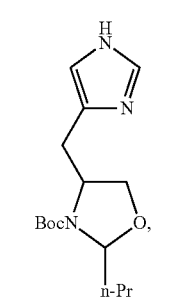 | LC-36 |

| | |
|---|---|
| LC-37 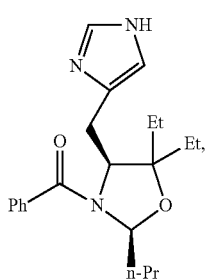 | LC-42 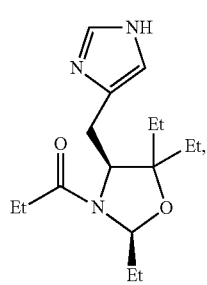 |
| LC-38 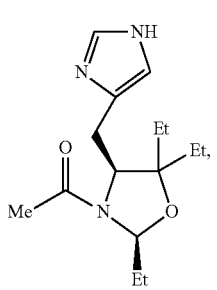 | LC-43 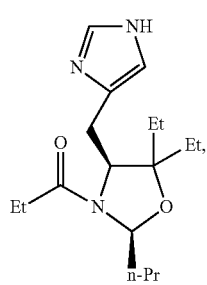 |
| LC-39 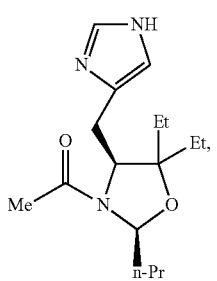 | LC-44 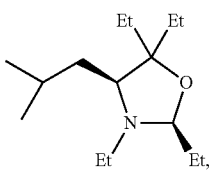 |
| | LC-45 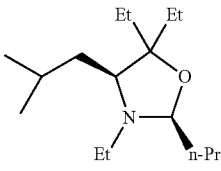 |
| LC-40 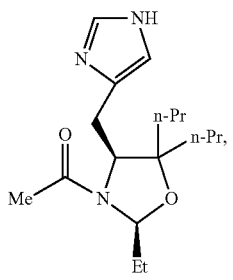 | LC-46 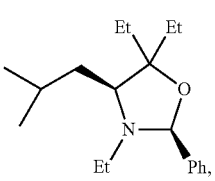 |
| | LC-02-d01 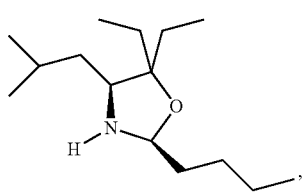 |
| LC-41 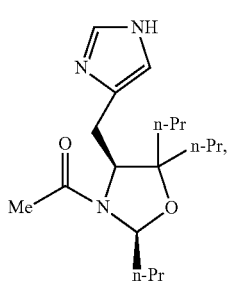 | LC-02-d02 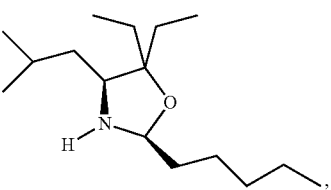 |

LC-02-d03
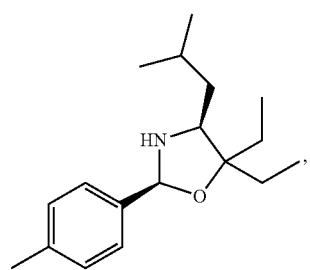
LC-02-d04
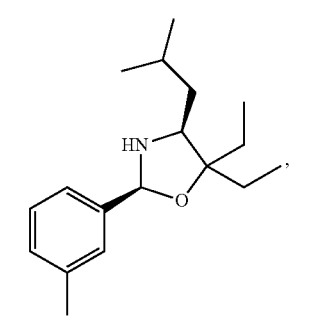
LC-02-d05
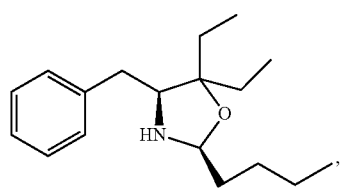
LC-02-d06
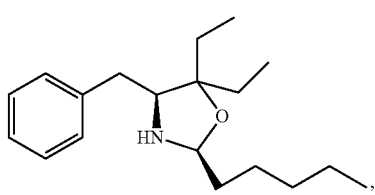
LC-02-d07
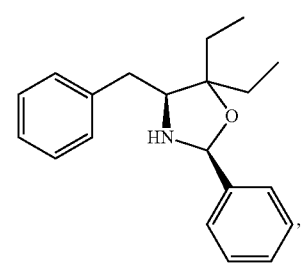
LC-02-d08
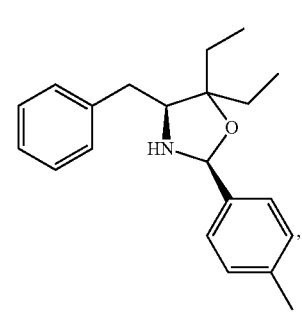
LC-02-d09
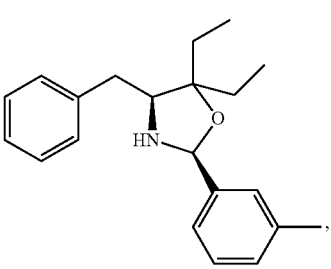
LC-02-d10
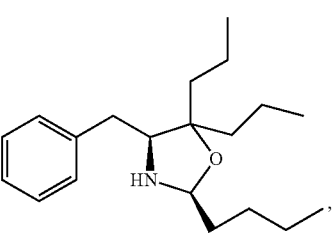
LC-02-d11
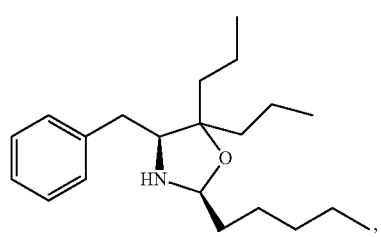
LC-02-d12
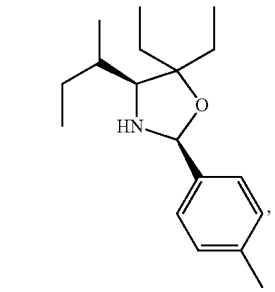
LC-02-d13
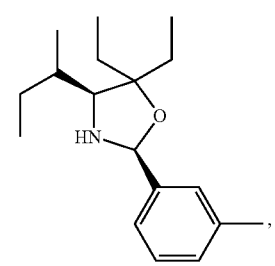
LC-02-d14
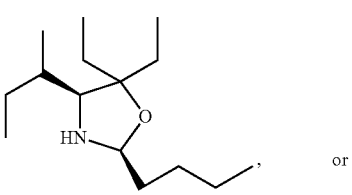 or LC-02-d15
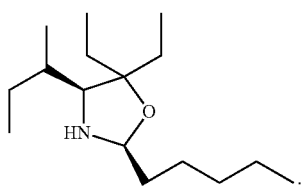
46. A method of treating neuronal damage under a stress condition in a mammal, said method comprising: administering to said mammal a therapeutically effective amount of any of
4i
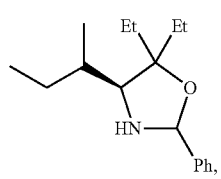
4j
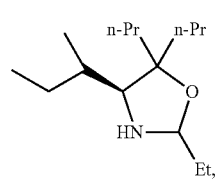
4k
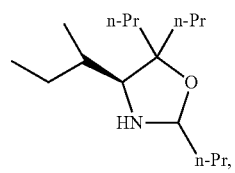
4l
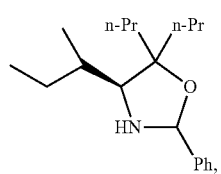
5e
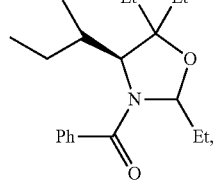
5f
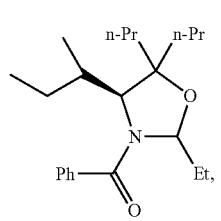
5g
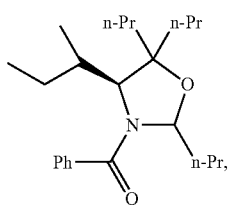
4m
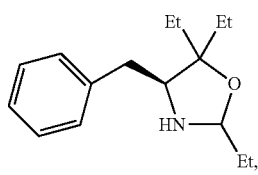
4n
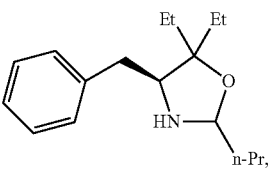
4o
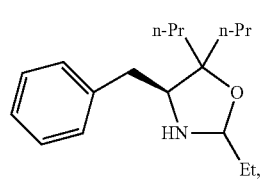
4p
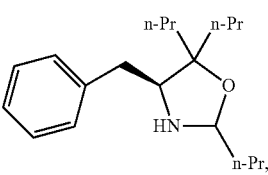
8a
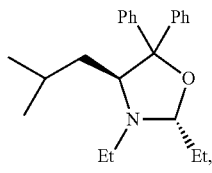
8b
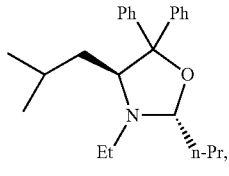
8c
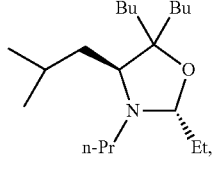
8d

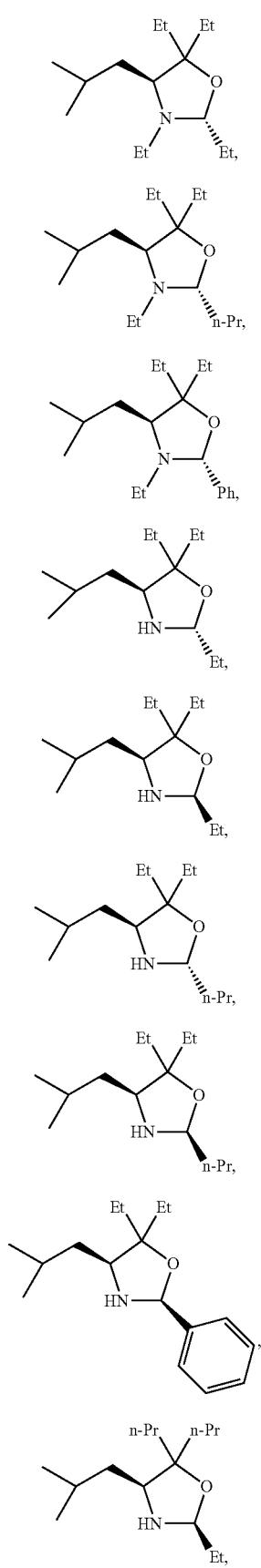
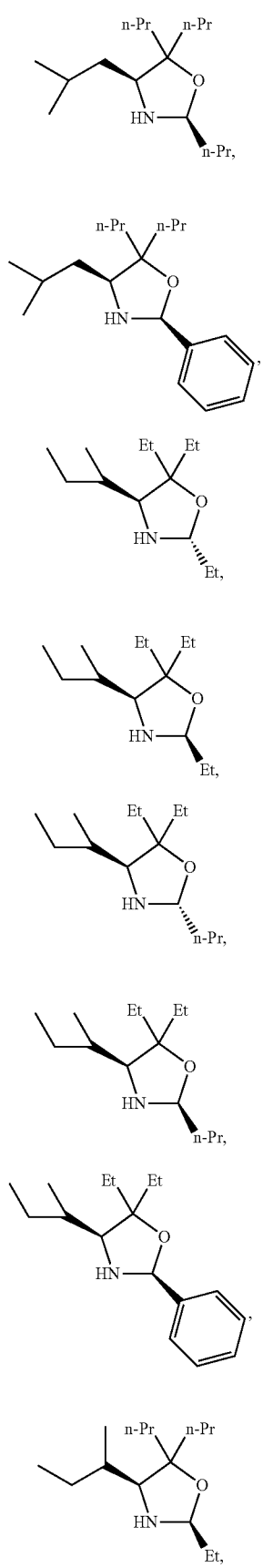

LC-15
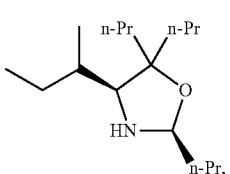
LC-16
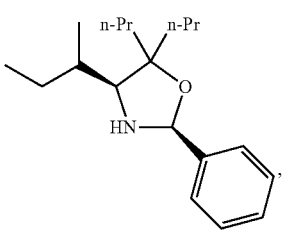
LC-17
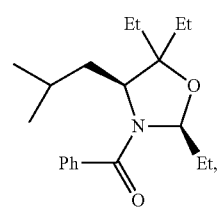
LC-18
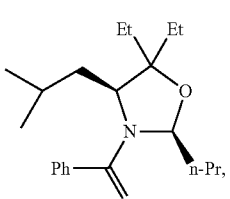
LC-19
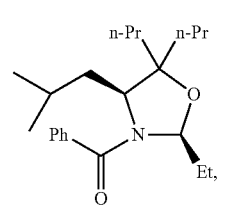
LC-20
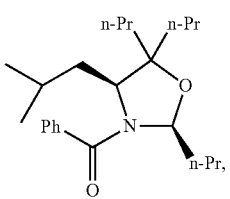
LC-21
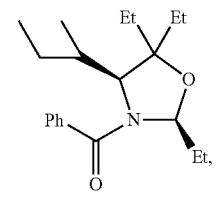
LC-22
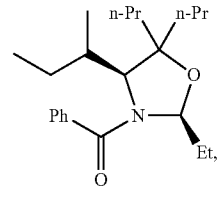
LC-23
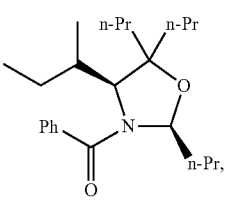
LC-24
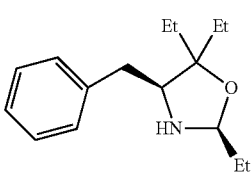
LC-25
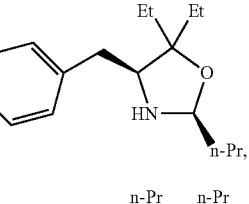
LC-26
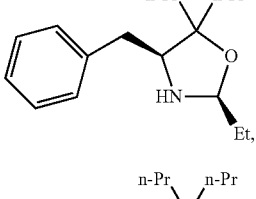
LC-27
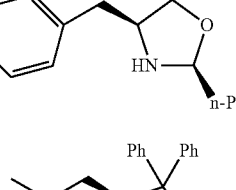
LC-28
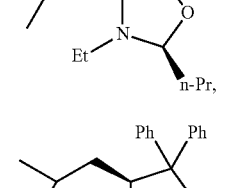
LC-29
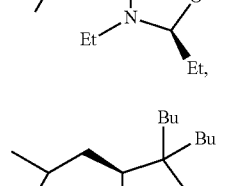
LC-30
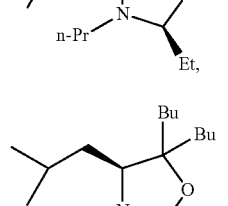
LC-31
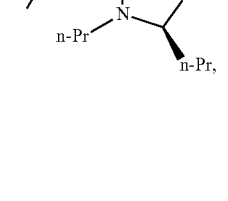

| | |
|---|---|
| 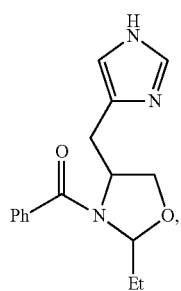 LC-32 | 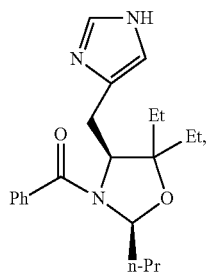 LC-37 |
| 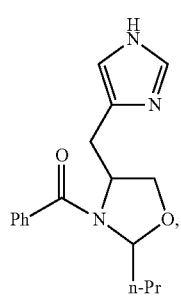 LC-33 | 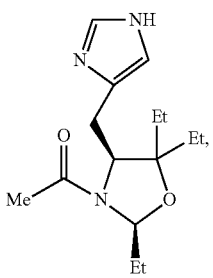 LC-38 |
| 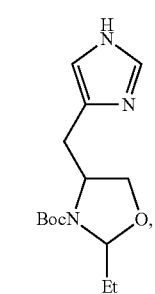 LC-34 | 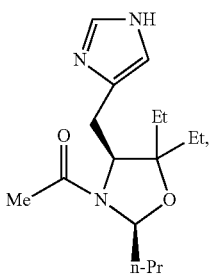 LC-39 |
| 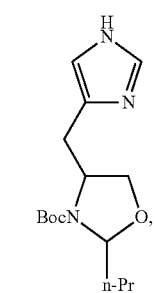 LC-35 | 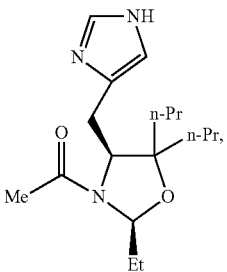 LC-40 |
| 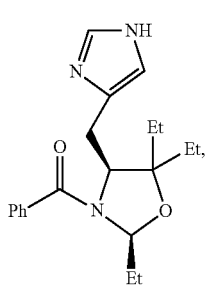 LC-36 | 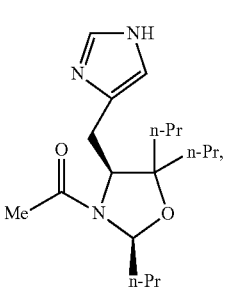 LC-41 |

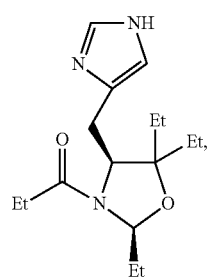
LC-42
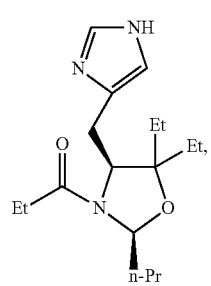
LC-43
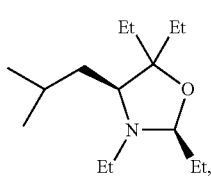
LC-44
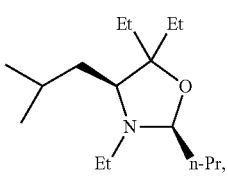
LC-45
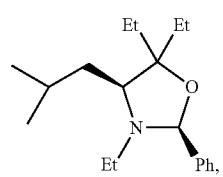
LC-46
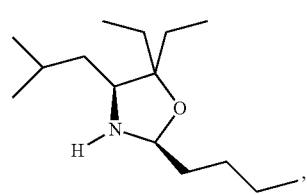
LC-02-d01
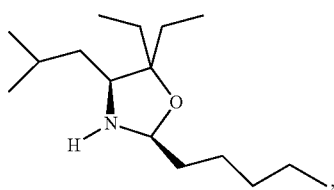
LC-02-d02
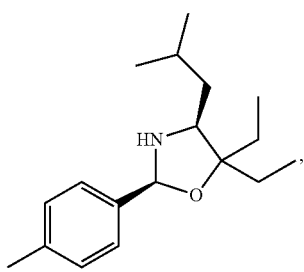
LC-02-d03
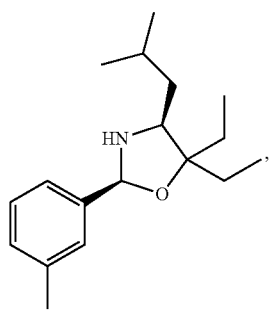
LC-02-d04
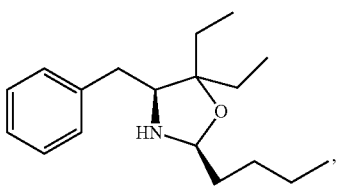
LC-02-d05
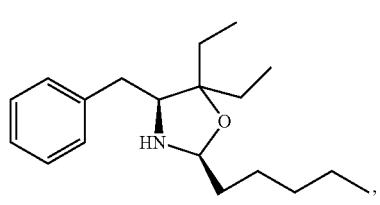
LC-02-d06
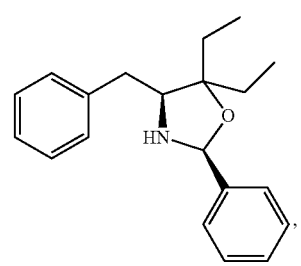
LC-02-d07

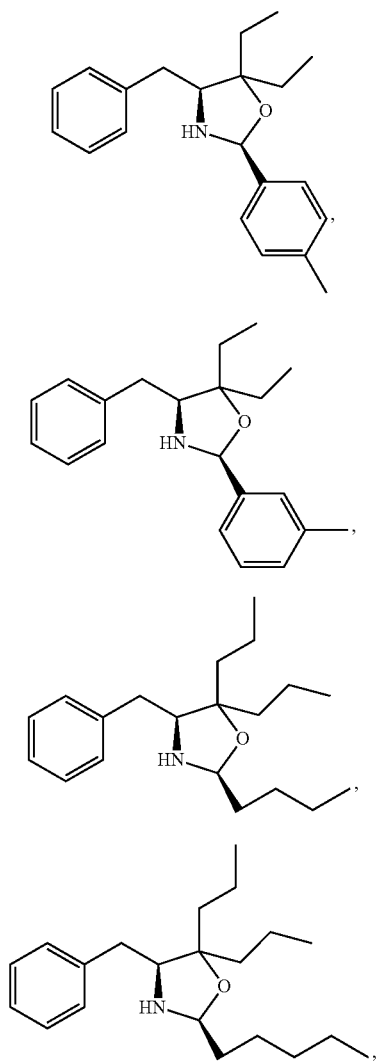
LC-02-d08
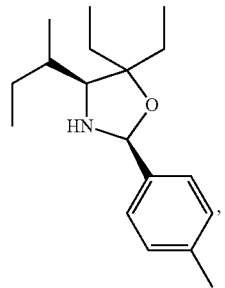
LC-02-d12
LC-02-d09
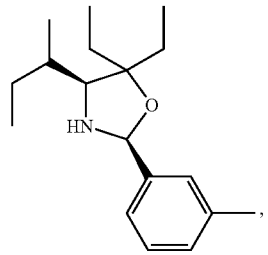
LC-02-d13
LC-02-d10
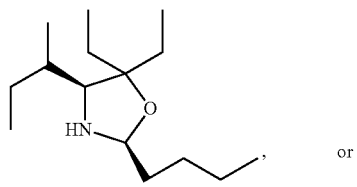
, or
LC-02-d14
LC-02-d11
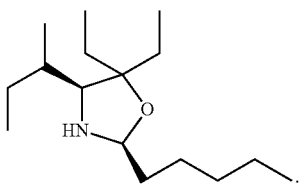
.
LC-02-d15
* * * * *